(12) United States Patent
Loesener et al.

(10) Patent No.: US 10,857,330 B2
(45) Date of Patent: Dec. 8, 2020

(54) APPARATUSES, SYSTEMS, AND METHODS FOR INSERTING CATHETERS HAVING ENHANCED STIFFENING AND GUIDING FEATURES

(71) Applicant: C. R. Bard, Inc., Murray Hill, NJ (US)

(72) Inventors: German Loesener, Riverton, UT (US); Ericka J. Prechtel, Salt Lake City, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 71 days.

(21) Appl. No.: 16/384,509

(22) Filed: Apr. 15, 2019

(65) Prior Publication Data

US 2019/0240453 A1 Aug. 8, 2019

Related U.S. Application Data

(62) Division of application No. 14/799,547, filed on Jul. 14, 2015, now Pat. No. 10,258,768.
(Continued)

(51) Int. Cl.
*A61M 25/01* (2006.01)
*A61M 1/36* (2006.01)
*A61M 25/00* (2006.01)

(52) U.S. Cl.
CPC ...... *A61M 25/0102* (2013.01); *A61M 1/3661* (2014.02); *A61M 25/0009* (2013.01); *A61M 2025/0031* (2013.01)

(58) Field of Classification Search
CPC ........ A61M 1/3661; A61M 2025/0031; A61M 25/0009; A61M 25/0102
See application file for complete search history.

(56) References Cited

U.S. PATENT DOCUMENTS 701,075 A 5/1902 McCully
1,696,018 A 12/1928 Scheliberg
(Continued)

FOREIGN PATENT DOCUMENTS

BE 834211 A 2/1976
CA 1150122 A 7/1983
(Continued)

OTHER PUBLICATIONS

U.S. Appl. No. 10/371,774, filed Feb. 21, 2003 Notice of Allowance dated Jun. 1, 2007.
(Continued)

*Primary Examiner* — Brandy S Lee
(74) *Attorney, Agent, or Firm* — Rutan & Tucker LLP

(57) ABSTRACT

A catheter assembly including a multi-lumen catheter, a stylet, and a guide-wire. The multi-lumen catheter includes a first lumen in fluid communication with a first distal opening and a second lumen in fluid communication with a second distal opening. The stylet is designed for insertion through the first lumen, having a length greater than a length of the first lumen such that a distal portion of the stylet can extend distal of the first distal opening. The distal portion of the stylet can include a stylet distal opening, a stylet proximal opening in communication with the stylet distal opening, and an expandable portion. The expandable portion can include a first expansion side and a second expansion side at least partially separable from the first expansion side. The stylet proximal opening can be formed through the first expansion side.

7 Claims, 30 Drawing Sheets

Related U.S. Application Data

(60) Provisional application No. 62/024,323, filed on Jul. 14, 2014, provisional application No. 62/024,423, filed on Jul. 14, 2014.

(56) References Cited

U.S. PATENT DOCUMENTS

| | | |
|---|---|---|
| 1,856,811 A | 5/1932 | Inaki |
| 2,024,982 A | 12/1935 | Scott |
| 2,173,527 A | 9/1939 | Agayoff |
| 2,286,462 A | 6/1942 | Chaffin |
| 2,393,002 A | 1/1946 | Smith |
| 2,748,769 A | 6/1956 | Huber |
| 2,910,981 A | 11/1959 | Wilson et al. |
| 3,144,868 A | 8/1964 | Jascalevich |
| 3,176,690 A | 4/1965 | H'Doubler |
| 3,256,885 A | 6/1966 | Higgins et al. |
| 3,308,822 A | 3/1967 | De Luca |
| 3,416,532 A | 12/1968 | Grossman |
| 3,426,759 A | 2/1969 | Smith |
| 3,460,255 A | 8/1969 | Hutson |
| D217,795 S | 6/1970 | Spaven |
| 3,612,038 A | 10/1971 | Halligan |
| 3,736,939 A | 6/1973 | Taylor |
| 3,805,794 A | 4/1974 | Schlesinger |
| 3,812,851 A | 5/1974 | Rodriguez |
| 3,848,604 A | 11/1974 | Sackner |
| 3,890,977 A | 6/1975 | Wilson |
| 3,929,126 A | 12/1975 | Corsaut |
| 3,935,857 A | 2/1976 | Co |
| 3,995,623 A | 12/1976 | Blake et al. |
| 4,068,659 A | 1/1978 | Moorehead |
| 4,072,146 A | 2/1978 | Howes |
| 4,072,153 A | 2/1978 | Swartz |
| 4,098,275 A | 7/1978 | Consalvo |
| 4,114,625 A | 9/1978 | Onat |
| 4,117,836 A | 10/1978 | Erikson |
| 4,129,129 A | 12/1978 | Amrine |
| 4,134,402 A | 1/1979 | Mahurkar |
| 4,149,535 A | 4/1979 | Volder |
| 4,180,068 A | 12/1979 | Jacobsen et al. |
| D254,444 S | 3/1980 | Levine |
| 4,248,224 A | 2/1981 | Jones |
| 4,276,880 A | 7/1981 | Malmin |
| 4,292,976 A | 10/1981 | Banka |
| 4,299,228 A | 11/1981 | Peters |
| 4,300,550 A | 11/1981 | Gandi et al. |
| 4,309,994 A | 1/1982 | Grunwald |
| 4,327,722 A | 5/1982 | Groshong et al. |
| 4,385,631 A | 5/1983 | Uthmann |
| 4,392,855 A | 7/1983 | Oreopoulos et al. |
| 4,403,983 A | 9/1983 | Edelman et al. |
| 4,405,313 A | 9/1983 | Sisley et al. |
| 4,406,656 A | 9/1983 | Hattler et al. |
| D272,651 S | 2/1984 | Mahurkar |
| 4,431,426 A | 2/1984 | Groshong et al. |
| 4,432,722 A | 2/1984 | Bohan, Jr. et al. |
| 4,432,752 A | 2/1984 | Marlon |
| 4,445,893 A | 5/1984 | Bodicky |
| 4,451,252 A | 5/1984 | Martin |
| 4,453,928 A | 6/1984 | Steiger |
| 4,465,482 A | 8/1984 | Tittel |
| 4,490,138 A | 12/1984 | Lipsky et al. |
| 4,493,696 A | 1/1985 | Uldall |
| RE31,873 E | 4/1985 | Howes |
| 4,531,933 A | 7/1985 | Norton et al. |
| 4,543,087 A | 9/1985 | Sommercorn et al. |
| 4,545,373 A | 10/1985 | Christoudias |
| 4,549,879 A | 10/1985 | Groshong et al. |
| 4,557,261 A | 12/1985 | Ru/gheimer |
| 4,568,329 A | 2/1986 | Mahurkar |
| 4,568,338 A | 2/1986 | Todd |
| 4,573,476 A | 3/1986 | Ruiz |
| 4,581,012 A | 4/1986 | Brown et al. |
| 4,583,968 A | 4/1986 | Mahurkar |
| 4,583,986 A | 4/1986 | Lapidus |
| 4,601,697 A | 7/1986 | Mammolenti et al. |
| 4,619,643 A | 10/1986 | Bai |
| 4,623,327 A | 11/1986 | Mahurkar |
| 4,626,240 A | 12/1986 | Edelman et al. |
| 4,642,101 A | 2/1987 | Krolikowski et al. |
| 4,643,711 A | 2/1987 | Bates |
| 4,666,426 A | 5/1987 | Aigner |
| 4,668,221 A | 5/1987 | Luther |
| 4,670,009 A | 6/1987 | Bullock |
| 4,675,004 A | 6/1987 | Hadford et al. |
| 4,681,122 A | 7/1987 | Winters et al. |
| 4,681,564 A | 7/1987 | Landreneau |
| 4,681,570 A | 7/1987 | Dalton |
| 4,682,978 A | 7/1987 | Martin |
| 4,687,471 A | 8/1987 | Twardowski et al. |
| 4,692,141 A | 9/1987 | Mahurkar |
| 4,694,838 A | 9/1987 | Wijayarthna et al. |
| 4,701,159 A | 10/1987 | Brown et al. |
| 4,702,917 A | 10/1987 | Schindler |
| 4,706,671 A | 11/1987 | Weinrib |
| 4,713,171 A | 12/1987 | Polaschegg |
| 4,717,379 A | 1/1988 | Ekholmer |
| 4,735,620 A | 4/1988 | Ruiz |
| 4,737,141 A | 4/1988 | Spits |
| 4,737,152 A | 4/1988 | Alchas |
| 4,738,667 A | 4/1988 | Galloway |
| 4,748,808 A | 6/1988 | Hill |
| 4,755,176 A | 7/1988 | Patel |
| 4,769,016 A | 9/1988 | Labianca |
| 4,770,652 A | 9/1988 | Mahurkar |
| 4,772,268 A | 9/1988 | Bates |
| 4,772,269 A | 9/1988 | Twardowski et al. |
| 4,776,841 A | 10/1988 | Catalano |
| 4,777,951 A | 10/1988 | Cribier et al. |
| 4,784,638 A | 11/1988 | Ghajar et al. |
| 4,790,809 A | 12/1988 | Kuntz |
| 4,795,439 A | 1/1989 | Guest |
| 4,801,297 A | 1/1989 | Mueller |
| D300,060 S | 2/1989 | Molgaard-Nielsen |
| 4,804,359 A | 2/1989 | Grunwald et al. |
| 4,808,155 A | 2/1989 | Mahurkar |
| 4,808,163 A | 2/1989 | Laub |
| 4,809,710 A | 3/1989 | Williamson |
| 4,820,265 A | 4/1989 | DeSatnick et al. |
| 4,832,687 A | 5/1989 | Smith, III |
| 4,834,709 A | 5/1989 | Banning et al. |
| 4,842,582 A | 6/1989 | Mahurkar |
| 4,842,592 A | 6/1989 | Caggiani et al. |
| 4,846,814 A | 7/1989 | Ruiz |
| 4,863,441 A | 9/1989 | Lindsay et al. |
| 4,867,742 A | 9/1989 | Calderon |
| 4,892,518 A | 1/1990 | Cupp et al. |
| 4,894,057 A | 1/1990 | Howes |
| 4,895,561 A | 1/1990 | Mahurkar |
| 4,898,591 A | 2/1990 | Jang et al. |
| 4,906,238 A | 3/1990 | Greenfeld et al. |
| 4,925,452 A | 5/1990 | Melinyshyn et al. |
| 4,927,418 A | 5/1990 | Dake et al. |
| 4,935,004 A | 6/1990 | Cruz |
| 4,935,010 A | 6/1990 | Cox et al. |
| 4,935,044 A | 6/1990 | Schoenpflug |
| 4,936,826 A | 6/1990 | Amarasinghe |
| 4,950,232 A | 8/1990 | Ruzicka et al. |
| 4,950,259 A | 8/1990 | Geary et al. |
| 4,951,665 A | 8/1990 | Schneider |
| 4,961,729 A | 10/1990 | Vaillancourt |
| 4,961,731 A | 10/1990 | Bodicky et al. |
| 4,961,809 A | 10/1990 | Martin |
| 4,968,307 A | 11/1990 | Dake et al. |
| 4,969,890 A | 11/1990 | Sugita et al. |
| 4,981,477 A | 1/1991 | Schon et al. |
| 4,985,014 A | 1/1991 | Orejola |
| 4,990,138 A | 2/1991 | Bacich et al. |
| 4,994,027 A | 2/1991 | Farrell |
| 4,995,865 A | 2/1991 | Gahara et al. |
| 5,009,636 A | 4/1991 | Wortley et al. |
| 5,015,230 A | 5/1991 | Martin et al. |
| 5,016,640 A | 5/1991 | Ruiz |

(56) References Cited

U.S. PATENT DOCUMENTS

| | | |
|---|---|---|
| 5,021,044 A | 6/1991 | Sharkawy |
| 5,041,101 A | 8/1991 | Seder et al. |
| 5,041,107 A | 8/1991 | Heil, Jr. |
| 5,049,138 A | 9/1991 | Chevalier et al. |
| 5,053,003 A | 10/1991 | Dadson et al. |
| 5,053,004 A | 10/1991 | Markel et al. |
| 5,053,023 A | 10/1991 | Martin |
| 5,057,073 A | 10/1991 | Martin |
| 5,059,170 A | 10/1991 | Cameron |
| 5,059,177 A | 10/1991 | Towne et al. |
| 5,069,673 A | 12/1991 | Shwab |
| 5,074,841 A | 12/1991 | Ademovic et al. |
| 5,084,013 A | 1/1992 | Takase |
| 5,098,412 A | 3/1992 | Shiu |
| 5,100,395 A | 3/1992 | Rosenberg |
| 5,102,402 A | 4/1992 | Dror et al. |
| 5,106,368 A | 4/1992 | Uldall et al. |
| 5,106,376 A | 4/1992 | Mononen et al. |
| 5,111,829 A | 5/1992 | Alvarez de Toledo |
| 5,112,301 A | 5/1992 | Fenton, Jr. et al. |
| 5,114,423 A | 5/1992 | Kasprzyk et al. |
| 5,117,836 A | 6/1992 | Millar |
| 5,120,299 A | 6/1992 | Lombardi |
| 5,120,304 A | 6/1992 | Sasaki |
| 5,122,125 A | 6/1992 | Deuss |
| 5,125,888 A | 6/1992 | Howard et al. |
| 5,125,904 A | 6/1992 | Lee |
| 5,129,891 A | 7/1992 | Young |
| 5,135,599 A | 8/1992 | Martin et al. |
| 5,139,486 A | 8/1992 | Moss |
| 5,156,592 A | 10/1992 | Martin et al. |
| 5,163,928 A | 11/1992 | Hobbs et al. |
| 5,167,623 A | 12/1992 | Cianci et al. |
| 5,171,216 A | 12/1992 | Dasse et al. |
| 5,171,227 A | 12/1992 | Twardowski et al. |
| 5,178,616 A | 1/1993 | Uemiya et al. |
| 5,188,592 A | 2/1993 | Hakki |
| 5,188,593 A | 2/1993 | Martin |
| 5,190,520 A | 3/1993 | Fenton, Jr. et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,973 A | 3/1993 | Pang et al. |
| 5,197,976 A | 3/1993 | Herweck et al. |
| 5,201,723 A | 4/1993 | Quinn |
| 5,207,648 A | 5/1993 | Gross |
| 5,207,650 A | 5/1993 | Martin |
| 5,209,723 A | 5/1993 | Twardowski et al. |
| 5,209,725 A | 5/1993 | Roth |
| 5,209,742 A | 5/1993 | Venema et al. |
| 5,215,527 A | 6/1993 | Beck et al. |
| 5,221,255 A | 6/1993 | Mahurkar et al. |
| 5,221,256 A | 6/1993 | Mahurkar |
| 5,222,949 A | 6/1993 | Kaldany |
| 5,226,880 A | 7/1993 | Martin |
| 5,234,438 A | 8/1993 | Semrad |
| 5,236,016 A | 8/1993 | Vogelsang |
| 5,242,398 A | 9/1993 | Knoll et al. |
| 5,246,430 A | 9/1993 | MacFarlane |
| 5,250,034 A | 10/1993 | Appling et al. |
| 5,254,084 A | 10/1993 | Geary |
| 5,273,527 A | 12/1993 | Schatz et al. |
| 5,273,534 A | 12/1993 | Knoepfler |
| 5,279,596 A | 1/1994 | Castaneda et al. |
| 5,279,599 A | 1/1994 | Wilk |
| 5,306,240 A | 4/1994 | Berry |
| 5,312,337 A | 5/1994 | Flaherty et al. |
| 5,312,357 A | 5/1994 | Buijs et al. |
| 5,318,517 A | 6/1994 | Reiman |
| 5,322,519 A | 6/1994 | Ash |
| 5,324,274 A | 6/1994 | Martin |
| 5,330,432 A | 7/1994 | Yoon |
| 5,338,308 A | 8/1994 | Wilk |
| 5,342,295 A | 8/1994 | Imran |
| 5,342,386 A | 8/1994 | Trotta |
| 5,346,471 A | 9/1994 | Raulerson |
| 5,348,536 A | 9/1994 | Young et al. |
| 5,350,358 A | 9/1994 | Martin |
| 5,360,397 A | 11/1994 | Pinchuk |
| 5,360,407 A | 11/1994 | Leonard et al. |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,380,290 A | 1/1995 | Makower et al. |
| 5,382,238 A | 1/1995 | Abrahamson et al. |
| 5,389,087 A | 2/1995 | Miraki |
| 5,389,090 A | 2/1995 | Fischell et al. |
| 5,395,316 A | 3/1995 | Martin |
| 5,399,168 A | 3/1995 | Wadsworth, Jr. et al. |
| 5,403,291 A | 4/1995 | Abrahamson |
| 5,405,320 A | 4/1995 | Twardowski et al. |
| 5,405,341 A | 4/1995 | Martin |
| 5,409,463 A | 4/1995 | Thomas et al. |
| 5,417,668 A | 5/1995 | Setzer et al. |
| 5,423,768 A | 6/1995 | Folden et al. |
| 5,431,661 A | 7/1995 | Koch |
| 5,451,026 A | 9/1995 | Smith |
| 5,451,206 A | 9/1995 | Young |
| 5,451,233 A | 9/1995 | Yock |
| 5,458,570 A | 10/1995 | May, Jr. |
| 5,458,582 A | 10/1995 | Nakao |
| 5,462,533 A | 10/1995 | Daugherty |
| 5,472,417 A | 12/1995 | Martin et al. |
| 5,472,432 A | 12/1995 | Martin |
| 5,476,453 A | 12/1995 | Mehta |
| 5,480,380 A | 1/1996 | Martin |
| 5,486,159 A | 1/1996 | Mahurkar |
| 5,489,278 A | 2/1996 | Abrahamson |
| 5,496,292 A | 3/1996 | Burnham |
| 5,496,872 A | 3/1996 | Constancis et al. |
| 5,505,710 A | 4/1996 | Dorsey, III |
| 5,507,723 A | 4/1996 | Keshaviah |
| 5,509,897 A | 4/1996 | Twardowski et al. |
| 5,509,900 A | 4/1996 | Kirkman |
| 5,509,902 A | 4/1996 | Raulerson |
| 5,542,925 A | 8/1996 | Orth |
| 5,545,373 A | 8/1996 | Maziasz et al. |
| 5,556,390 A | 9/1996 | Hicks |
| 5,556,930 A | 9/1996 | Brehm et al. |
| 5,558,635 A | 9/1996 | Cannon |
| 5,562,609 A | 10/1996 | Brumbach |
| 5,562,696 A | 10/1996 | Nobles et al. |
| 5,569,182 A | 10/1996 | Twardowski et al. |
| 5,569,195 A | 10/1996 | Saab |
| 5,571,093 A | 11/1996 | Cruz et al. |
| 5,584,803 A | 12/1996 | Stevens et al. |
| 5,599,304 A | 2/1997 | Shaari |
| 5,599,328 A | 2/1997 | Stevens |
| 5,607,462 A | 3/1997 | Imran |
| 5,624,392 A | 4/1997 | Saab |
| 5,624,413 A | 4/1997 | Markel et al. |
| 5,632,729 A | 5/1997 | Cai et al. |
| 5,637,102 A | 6/1997 | Tolkoff et al. |
| 5,642,270 A | 6/1997 | Green et al. |
| 5,655,867 A | 8/1997 | Gysi et al. |
| 5,662,606 A | 9/1997 | Cimino et al. |
| 5,665,067 A | 9/1997 | Linder et al. |
| 5,674,237 A | 10/1997 | Ott |
| 5,685,867 A | 11/1997 | Twardowski et al. |
| 5,686,867 A | 11/1997 | Sutardja et al. |
| 5,693,030 A | 12/1997 | Lee et al. |
| 5,695,457 A | 12/1997 | St. Goar et al. |
| 5,704,915 A | 1/1998 | Melsky et al. |
| 5,713,849 A | 2/1998 | Bosma et al. |
| 5,713,853 A | 2/1998 | Clark et al. |
| 5,717,216 A | 2/1998 | McCoy et al. |
| 5,718,678 A | 2/1998 | Fleming, III |
| 5,718,692 A | 2/1998 | Schon et al. |
| 5,720,735 A | 2/1998 | Dorros |
| 5,738,649 A | 4/1998 | Macoviak |
| 5,741,329 A | 4/1998 | Agrawal et al. |
| 5,743,873 A | 4/1998 | Cai et al. |

(56) References Cited

U.S. PATENT DOCUMENTS

| | | |
|---|---|---|
| 5,752,939 A | 5/1998 | Makoto |
| 5,769,796 A | 6/1998 | Palermo et al. |
| 5,772,643 A | 6/1998 | Howell et al. |
| 5,776,096 A | 7/1998 | Fields |
| 5,776,111 A | 7/1998 | Tesio |
| 5,785,686 A | 7/1998 | Runge |
| 5,792,094 A | 8/1998 | Stevens et al. |
| 5,792,123 A | 8/1998 | Ensminger |
| 5,797,869 A | 8/1998 | Martin et al. |
| 5,800,384 A | 9/1998 | Russell et al. |
| 5,800,414 A | 9/1998 | Cazal |
| 5,800,516 A | 9/1998 | Fine et al. |
| 5,807,311 A | 9/1998 | Palestrant |
| 5,807,318 A | 9/1998 | St. Goar et al. |
| 5,807,329 A | 9/1998 | Gelman |
| 5,809,897 A | 9/1998 | Powell et al. |
| 5,810,789 A | 9/1998 | Powers et al. |
| 5,814,016 A | 9/1998 | Valley et al. |
| 5,830,184 A | 11/1998 | Basta |
| 5,830,196 A | 11/1998 | Hicks |
| 5,833,671 A | 11/1998 | Macoviak et al. |
| 5,843,048 A | 12/1998 | Gross |
| 5,858,009 A | 1/1999 | Jonkman |
| 5,861,010 A | 1/1999 | Boussignac et al. |
| 5,868,717 A | 2/1999 | Prosl |
| 5,873,865 A | 2/1999 | Horzewski et al. |
| 5,876,366 A | 3/1999 | Dykstra et al. |
| 5,876,426 A | 3/1999 | Kume et al. |
| 5,882,347 A | 3/1999 | Mouris-Laan et al. |
| 5,891,111 A | 4/1999 | Ismael |
| 5,904,670 A | 5/1999 | Schreiner |
| 5,911,715 A | 6/1999 | Berg et al. |
| 5,913,848 A | 6/1999 | Luther et al. |
| 5,916,208 A | 6/1999 | Luther et al. |
| 5,919,160 A | 7/1999 | Sanfilippo, II |
| 5,944,732 A | 8/1999 | Raulerson et al. |
| 5,947,937 A | 9/1999 | Urrutia et al. |
| 5,947,953 A | 9/1999 | Ash et al. |
| 5,957,879 A | 9/1999 | Roberts et al. |
| 5,957,893 A | 9/1999 | Luther et al. |
| 5,957,912 A | 9/1999 | Heitzmann |
| 5,961,486 A | 10/1999 | Twardowski et al. |
| 5,964,796 A | 10/1999 | Imran |
| 5,976,103 A | 11/1999 | Martin |
| 5,976,120 A | 11/1999 | Chow et al. |
| 5,980,551 A | 11/1999 | Summers et al. |
| 5,984,908 A | 11/1999 | Davis et al. |
| 5,989,206 A | 11/1999 | Prosl et al. |
| 5,989,213 A | 11/1999 | Maginot |
| 6,001,079 A | 12/1999 | Pourchez |
| 6,033,382 A | 3/2000 | Basta |
| 6,036,654 A | 3/2000 | Quinn et al. |
| 6,059,771 A | 5/2000 | Balbierz et al. |
| 6,074,374 A | 6/2000 | Fulton |
| 6,086,555 A | 7/2000 | Eliasen et al. |
| 6,086,557 A | 7/2000 | Morejohn et al. |
| 6,090,096 A | 7/2000 | St. Goar et al. |
| 6,099,513 A | 8/2000 | Spehalski |
| 6,103,778 A | 8/2000 | Hyon et al. |
| 6,106,540 A | 8/2000 | White et al. |
| 6,113,572 A | 9/2000 | Gailey et al. |
| 6,117,117 A | 9/2000 | Mauch |
| 6,120,494 A | 9/2000 | Jonkman |
| 6,126,631 A | 10/2000 | Loggie |
| 6,132,425 A | 10/2000 | Gough |
| 6,143,013 A | 11/2000 | Samson et al. |
| 6,146,354 A | 11/2000 | Beil |
| 6,146,373 A | 11/2000 | Cragg et al. |
| 6,152,909 A | 11/2000 | Bagaoisan et al. |
| 6,156,016 A | 12/2000 | Maginot |
| 6,161,547 A | 12/2000 | Barbut |
| 6,178,356 B1 | 1/2001 | Chastain et al. |
| 6,180,059 B1 | 1/2001 | Divino, Jr. et al. |
| 6,190,349 B1 | 2/2001 | Ash et al. |
| 6,190,371 B1 | 2/2001 | Maginot et al. |
| 6,193,685 B1 | 2/2001 | Goodin |
| 6,196,996 B1 | 3/2001 | Teirstein |
| 6,206,849 B1 | 3/2001 | Martin et al. |
| 6,210,365 B1 | 4/2001 | Afzal |
| 6,210,380 B1 | 4/2001 | Mauch |
| 6,217,527 B1 | 4/2001 | Selmon et al. |
| 6,224,622 B1 | 5/2001 | Kotzev |
| 6,238,406 B1 | 5/2001 | Ellis et al. |
| 6,264,627 B1 | 7/2001 | Liska et al. |
| 6,273,879 B1 | 8/2001 | Keith et al. |
| 6,280,413 B1 | 8/2001 | Clark et al. |
| 6,280,423 B1 | 8/2001 | Davey et al. |
| 6,287,326 B1 | 9/2001 | Pecor |
| 6,293,927 B1 | 9/2001 | McGuckin, Jr. |
| 6,293,958 B1 | 9/2001 | Berry et al. |
| 6,296,631 B2 | 10/2001 | Chow |
| 6,299,631 B1 | 10/2001 | Shalaby |
| 6,322,551 B1 | 11/2001 | Brugger |
| 6,328,730 B1 | 12/2001 | Harkrider, Jr. |
| 6,342,120 B1 | 1/2002 | Basta |
| 6,361,529 B1 | 3/2002 | Goodin et al. |
| 6,383,172 B1 | 5/2002 | Barbut |
| 6,394,141 B2 | 5/2002 | Wages et al. |
| 6,394,142 B1 | 5/2002 | Woelfel et al. |
| 6,409,700 B1 | 6/2002 | Siegel, Jr. et al. |
| 6,413,228 B1 | 7/2002 | Hung et al. |
| 6,428,513 B1 | 8/2002 | Abrahamson |
| 6,443,922 B1 | 9/2002 | Roberts et al. |
| 6,450,988 B1 | 9/2002 | Bradshaw |
| 6,453,185 B1 | 9/2002 | O'Keefe |
| 6,454,997 B1 | 9/2002 | Divino, Jr. et al. |
| 6,455,608 B1 | 9/2002 | Jia et al. |
| 6,463,335 B1 | 10/2002 | Munch et al. |
| 6,468,287 B1 | 10/2002 | Baugh |
| 6,473,633 B1 | 10/2002 | Heil, Jr. et al. |
| 6,475,207 B1 | 11/2002 | Maginot et al. |
| 6,475,209 B1 | 11/2002 | Larson et al. |
| 6,478,789 B1 | 11/2002 | Spehalski et al. |
| 6,482,169 B1 | 11/2002 | Kuhle |
| 6,533,763 B1 | 3/2003 | Schneiter |
| 6,565,594 B1 | 5/2003 | Herweck et al. |
| 6,576,001 B2 | 6/2003 | Werneth et al. |
| 6,582,459 B1 | 6/2003 | Lau et al. |
| 6,585,705 B1 | 7/2003 | Maginot et al. |
| 6,592,565 B2 | 7/2003 | Twardowski |
| 6,595,966 B2 | 7/2003 | Davey et al. |
| 6,620,118 B1 | 9/2003 | Prosl et al. |
| 6,638,242 B2 | 10/2003 | Wilson et al. |
| 6,659,134 B2 | 12/2003 | Navis |
| 6,682,498 B2 | 1/2004 | Ross |
| 6,682,519 B1 | 1/2004 | Schon |
| 6,691,625 B2 | 2/2004 | Duncan |
| 6,695,832 B2 | 2/2004 | Schon et al. |
| 6,702,776 B2 | 3/2004 | Quinn |
| 6,712,797 B1 | 3/2004 | Southern, Jr. |
| 6,712,798 B2 | 3/2004 | Constantz |
| 6,719,717 B1 | 4/2004 | Johnson et al. |
| 6,719,749 B1 | 4/2004 | Schweikert et al. |
| 6,723,084 B1 | 4/2004 | Maginot et al. |
| 6,723,114 B2 | 4/2004 | Shalaby |
| 6,730,299 B1 | 5/2004 | Tayot et al. |
| 6,752,827 B2 | 6/2004 | Ross et al. |
| 6,755,851 B2 | 6/2004 | Noda et al. |
| 6,758,836 B2 | 7/2004 | Zawacki |
| 6,786,664 B2 | 9/2004 | Claramunt et al. |
| 6,786,884 B1 | 9/2004 | DeCant, Jr. et al. |
| 6,796,991 B2 | 9/2004 | Nardeo |
| 6,797,107 B1 | 9/2004 | Kotzey |
| 6,808,510 B1 | 10/2004 | DiFiore |
| 6,814,718 B2 | 11/2004 | McGuckin, Jr. et al. |
| 6,819,951 B2 | 11/2004 | Patel et al. |
| 6,821,287 B1 | 11/2004 | Jang |
| 6,824,554 B1 | 11/2004 | Jang |
| 6,835,452 B1 | 12/2004 | Hamerski |
| 6,837,864 B1 | 1/2005 | Bertolero et al. |
| 6,852,079 B2 | 2/2005 | Miyano |
| 6,852,097 B2 | 2/2005 | Fulton, III |
| 6,858,019 B2 | 2/2005 | McGuckin, Jr. et al. |
| 6,872,198 B1 | 3/2005 | Wilson et al. |

(56) References Cited

U.S. PATENT DOCUMENTS

| | | |
|---|---|---|
| 6,878,143 B2 | 4/2005 | Andersen |
| 6,881,211 B2 | 4/2005 | Schweikert et al. |
| 6,884,253 B1 | 4/2005 | McFarlane |
| 6,911,014 B2 | 6/2005 | Wentling et al. |
| 6,913,601 B2 | 7/2005 | St. Goar et al. |
| 6,916,313 B2 | 7/2005 | Cunningham |
| 6,921,396 B1 | 7/2005 | Wilson et al. |
| 6,921,411 B2 | 7/2005 | Yock |
| 6,934,142 B2 | 8/2005 | Grosse et al. |
| 6,966,886 B2 | 11/2005 | Appling |
| 6,969,381 B2 | 11/2005 | Voorhees |
| 6,979,318 B1 | 12/2005 | McDonald et al. |
| 6,991,625 B1 | 1/2006 | Gately et al. |
| D515,211 S | 2/2006 | Chesnin |
| 6,997,894 B2 | 2/2006 | Caresio |
| 7,008,395 B1 | 3/2006 | Loggie |
| 7,011,645 B2 | 3/2006 | McGuckin, Jr. et al. |
| 7,018,384 B2 | 3/2006 | Skakoon |
| 7,029,467 B2 | 4/2006 | Currier et al. |
| 7,066,914 B2 | 6/2006 | Andersen |
| 7,066,925 B2 | 6/2006 | Gately et al. |
| 7,074,213 B2 | 7/2006 | McGuckin, Jr. et al. |
| 7,077,829 B2 | 7/2006 | McGuckin, Jr. et al. |
| 7,087,053 B2 | 8/2006 | Vanney |
| 7,090,654 B2 | 8/2006 | Lotito et al. |
| 7,108,674 B2 | 9/2006 | Quinn |
| D530,420 S | 10/2006 | Chesnin |
| 7,128,734 B1 | 10/2006 | Wilson et al. |
| 7,130,700 B2 | 10/2006 | Gardeski et al. |
| 7,141,035 B2 | 11/2006 | Haggstrom |
| RE39,451 E | 12/2006 | Kuhle |
| 7,182,746 B2 | 2/2007 | Haarala et al. |
| 7,300,430 B2 | 11/2007 | Wilson et al. |
| 7,322,953 B2 | 1/2008 | Redinger |
| 7,347,852 B2 | 3/2008 | Hobbs et al. |
| 7,381,204 B2 | 6/2008 | Wilson et al. |
| 7,393,339 B2 | 7/2008 | Zawacki et al. |
| 7,422,571 B2 | 9/2008 | Schweikert et al. |
| 7,465,286 B2 | 12/2008 | Patterson et al. |
| 7,485,107 B2 | 2/2009 | DiFiore et al. |
| 7,569,029 B2 | 8/2009 | Clark |
| 7,575,563 B2 | 8/2009 | Appling |
| 7,651,482 B2 | 1/2010 | Harris |
| 7,686,823 B2 | 3/2010 | Pingleton et al. |
| 7,798,999 B2 | 9/2010 | Bailey et al. |
| 7,972,465 B2 | 7/2011 | Patterson et al. |
| 8,021,321 B2 | 9/2011 | Zawacki |
| 8,066,660 B2 | 11/2011 | Gregersen et al. |
| 8,092,415 B2 | 1/2012 | Moehle et al. |
| 8,100,863 B2 | 1/2012 | Moehle et al. |
| 8,152,951 B2 | 4/2012 | Zawacki et al. |
| 8,206,371 B2 | 6/2012 | Nimkar et al. |
| 8,292,841 B2 | 10/2012 | Gregersen |
| 8,500,939 B2 | 8/2013 | Nimkar et al. |
| 8,540,661 B2 | 9/2013 | Gregersen |
| 8,597,275 B2 | 12/2013 | Nimkar et al. |
| 8,696,614 B2 | 4/2014 | Gregersen et al. |
| 8,808,227 B2 | 8/2014 | Zawacki et al. |
| 8,894,601 B2 | 11/2014 | Moehle et al. |
| 8,992,454 B2 | 3/2015 | Anand |
| 9,174,019 B2 | 11/2015 | Gregersen |
| 9,233,200 B2 | 1/2016 | Gregersen et al. |
| 9,572,956 B2 | 2/2017 | Nimkar et al. |
| 9,579,485 B2 | 2/2017 | Oborn et al. |
| 9,610,422 B2 | 4/2017 | Moehle et al. |
| 9,669,149 B2 | 6/2017 | Anand |
| 9,782,535 B2 | 10/2017 | Anand |
| 10,105,514 B2 | 10/2018 | Nimkar et al. |
| 10,207,043 B2 | 2/2019 | Gregersen |
| 10,258,732 B2 | 4/2019 | Gregersen et al. |
| 10,258,768 B2 | 4/2019 | Loesener et al. |
| 10,518,064 B2 | 12/2019 | Oborn et al. |
| 2001/0041857 A1 | 11/2001 | Sansoucy |
| 2001/0041873 A1 | 11/2001 | Dopper et al. |
| 2002/0013569 A1 | 1/2002 | Sterman et al. |
| 2002/0026156 A1 | 2/2002 | Quinn |
| 2002/0055724 A1 | 5/2002 | Hughes |
| 2002/0086047 A1 | 7/2002 | Mueller et al. |
| 2002/0087108 A1 | 7/2002 | Maginot et al. |
| 2002/0087145 A1 | 7/2002 | Ehwald et al. |
| 2002/0091362 A1 | 7/2002 | Maginot et al. |
| 2002/0091430 A1 | 7/2002 | Dobak et al. |
| 2002/0099326 A1 | 7/2002 | Wilson et al. |
| 2002/0099327 A1 | 7/2002 | Wilson et al. |
| 2002/0107506 A1 | 8/2002 | McGuckin et al. |
| 2002/0138031 A1 | 9/2002 | Ross |
| 2002/0169490 A1 | 11/2002 | Noda et al. |
| 2002/0173770 A1 | 11/2002 | Flory et al. |
| 2002/0177904 A1 | 11/2002 | Huxel et al. |
| 2003/0023198 A1 | 1/2003 | Twardowski |
| 2003/0032734 A1 | 2/2003 | Roby |
| 2003/0088213 A1 | 5/2003 | Schweikert et al. |
| 2003/0093027 A1 | 5/2003 | McGuckin et al. |
| 2003/0097091 A1 | 5/2003 | Hobbs et al. |
| 2003/0135147 A1 | 7/2003 | Rosenberg et al. |
| 2003/0144623 A1 | 7/2003 | Heath et al. |
| 2003/0149395 A1 | 8/2003 | Zawacki |
| 2003/0153898 A1 | 8/2003 | Schon et al. |
| 2003/0163145 A1 | 8/2003 | Raulerson |
| 2003/0187411 A1 | 10/2003 | Constantz |
| 2003/0204179 A1 | 10/2003 | Davey et al. |
| 2004/0039350 A1 | 2/2004 | McKittrick |
| 2004/0054321 A1 | 3/2004 | Schon et al. |
| 2004/0059314 A1 | 3/2004 | Schon et al. |
| 2004/0064086 A1 | 4/2004 | Gottlieb et al. |
| 2004/0065333 A1 | 4/2004 | Wilson et al. |
| 2004/0075198 A1 | 4/2004 | Schweikert et al. |
| 2004/0087892 A1 | 5/2004 | Cunningham |
| 2004/0092863 A1 | 5/2004 | Raulerson et al. |
| 2004/0097863 A1 | 5/2004 | Appling |
| 2004/0097863 A1 | 5/2004 | Raulerson |
| 2004/0122418 A1 | 6/2004 | Voorhees |
| 2004/0147903 A1 | 7/2004 | Latini |
| 2004/0167463 A1 | 8/2004 | Zawacki et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0193102 A1 | 9/2004 | Haggstrom |
| 2004/0197301 A1 | 10/2004 | Zhao et al. |
| 2004/0210180 A1 | 10/2004 | Altman |
| 2004/0210187 A1 | 10/2004 | Zawacki |
| 2004/0210237 A1 | 10/2004 | Ross et al. |
| 2004/0220550 A1 | 11/2004 | Schryver |
| 2004/0230204 A1 | 11/2004 | Wortley et al. |
| 2004/0243095 A1 | 12/2004 | Nimkar et al. |
| 2004/0249337 A1 | 12/2004 | DiFiore |
| 2005/0003322 A1 | 1/2005 | Logan et al. |
| 2005/0004504 A1 | 1/2005 | Frye et al. |
| 2005/0013341 A1 | 1/2005 | Baghai |
| 2005/0019382 A1 | 1/2005 | Kummer et al. |
| 2005/0025641 A1 | 2/2005 | Shibata et al. |
| 2005/0027282 A1 | 2/2005 | Schweikert et al. |
| 2005/0027289 A1 | 2/2005 | Castellano et al. |
| 2005/0033222 A1 | 2/2005 | Haggstrom et al. |
| 2005/0033264 A1 | 2/2005 | Redinger |
| 2005/0054989 A1 | 3/2005 | McGuckin et al. |
| 2005/0055012 A1 | 3/2005 | Trerotola |
| 2005/0059925 A1 | 3/2005 | Maginot et al. |
| 2005/0070842 A1 | 3/2005 | Lotito et al. |
| 2005/0080398 A1 | 4/2005 | Markel et al. |
| 2005/0085765 A1 | 4/2005 | Voorhees |
| 2005/0096585 A1 | 5/2005 | Schon et al. |
| 2005/0113904 A1 | 5/2005 | Shank et al. |
| 2005/0131341 A1 | 6/2005 | McGuckin et al. |
| 2005/0171469 A1 | 8/2005 | Cunningham |
| 2005/0187535 A1 | 8/2005 | Wilson et al. |
| 2005/0209582 A1 | 9/2005 | Quinn et al. |
| 2005/0215977 A1 | 9/2005 | Uschold |
| 2005/0228339 A1 | 10/2005 | Clark |
| 2005/0245900 A1 | 11/2005 | Ash |
| 2005/0251190 A1 | 11/2005 | McFarlane |
| 2005/0256461 A1 | 11/2005 | DiFiore et al. |
| 2005/0261663 A1 | 11/2005 | Patterson et al. |
| 2005/0267400 A1 | 12/2005 | Haarala et al. |

(56) References Cited

U.S. PATENT DOCUMENTS

| | | |
|---|---|---|
| 2005/0277862 A1 | 12/2005 | Anand |
| 2005/0283111 A1 | 12/2005 | Maurice |
| 2005/0288623 A1 | 12/2005 | Hjalmarsson |
| 2005/0288706 A1 | 12/2005 | Widomski et al. |
| 2006/0004316 A1 | 1/2006 | Difiore et al. |
| 2006/0004325 A1 | 1/2006 | Hamatake et al. |
| 2006/0009783 A1 | 1/2006 | Rome et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0058775 A1 | 3/2006 | Stevens et al. |
| 2006/0064072 A1 | 3/2006 | Gately et al. |
| 2006/0095062 A1 | 5/2006 | Stephens |
| 2006/0100572 A1 | 5/2006 | DiMatteo et al. |
| 2006/0111537 A1 | 5/2006 | Roby |
| 2006/0116629 A1 | 6/2006 | Tal et al. |
| 2006/0161100 A1 | 7/2006 | Hamboly |
| 2006/0184142 A1 | 8/2006 | Schon et al. |
| 2006/0189922 A1 | 8/2006 | Amarasinghe et al. |
| 2006/0200111 A1 | 9/2006 | Moehle et al. |
| 2006/0206094 A1 | 9/2006 | Chesnin et al. |
| 2006/0251612 A1 | 11/2006 | Kotzev et al. |
| 2006/0253063 A1 | 11/2006 | Schweikert |
| 2006/0271012 A1 | 11/2006 | Canaud et al. |
| 2007/0005003 A1 | 1/2007 | Patterson et al. |
| 2007/0019181 A1 | 1/2007 | Sinclair et al. |
| 2007/0066964 A1 | 3/2007 | Atkins |
| 2007/0078478 A1 | 4/2007 | Atkins et al. |
| 2007/0106206 A1 | 5/2007 | Appling |
| 2007/0129704 A1 | 6/2007 | O'Mahony et al. |
| 2007/0167925 A1 | 7/2007 | Jacqmein |
| 2007/0191810 A1 | 8/2007 | Kennedy |
| 2007/0225661 A1 | 9/2007 | Ash et al. |
| 2007/0225682 A1 | 9/2007 | Ash et al. |
| 2007/0282274 A1 | 12/2007 | Chesnin |
| 2008/0021417 A1 | 1/2008 | Zawacki et al. |
| 2008/0039774 A1 | 2/2008 | Zawacki et al. |
| 2008/0065029 A1 | 3/2008 | Racz |
| 2008/0082079 A1 | 4/2008 | Braga et al. |
| 2008/0082080 A1 | 4/2008 | Braga |
| 2008/0097409 A1 | 4/2008 | Stephens |
| 2008/0172012 A1 | 7/2008 | Hiniduma-Lokuge et al. |
| 2008/0214980 A1 | 9/2008 | Anand |
| 2008/0214992 A1 | 9/2008 | Haarala et al. |
| 2009/0112153 A1 | 4/2009 | Gregersen et al. |
| 2009/0118661 A1 | 5/2009 | Moehle et al. |
| 2009/0118701 A1 | 5/2009 | Nimkar et al. |
| 2009/0118707 A1 | 5/2009 | Schweikert et al. |
| 2009/0118755 A1 | 5/2009 | Maliglowka et al. |
| 2009/0138034 A1 | 5/2009 | Maliglowka et al. |
| 2009/0157051 A1 | 6/2009 | Appling et al. |
| 2009/0187141 A1 | 7/2009 | Lareau et al. |
| 2009/0192435 A1 | 7/2009 | Gregersen |
| 2009/0204052 A1 | 8/2009 | Nimkar et al. |
| 2009/0204079 A1 | 8/2009 | Nimkar et al. |
| 2009/0204083 A1* | 8/2009 | O'Donnell ............ A61F 2/954 604/284 |
| 2009/0205189 A1 | 8/2009 | Nimkar et al. |
| 2009/0209940 A1 | 8/2009 | Nimkar et al. |
| 2009/0292248 A1 | 11/2009 | Schon et al. |
| 2009/0312687 A1 | 12/2009 | DeFonzo et al. |
| 2010/0081986 A1 | 4/2010 | Matson et al. |
| 2010/0331780 A1 | 12/2010 | Bellisario et al. |
| 2011/0020418 A1 | 1/2011 | Bosley, Jr. et al. |
| 2011/0301522 A1 | 12/2011 | DeFonzo |
| 2012/0059304 A1 | 3/2012 | Gregersen et al. |
| 2012/0089070 A1 | 4/2012 | Moehle et al. |
| 2013/0018405 A1 | 1/2013 | Onishi et al. |
| 2013/0079752 A1 | 3/2013 | Gregersen |
| 2013/0253445 A1 | 9/2013 | Nimkar et al. |
| 2013/0261605 A1 | 10/2013 | Gregersen et al. |
| 2014/0018772 A1 | 1/2014 | Ash |
| 2014/0025042 A1 | 1/2014 | Gregersen |
| 2014/0088510 A1 | 3/2014 | Nimkar et al. |
| 2014/0228742 A1 | 8/2014 | Gregersen et al. |
| 2014/0276472 A1 | 9/2014 | VanderStek et al. |
| 2014/0276493 A1 | 9/2014 | Leung et al. |
| 2014/0277052 A1 | 9/2014 | Haselby et al. |
| 2014/0330220 A1 | 11/2014 | Zawacki et al. |
| 2014/0336687 A1 | 11/2014 | Iwase et al. |
| 2015/0073336 A1 | 3/2015 | Moehle et al. |
| 2015/0088100 A1 | 3/2015 | Oborn et al. |
| 2015/0335810 A1 | 11/2015 | Anand |
| 2017/0151418 A1 | 6/2017 | Nimkar et al. |
| 2017/0165453 A1 | 6/2017 | Oborn et al. |
| 2019/0167888 A1 | 6/2019 | Gregersen |
| 2019/0240393 A1 | 8/2019 | Gregersen et al. |
| 2020/0129729 A1 | 4/2020 | Oborn et al. |

FOREIGN PATENT DOCUMENTS

| | | |
|---|---|---|
| CA | 2474351 A1 | 8/2003 |
| CN | 2788836 Y | 6/2006 |
| CN | 101918067 A | 12/2010 |
| CN | 103170050 A | 6/2013 |
| CN | 101918066 B | 7/2013 |
| DE | 8815869 U1 | 2/1989 |
| DE | 9108132 U1 | 9/1991 |
| DE | 102005051211 A1 | 5/2007 |
| EP | 0030854 A2 | 6/1981 |
| EP | 0132344 A2 | 1/1985 |
| EP | 0301854 A | 2/1989 |
| EP | 0332366 A2 | 9/1989 |
| EP | 0386408 A1 | 9/1990 |
| EP | 0453234 A1 | 10/1991 |
| EP | 0476796 A1 | 3/1992 |
| EP | 0495263 A1 | 7/1992 |
| EP | 0650740 A1 | 5/1995 |
| EP | 0711574 A1 | 5/1996 |
| EP | 1471966 A1 | 11/2004 |
| EP | 1599247 A2 | 11/2005 |
| EP | 2305337 A2 | 4/2011 |
| GB | 1503469 A | 3/1978 |
| JP | 56-136569 A | 10/1981 |
| JP | 8-510935 T | 11/1996 |
| JP | 2001137350 A | 5/2001 |
| JP | 2008500081 A | 1/2008 |
| JP | 2011-502583 A | 1/2011 |
| JP | 4827377 B2 | 11/2011 |
| RU | 45923 U1 | 6/2005 |
| SU | 459237 A1 | 2/1975 |
| WO | 1991008132 A1 | 6/1991 |
| WO | 1993016741 A1 | 9/1993 |
| WO | 1993016752 A1 | 9/1993 |
| WO | 1997009086 A1 | 3/1997 |
| WO | 1997017102 | 5/1997 |
| WO | 1997022374 A1 | 6/1997 |
| WO | 1997037699 | 10/1997 |
| WO | 1999004844 A1 | 2/1999 |
| WO | 2000023137 A1 | 4/2000 |
| WO | 2002018004 A2 | 3/2002 |
| WO | 2002058776 A2 | 8/2002 |
| WO | 2002083223 A1 | 10/2002 |
| WO | 2003030960 A2 | 4/2003 |
| WO | 2003033049 A2 | 4/2003 |
| WO | 2003066148 A1 | 8/2003 |
| WO | 2004075962 A2 | 9/2004 |
| WO | 2004096334 A1 | 11/2004 |
| WO | 2004112876 A1 | 12/2004 |
| WO | 2005018712 A2 | 3/2005 |
| WO | 2005023336 A2 | 3/2005 |
| WO | 2005077449 A1 | 8/2005 |
| WO | 2005084741 A1 | 9/2005 |
| WO | 2005118039 A1 | 12/2005 |
| WO | 2006034877 A1 | 4/2006 |
| WO | 2008048183 A1 | 4/2008 |
| WO | 2009051967 A1 | 4/2009 |
| WO | 2009055332 A1 | 4/2009 |
| WO | 2009059220 A1 | 5/2009 |

(56) References Cited

FOREIGN PATENT DOCUMENTS

| | | |
|---|---|---|
| WO | 2015077560 A1 | 5/2015 |
| WO | 2016/011091 A1 | 1/2016 |

OTHER PUBLICATIONS

U.S. Appl. No. 10/445,731, filed May 27, 2003 Non-Final Office Action dated Apr. 13, 2007.
U.S. Appl. No. 10/445,731, filed May 27, 2003 Non-Final Office Action dated Dec. 12, 2008.
U.S. Appl. No. 10/445,731, filed May 27, 2003 Non-Final Office Action dated May 30, 2008.
U.S. Appl. No. 10/842,586, filed May 10, 2004 Advisory Action dated Oct. 9, 2008.
U.S. Appl. No. 10/842,586, filed May 10, 2004 Final Office Action dated Jul. 29, 2008.
U.S. Appl. No. 10/842,586, filed May 10, 2004 Final Office Action dated May 25, 2010.
U.S. Appl. No. 10/842,586, filed May 10, 2004 Non-Final Office Action dated Jan. 7, 2008.
U.S. Appl. No. 10/842,586, filed May 10, 2004 Non-Final Office Action dated Jun. 16, 2009.
U.S. Appl. No. 10/842,586, filed May 10, 2004 Non-Final Office Action dated Nov. 13, 2008.
U.S. Appl. No. 10/842,586, filed May 10, 2004 Non-Final Office Action dated Nov. 23, 2009.
U.S. Appl. No. 10/874,298, filed Jun. 9, 2004 Advisory Action dated Feb. 19, 2009.
U.S. Appl. No. 10/874,298, filed Jun. 9, 2004 Final Office Action dated Jul. 15, 2008.
U.S. Appl. No. 10/874,298, filed Jun. 9, 2004 Final Office Action dated Jul. 7, 2010.
U.S. Appl. No. 10/874,298, filed Jun. 9, 2004 Final Office Action dated Mar. 18, 2014.
U.S. Appl. No. 10/874,298, filed Jun. 9, 2004 Non-Final Office Action dated Aug. 1, 2013.
U.S. Appl. No. 10/874,298, filed Jun. 9, 2004 Non-Final Office Action dated Aug. 18, 2011.
U.S. Appl. No. 10/874,298, filed Jun. 9, 2004 Non-Final Office Action dated Dec. 30, 2009.
U.S. Appl. No. 10/874,298, filed Jun. 9, 2004 Non-Final Office Action dated Feb. 2, 2011.
U.S. Appl. No. 10/874,298, filed Jun. 9, 2004 Non-Final Office Action dated Jul. 23, 2009.
U.S. Appl. No. 10/874,298, filed Jun. 9, 2004 Non-Final Office Action dated Jul. 9, 2014.
U.S. Appl. No. 10/874,298, filed Jun. 9, 2004 Non-Final Office Action dated May 23, 2006.
U.S. Appl. No. 10/874,298, filed Jun. 9, 2004 Non-Final Office Action dated May 24, 2007.
U.S. Appl. No. 11/859,106, filed Sep. 21, 2007 Final Office Action dated Sep. 1, 2009.
U.S. Appl. No. 11/859,106, filed Sep. 21, 2007 Non-Final Office Action dated Feb. 5, 2009.
U.S. Appl. No. 11/859,106, filed Sep. 21, 2007 Non-Final Office Action dated Mar. 30, 2011.
U.S. Appl. No. 11/859,106, filed Sep. 21, 2007 Non-Final Office Action dated Jun. 25, 2008.
U.S. Appl. No. 11/874,447, filed Oct. 18, 2007 Decision on Appeal dated Dec. 26, 2012.
U.S. Appl. No. 11/874,447, filed Oct. 18, 2007 Examiner's Answer dated Apr. 28, 2010.
U.S. Appl. No. 11/874,447, filed Oct. 18, 2007 Final Office Action dated Jul. 22, 2009.
U.S. Appl. No. 11/874,447, filed Oct. 18, 2007 Non-Final Office Action dated Jan. 6, 2009.
U.S. Appl. No. 11/874,447, filed Oct. 18, 2007 Non-Final Office Action dated Jul. 12, 2013.
U.S. Appl. No. 11/874,447, filed Oct. 18, 2007 Non-Final Office Action dated Jul. 9, 2008.
U.S. Appl. No. 11/874,447, filed Oct. 18, 2007 Notice of Allowance dated Apr. 18, 2014.
U.S. Appl. No. 12/048,871, filed Mar. 14, 2008 Decision on Appeal dated Feb. 2, 2015.
U.S. Appl. No. 12/048,871, filed Mar. 14, 2008 Examiner's Answer dated Feb. 9, 2012.
U.S. Appl. No. 12/048,871, filed Mar. 14, 2008 Final Office Action dated Jan. 20, 2011.
U.S. Appl. No. 12/048,871, filed Mar. 14, 2008 Final Office Action dated Jan. 4, 2016.
U.S. Appl. No. 12/048,871, filed Mar. 14, 2008 Non-Final Office Action dated Aug. 31, 2016.
U.S. Appl. No. 12/048,871, filed Mar. 14, 2008 Non-Final Office Action dated Jan. 7, 2010.
U.S. Appl. No. 12/048,871, filed Mar. 14, 2008 Non-Final Office Action dated Jul. 16, 2015.
U.S. Appl. No. 12/048,871, filed Mar. 14, 2008 Non-Final Office Action dated Jul. 7, 2010.
U.S. Appl. No. 12/048,871, filed Mar. 14, 2008 Non-Final Office Action dated May 12, 2009.
U.S. Appl. No. 12/048,871, filed Mar. 14, 2008 Notice of Allowance dated Feb. 10, 2017.
U.S. Appl. No. 12/244,514, filed Oct. 2, 2008 Final Office Action dated Jun. 19, 2012.
U.S. Appl. No. 12/244,514, filed Oct. 2, 2008 Non-Final Office Action dated Jan. 17, 2012.
U.S. Appl. No. 12/244,559, filed Oct. 2, 2008 Decision on Appeal dated Aug. 31, 2015.
U.S. Appl. No. 12/244,559, filed Oct. 2, 2008 Examiner's Answer dated Mar. 27, 2013.
U.S. Appl. No. 12/244,559, filed Oct. 2, 2009 Final Office Action dated Jul. 3, 2012.
U.S. Appl. No. 12/244,559, filed Oct. 2, 2009 Non-Final Office Action dated Mar. 14, 2012.
U.S. Appl. No. 12/244,514, filed Oct. 2, 2008 Advisory Action dated Sep. 5, 2012.
U.S. Appl. No. 12/244,514, filed Oct. 2, 2008 Final Office Action dated Jul. 11, 2011.
U.S. Appl. No. 12/244,514, filed Oct. 2, 2008 Non-Final Office Action dated Jan. 19, 2011.
U.S. Appl. No. 12/244,544, filed Oct. 2, 2008 Final Office Action dated Jul. 11, 2011.
U.S. Appl. No. 12/244,544, filed Oct. 2, 2008 Non-Final Office Action dated Dec. 22, 2010.
U.S. Appl. No. 12/244,554, filed Oct. 2, 2008 Final Office Action dated Dec. 27, 2010.
U.S. Appl. No. 12/244,554, filed Oct. 2, 2008 Non-Final Office Action dated Jul. 6, 2010.
U.S. Appl. No. 12/253,870, filed Oct. 17, 2008 Non-Final Office Action dated Jan. 21, 2011.
U.S. Appl. No. 12/253,870, filed Oct. 17, 2008 Notice of Allowance dated Aug. 19, 2011.
U.S. Appl. No. 12/262,820, filed Oct. 31, 2008 Non-Final Office Action dated Feb. 18, 2011.
U.S. Appl. No. 12/262,820, filed Oct. 31, 2008 Notice of Allowance dated Sep. 28, 2011.
U.S. Appl. No. 12/263,141, filed Oct. 31, 2008 Advisory Action dated Aug. 17, 2011.
U.S. Appl. No. 12/263,141, filed Oct. 31, 2008 Final Office Action dated May 26, 2011.
U.S. Appl. No. 12/263,141, filed Oct. 31, 2008 Non-Final Office Action dated Jan. 5, 2011.
U.S. Appl. No. 12/414,467, filed Mar. 30, 2009 Final Office Action dated Feb. 7, 2012.
U.S. Appl. No. 12/414,467, filed Mar. 30, 2009 Notice of Allowance dated May 31, 2012.
U.S. Appl. No. 12/414,467, filed Mar. 30, 2009 Non-Final Office Action dated Aug. 11, 2011.
U.S. Appl. No. 13/294,941, filed Nov. 11, 2011 Non-Final Office Action dated May 27, 2016.

(56) References Cited

OTHER PUBLICATIONS

U.S. Appl. No. 13/294,941, filed Nov. 11, 2011 Non-Final Office Action dated May 31, 2013.
U.S. Appl. No. 13/294,941, filed Nov. 11, 2011 Notice of Allowance dated Nov. 27, 2013.
U.S. Appl. No. 13/329,156, filed Dec. 16, 2011 Non-Final Office Action dated May 16, 2014.
U.S. Appl. No. 13/445,713, filed Apr. 12, 2012 Advisory Action dated Aug. 8, 2013.
U.S. Appl. No. 13/445,713, filed Apr. 12, 2012 Final Office Action dated May 30, 2013.
U.S. Appl. No. 13/445,713, filed Apr. 12, 2012 Non-Final Office Action dated Jan. 2, 2013.
U.S. Appl. No. 13/445,713, filed Apr. 12, 2012 Notice of Allowance dated Oct. 18, 2013.
U.S. Appl. No. 13/897,292, filed May 17, 2013 Decision on Appeal dated Jun. 8, 2017.
U.S. Appl. No. 13/897,292, filed May 17, 2013 Final Office Action dated Apr. 9, 2015.
U.S. Appl. No. 13/897,292, filed May 17, 2013 Non-Final Office Action dated Nov. 20, 2014.
U.S. Appl. No. 13/897,292, filed May 17, 2013 Notice of Allowance dated Aug. 23, 2017.
U.S. Appl. No. 14/032,858, filed Sep. 20, 2013 Final Office Action dated Mar. 31, 2015.
U.S. Appl. No. 14/032,858, filed Sep. 20, 2013 Non-Final Office Action dated Nov. 4, 2014.
U.S. Appl. No. 14/032,858, filed Sep. 20, 2013, Notice of Allowance dated Jun. 26, 2015.
U.S. Appl. No. 14/094,534, filed Dec. 2, 2013 Final Office Action dated Jul. 20, 2016.
U.S. Appl. No. 14/094,534, filed Dec. 2, 2013 Non-Final Office Action dated Feb. 24, 2016.
U.S. Appl. No. 14/094,534, filed Dec. 2, 2013 Notice of Allowance dated Sep. 30, 2016.
U.S. Appl. No. 14/252,567, filed Apr. 14, 2014 Non-Final Office Action dated Mar. 31, 2015.
U.S. Appl. No. 14/252,567, filed Apr. 14, 2014 Notice of Allowance dated Sep. 3, 2015.
U.S. Appl. No. 14/328,541, filed Jul. 10, 2014 Final Office Action dated Oct. 22, 2015.
U.S. Appl. No. 14/328,541, filed Jul. 10, 2014 Non-Final Office Action dated Apr. 9, 2015.
U.S. Appl. No. 14/542,495, filed Nov. 14, 2014 Final Office Action dated Aug. 31, 2016.
U.S. Appl. No. 14/542,495, filed Nov. 14, 2014 Non-Final Office Action dated May 10, 2016.
U.S. Appl. No. 14/542,495, filed Nov. 14, 2014 Notice of Allowance dated Nov. 15, 2016.
U.S. Appl. No. 14/675,236, filed Mar. 31, 2015 Non-Final Office Action dated Feb. 2, 2017.
U.S. Appl. No. 14/675,236, filed Mar. 31, 2015 Notice of Allowance dated May 16, 2017.
U.S. Appl. No. 14/799,547, filed Jul. 14, 2015 Non-Final Office Action dated Mar. 16, 2017.
U.S. Appl. No. 14/799,547, filed Jul. 14, 2015 Restriction Requirement dated Nov. 30, 2017.
U.S. Appl. No. 14/930,526, filed Nov. 2, 2015 Final Office Action dated Jun. 7, 2018.
U.S. Appl. No. 14/930,526, filed Nov. 2, 2015 Non-Final Office Action dated Feb. 23, 2016.
U.S. Appl. No. 14/930,526, filed Nov. 2, 2015 Notice of Allowance dated Oct. 2, 2018.
Arrow Cannon II Plus Brochure, 2006.
*Arrow International, Inc. et al v. Spire Biomedical, Inc.*, U.S. Dist Ct Dist MA CA No. 06-CV-11564-DPW, Declaration of Dr. Karim Valji (Jul. 17, 2008).
*Arrow International, Inc. et al v. Spire Biomedical, Inc.*, U.S. Dist Ct Dist MA CA No. 06-CV-11564-DPW, Declaration of Kenneth Todd Cassidy (Jul. 16, 2008).
*Arrow International, Inc. et al v. Spire Biomedical, Inc.*, U.S. Dist Ct Dist MA CA No. 06-CV-11564-DPW, Declaration of Rebecca R. Eisenberg in Opposition to Defendant's Motion for Partial Summary Judgment of Invalidity (Jun. 8, 2009).
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity [Redacted Pursuant to Jun. 10, 2008 Order on Motion to Seal].
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity Exhibit A (Jul. 10, 2009).
*Arrow International, Inc. et al v. Spire Biomedical, Inc.*, U.S. Dist Ct Dist MA CA No. 06-CV-11564-DPW, Plaintiff's Memorandum in Opposition to Defendant's Motion for Summary Judgement on Non-Infringement (Jul. 17, 2008).
*Arrow International, Inc. et al. v. Spire Biomedical, Inc.*, U.S. Dist. Ct. Dist. MA CA No. 06-CV-11564-DPW, Defendant's Omnibus Statement of Material Facts in Support of its Motions for Summary Judgment (Jun. 10, 2008) [Redacted Pursuant to Jun. 10, 2008 Order on Motion to Seal].
Bander, et al., Central Venous Angioaccess for Hemodialysis and Its Complications, Seminars in Dialysis, 1992, vol. 5, No. 2, pp. 121-128.
Baranowski, L., Central Venous Access Devices, Journal of Intravenous Nursing, 1993, vol. 16, No. 3, pp. 167-194.
Bard Access Systems Hickman®, Leonard®, and Broviac® Central Venous Catheters (Long Term), Instructions for Use, 31 pages, 1999.
Bard Access Systems Hickman®, Leonard®, and Broviac® Central Venous Catheters, Nursing Procedural Manual, 52 pages, Jun. 1994.
Bard Davol® Hickman® Round Dual Lumen Catheters for Central Venous Access Informational Brochure, 4 pages, 1994.
Bard Hickman® Catheters Informational Brochure, 3 pages, 1994.
Believed to be an unpublished sketch of a conception by Dr. John Frusha; date of sketch believed to be Jun. 24, 1997.
Berkoben, et al., Maintenance of Permanent Hemodialysis Vascular Access Patency, ANNA Journal, 1995, vol. 22, No. 1, pp. 17-24.
Bolz, et al., Catheter Malfunction and Thrombus Formation on Double-Lumen Hemodialysis Catheters: An Intravascular Ultrasonographic Study, American Journal of Kidney Diseases, 1995, vol. 25, No. 4, pp. 597-602.
Bour, et al., Experience With the Double Lumen Silastic® Catheter for Hemoaccess, Surgery, Gynecology & Obstetrics, 1990, vol. 171, pp. 33-39.
Camp, "Care of the Groshong Catheter", Oncol Nurs Forum, vol. 15, No. 6, 1988.
Campbell, et al., Radiological Insertion of Long-term Venous Access Devices, Seminars in Interventional Radiology, 1994, vol. II, No. 4, pp. 366-375.
Canaud, B et al, Permenant Twin Catheter: A Vascular Access Option of Choice for Haemodialysis in Elderly Patients, pp. 82-88, vol. 17 No. 7, 1994.
Claim Construction Order of Federal District Court dated May 9, 2003 in *Thierry Pourchez and Bard Access Systems, Inc. v. Diatek, Inc. and Arrow International, Inc.* litigation (S.D. N.Y. 03 Civ. 0972).
Claim Construction Order of Federal District Court dated Oct. 31, 2006 in *Arrow Int'l. Investment Corp. v. Spire Biomedical, Inc.* litigation (D. Mass. Civil Action No. 06-CV-11564).
CN 200880121182.0 filed Oct. 20, 2008 First Office Action dated May 2, 2012.
CN 200880121183.5 filed Oct. 2, 2008 First Office Action dated Mar. 28, 2012.
CN 200880121183.5 filed Oct. 2, 2008 Second Office Action dated Aug. 17, 2012.
CN 200880121183.5 filed Oct. 2, 2008 Third Office Action dated Dec. 11, 2012.
CN 200880123095.9 filed Oct. 20, 2008 First Office Action dated Feb. 13, 2012.
CN 200880123095.9 filed Oct. 20, 2008 Second Office Action dated Dec. 18, 2012.

(56) References Cited

OTHER PUBLICATIONS

CN 200880123533.1 filed Jun. 30, 2008 First Office Action dated May 28, 2012.
CN 200880123533.1 filed Jun. 30, 2008 Notice of Grant dated Dec. 24, 2012.
CN 201310073124.8 filed Mar. 7, 2013 First Office Action dated May 5, 2014.
Decision of Federal District Court dated Jul. 7, 2009 granting Summary Judgement of Invalidity in Arrow Int'l. Inc.and Arrow Int'l. Investment Corp. v. Spire Biomedical, Inc. litigation (D. Mass. Civil Action No. 06-CV-11564).
Declaration of Gregory S. Haas (Plaintiff's Exhibit 88 in Haas Deposition), Mar. 13, 2003, Thierry Pourchez and Bard Access Systems, Inc. v. Diatek, Inc. and Arrow International, Inc., Civil Action No. 03-CV-0972 (S.D.N.Y.).
Defendant's Exhibits DX78-DX114, Thierry Pourchez and Bard Access Systems, Inc. v. Diatek, Inc. and Arrow International, Inc., Civil Action No. 03-CV-0972 (S.D.N.Y.), 2003.
Defendants' Reponses and Objections to Plaintiffs' Second Set of Interrogatories (Excerpt), Thierry Pourchez and Bard Access Systems, Inc. v. Diatek, Inc. and Arrow International, Inc., Civil Action No. 03-CV-0972 (S.D.N.Y.) (Oct. 8, 2003).
Delmore et al., "Experience with the Groshong Long-Term Central Venous Catheter", Gynecologic Oncology 34, 216-218 (1989).
Dialysis Vascular Access, SchonXL® Temporary Dialysis (AngioDynamics Inc.) brochure, Nov. 1998.
Dialysis Vascular Access, Technological Innovations Improving Flow (AngioDynamics Inc.) Brochure, 4 pages, Nov. 1998.
DiFiore, "Central Venous Dialysis Catheter Evaluatio in Swine", Journal of Vascular Access Devices, Fall 2000.
Donaldson, et al., Peripherally Inserted Central Venous Catheters: US-guided Vascular Access in Pediatric Patients1, Radiology, 1995, vol. 197, pp. 542-544.
Dunea, et al., A Survey of Permanent Double Lumen Catheters in Hemodialysis Patients. ASAIO Transac. 1991; 37: M276-7.
Dupont et al, Long-term development of Permacath Quinton catheters used as a vascular access route for extra-renal detoxification; Néphrologie, vol. 15, pp. 105-110, 1994.
EP 04712925.9 filed Feb. 19, 2004 Office Action dated Nov. 7, 2008.
EP 08839196.6 filed Oct. 2, 2008 Examination Report dated Jan. 16, 2013.
EP 08839196.6 filed Oct. 2, 2008 Search Opinion dated Jul. 12, 2011.
EP 08839196.6 filed Oct. 2, 2008 Search Report dated Jul. 12, 2011.
EP 08872340.8 filed Oct. 2, 2008 Extended European Search Report and an Opinion dated Apr. 19, 2012.
EP 14864273.9 filed May 20, 2016 Extended European Search Report dated Jun. 9, 2017.
EP 14864273.9 filed May 20, 2016 Partial European Search Report dated Jun. 9, 2017.
Gallichio, et al., Placement of a Double Lumen Silastic Catheter for Hemodialysis Access Through the Cephalic Vein, Journal of the American College of Surgeons, 1994, vol. 179, pp. 171-172.
Gravenstein, et al., In Vitro Evaluation of Relative Perforating Potential of Central Venous Catheters: Comparison of Materials, Selected Models, Number of Lumens, and Angles of Incidence to Simulated Membrane, Journal of Clinical Monitoring, 1991, vol. 7, pp. 1-6.
Haindl, H., Technical complications of port-catheter systems, Reg. Cancer Treat, 1989, 2:238-242.
Haire, et al., Thrombotic Complications of Subclavian Apheresis catheters in Cancer Patients: Prevention With Heparin Infusion, Journal of Clinical Apheresis, 1990, vol. 5, pp. 188-191.
Hull, et al., The Groshong Catheter: Initial Experience and Early Results of Imaging-guided Placement1, Radiology, 1992, vol. 185, pp. 803-807.
Ignotus, et al., Review of Radiological Insertion of Indwelling Central Venous Catheters, Minimally Invasive Therapy, 1992, 1:373-388.

Instructions for Use (Copyright Dated 1990) for Polycath Polyurethance Central Venous Catheter; believed to have been packaged with product and sold in the United States before Jan. 4, 2000 and with related marketing materials.
Instructions for Use (Copyright Dated 1992) for FloLock Single Lumen Bi-directional Valved Catheter; believed to have been packaged with product and sold in the United States before Jan. 2000.
Instructions for Use (not dated) for Infuse-a-Cath Polyurethance Central Venous Catheter; believed to have been packaged with product and sold in the United States before Jan. 2000.
Instructions for Use for Diatek Cannon Catheter Product First Sold in the United States in Sep. 2001.
Jones, et al., Efficacy of the Supraclavicular Route for Temporary Hemodialysis Access, Southern Medical Journal, 1992, vol. 85, No. 7, pp. 725-726.
JP 2010-532299 filed Apr. 30, 2010 Final Notice of Reason for Rejection dated Feb. 8, 2013.
JP 2010-532299 filed Apr. 30, 2010 Official Action dated Apr. 23, 2012.
JP 2016-533038 filed May 20, 2016 Office Action dated Oct. 11, 2018.
JP App. No. 2003-565569 filed Feb. 7, 2003, Translated Decision of Refusal dated Dec. 24, 2009.
JP App. No. 2003-565569 filed Feb. 7, 2003, Translated Official Action dated May 28, 2009.
JP App. No. 2003-565569 filed Feb. 7, 2003, Translated Official Action dated Nov. 7, 2008.
Kapoian et al. Dialysis as Treatment of End-Stage Renal Disease, Chapter 5: Dialysis Access and Recirculation, © 1999.
Kaupke, et al., Perforation of the Superior Vena Cava by a Subclavian Hemodialysis Catheter: early detection by angiography, The International Journal of Artificial Organs, 1992, vol. 15, No. 11, pp. 666-668.
Kelber, et al., Factors Affecting Delivery of High-Efficiency Dialysis Using Temporary Vascular Access, American Journal of Kidney Diseases, 1993, vol. 22, No. 1, pp. 24-29.
Lubrizol, "Lubrizol's Family of TPUs" Brochure (2005), 9 pages.
Lumsden, et al., Hemodialysis Access in the Pediatric Patient Population, The American Journal of Surgery, 1994, vol. 168, pp. 197.
Lund, "Percutaneous Translumbar Inferior Vena Cava Cannulation and other Alternative Vascular Access Techniques" in Venous Interventional Radiology with Clinical Perspectives, Savader et al, eds. pp. 251-261, Apr. 10, 2000.
Lund, et al., Percutaneous Translumbar Inferior Vena Cava Cannulation for Hemodialysis, American Journal of Kidney Diseases, 1995, vol. 25, No. 5, pp. 732-737.
Maki, D., Pathogenesis, Prevention, and Management of Infections Due to Intravascular Devices Used for Infusion Therapy, in Infections Associated with Indwelling Medical Devices, Bisno et al, eds, American Society for Microbiology, 1989, pp. 161-177.
Malviya et al., "Vascular Access in Gynecological Cancer Using the Groshong Right Atrial Catheter", Gynecological Oncology 33, 313-316 (1989).
Mauro, et al., Radiologic Placement of Long-term Central Venous Catheters: A Review, JVIR, 1993, vol. 4, No. 1, pp. 127-137.
McGee, et al., Accurate placement of central venous catheters: A prospective, randomized, multicenter trial, Critical Care Medicine, 1993, vol. 21, No. 8, pp. 1118-1123.
Medcomp, For Access via the Internal Jugular Vein...The Medcomp TESIO Catheter is the Solution: The Short and Long Term Solution to Subclavian Venin Stenosis and Difficult Access Problems, Brochure, 4 pages, 1991.
Medcomp® Brochure , "Ash Split Cath™ XL", Dec. 2001, PN 2291.
Medcomp® Brochure , "Ash Split Cath™", Guidewire Weave Insertion Technique, Jan. 2002, PN 2296.
Medcomp® Brochure , "Ash Split Cath™", Jul. 2001, PN 2114.
Medcomp® Brochure , "Ash Split Cath™", Nov. 1997, PN 2050.
Medcomp® Brochure , "Ash Split Cath® II ", Aug. 2002, PN 2334.
Medcomp® Brochure , "Magna™ High Flow Catheter", Mar. 2002, PN 2321.

(56) References Cited

OTHER PUBLICATIONS

Moss et al, Use of Silicone Dual-Lumen Catheter with a Dacron Cuff as a Long Term Vascular Access for Hemodialysis Patients, Amer J Kidney Diseases, vol. XVI, No. 3, pp. 211-215, Sep. 1990.
Moss, et al., Use of a Silicone Catheter With a Dacron Cuff for Dialysis Short-Term Vascular Access, American Journal of Kidney Diseases, 1988, vol. XII, No. 6, pp. 492-498.
Myers, R.D. et al, New Double-lumen Polyethylene Cannula for Push-pull Perfusion of Brain Tissue in Vivo, Journal of Neuroscience Methods, pp. 205-218, vol. 12, 1985.
Northsea, C., Using Urokinase to Restore Patency in Double Lumen Catheters, ANNA Journal 1994, vol. 21, No. 5, pp. 261-273.
OriGen, OriGen Biomedical Dual Lumen Catheter, from <http://origen.net/catheter.html>, downloaded May 13, 2009, 4 pages (reprinted for submission on Jul. 21, 2011).
Parsa, et al., Establishment of Intravenous Lines for Long-term Intravenous Therapy and Monitoring, Surgical Clinics of N. Am. 1985, vol. 65, No. 4, pp. 835-865.
Parsa, et al., Vascular Access Techniques, Textbook of Critical Care, W.B. Saunders, Philadelphia, PA (1989), pp. 122-127.
Pasquale, et al., Groshong® Versus Hickman® Catheters, Surgery, Gynecology & Obstetrics, 1992, vol. 174, pp. 408-410.
Passaro, et al., Long-term Silastic Catheters and Chest Pain, Journal of Parenteral and Enteral Nutrition, 1994, vol. 18, No. 3, pp. 240-242.
Patel et al., "Sheathless Technique of Ash Split-Cath Insertion", 12 JVIR 376-78 (Mar. 2001).
Paulsen, et al., Use of Tissue Plasminogen Activator for Reopening of Clotted Dialysis Catheters, Nephron, 1993, vol. 64, pp. 468-470.
PCT/US15/40463 filed Jul. 14, 2015 International Search Report and Written Opinion dated Dec. 18, 2015.
PCT/US2003/003751 filed Feb. 7, 2003 Preliminary Examination Report dated May 5, 2004.
PCT/US2003/003751 filed Feb. 7, 2003 Search Report dated Jul. 3, 2003.
PCT/US2004/005102 filed Feb. 19, 2004 Preliminary Report Patenability dated Aug. 29, 2005.
PCT/US2004/005102 filed Feb. 19, 2004 Search Report dated Dec. 27, 2004.
PCT/US2004/005102 filed Feb. 19, 2004 Written Opinion dated Aug. 21, 2005.
PCT/US2008/078551 filed Oct. 2, 2008 International Preliminary Report on Patentability dated Apr. 20, 2010.
PCT/US2008/078551 filed Oct. 2, 2008 Search Report dated Mar. 13, 2009.
PCT/US2008/078551 filed Oct. 2, 2008 Written Opinion dated Mar. 13, 2009.
PCT/US2008/078560 filed Oct. 2, 2008 Preliminary Report on Patentability dated Aug. 26, 2010.
PCT/US2008/078560 filed Oct. 2, 2008 Search Report dated Mar. 16, 2009.
PCT/US2008/078560 filed Oct. 2, 2008 Written Opinion dated Mar. 16, 2009.
PCT/US2008/078566 filed Oct. 2, 2008 International Preliminary Report on Patentability dated Apr. 20, 2010.
PCT/US2008/078566 filed Oct. 2, 2008 Search Report dated Mar. 19, 2009.
PCT/US2008/078566 filed Oct. 2, 2008 Written Opinion dated Mar. 19, 2009.
PCT/US2008/078571 filed Oct. 2, 2008 Preliminary Report on Patentability dated Aug. 26, 2010.
PCT/US2008/078571 filed Oct. 2, 2008 Search Report dated Mar. 20, 2009.
PCT/US2008/078571 filed Oct. 2, 2008 Written Opinion dated Mar. 20, 2009.
PCT/US2008/080463 filed Oct. 20, 2008 Preliminary Report on Patentability dated Apr. 27, 2010.
PCT/US2008/080463 filed Oct. 20, 2008 Search Report dated Mar. 16, 2009.
PCT/US2008/080463 filed Oct. 20, 2008 Written Opinion dated Apr. 16, 2009.
PCT/US2008/082106 filed Oct. 31, 2008 International Preliminary Report on Patentability dated May 4, 2010.
PCT/US2008/082106 filed Oct. 31, 2008 Search Report dated Jan. 12, 2009.
PCT/US2008/082106 filed Oct. 31, 2008 Written Opinion dated Jan. 12, 2009.
PCT/US2014/066811 filed Nov. 21, 2014 International Search Report and Written Opinion dated Apr. 15, 2015.
Picture of Device believed to be partial sample of a product believed to have been sold in the United States with Polycath and/or Infuse-a-Cath Instructions for Use, 1 page, 2011.
QUINTON® Catheter Products (1993).
Raaf Dual Lumen Right Atrial Catheters Brochure—Quinton Instrument Co., 6 pages, 1993.
Raaf, et al., Open Insertion of Right Atrial Catheters Through the Jugular Veins, Surgery, Gynecology & Obstetrics, 1993, vol. 177, pp. 295-298.
Rawn, et al., The Hemodialysis Access, Chapter 9, pp. 9.1-9.11, available at «http://msl1.mit.edu/ESD10/kidneys/HndbkPDF/Chap09.pdf», last accessed Jun. 4, 2012.
Schwab, et al., Prospective Evaluation of a Dacron Cuffed Hemodialysis Catheter for Prolonged Use, American Journal of Kidney Diseases, 1988, vol. XI, No. 2, pp. 166-169.
Schwab, et al., Vascular Access: Case Oriented Discussions of Selected Critical Issues: Hemodialysis Catheters for Permanent Use, 1999.
Septum, Wikipedia, The Free Encyclopedia, hhtp://en.wikipedia.org/wiki/Septum (last visited Dec. 18, 2012) (defining "septum" as "a wall, dividing a cavity or structure into smaller ones").
Shaffer, D., Catheter-Related Sepsis Complicating Long-Term Tunnelled Central Venous Dialysis Catheters: Management by Guidewire Exchange, American Journal of Kidney Diseases, 1995, vol. 25, No. 4, pp. 593-596.
Shaffer, D., Lessons From Vascular Access Procedures for Hemodialysis, Surgical Oncology Clinics of North America, 1995, vol. 4, No. 3, pp. 537-549.
Sioshansi, P., New Processes for Surface Treatment of Catheters, Artificial Organs, 1994, 18(4):266-271.
Swartz, et al., Successful Use of Cuffed Centrol Venous Hemodialysis Catheters Inserted Percutaneously, J. Am. Soc. Nephrol., 1994, 4:1719-1725.
Taber's Cyclopedic Medical Dictionary 1662 (16th ed. 1989) (defining "septum" as a "wall dividing two cavities").
Tal, Michael G, Comparison of Recirculation Percentage of the Palindrome Catheter and Standard Hemodialysis Catheters in a Swine Model, J Vasc Intery Radiol, pp. 1237-1240, vol. 16, No. 9, 2005.
Tesio, et al., Double Catheterization of the Internal Jugular Vein for Hemodialysis: Indications, Techniques, and Clinical Results, Artificial Organs, 1994, vol. 18, No. 4, pp. 301-304.
The Groshong™ Peripherally Inserted Central Venous Catheter Brochure—Cath-tech®, 4 pages, 1988.
Transcript of Videotaped Deposition of Gregory Haas (Excerpt), Sep. 23, 2003, *Thierry Pourchez and Bard Access Systems, Inc.* v. *Diatek, Inc. and Arrow International, Inc.*, Civil Action No. 03-CV-0972 (S.D.N.Y.).
Transcript of Videotaped Deposition of Thierry Pourchez, vol. 1, Oct. 16, 2003, *Thierry Pourchez and Bard Access Systems, Inc.* v. *Diatek, Inc. and Arrow International, Inc.*, Civil Action No. 03-CV-0972 (S.D.N.Y.).
Transcript of Videotaped Deposition of Thierry Pourchez, vol. 2, Oct. 17, 2003, *Thierry Pourchez and Bard Access Systems, Inc.* v. *Diatek, Inc. and Arrow International, Inc.*, Civil Action No. 03-CV-0972 (S.D.N.Y.).
Treiman, et al., Chronic Venous Access in Patients with Cancer, Cancer, 1993, vol. 72, No. 3, pp. 760-765.
Twardowski et al. "Side Holes at the Tip of Chronic Hemodialysis Catehters are Harmful," The Journal of Vascular Access 2001; 2:8-16.
Twardowski et al., "Blood Recirculation in Intravenous Catheters for Hemodialysis" J. Am. Soc. Nephrol. 3:1978-81 (1993).

(56) References Cited

OTHER PUBLICATIONS

Tyco Healthcare, Mahurkar Dual Lumen Catheters, Informational Brochure, 2 pages, 2004.
Tyco Healthcare, Mahurkar QPlus High Flow Acute Care Catheter, Informational Brochure, 2 pages, 2004.
Tyco Healthcare, Tal PALINDROME™ Dual Lumen Catheters Order Information, Features and Benefits, Frequently Asked Questions, printed from http://www.kendallvasculartherapy.com/VascularTherapy, 6 pages, on Mar. 1, 2007.
Uldall, P., Subclavian Cannulation Is No Longer Necessary or Justified in Patients with End-Stage Renal Failure, Seminars in Dialysis, 1994, vol. 7, No. 3, pp. 161-164.
U.S. Appl. No. 10/371,774, filed Feb. 21, 2003 Final Office Action dated Jan. 19, 2007.
U.S. Appl. No. 10/371,774, filed Feb. 21, 2003 Final Office Action dated Mar. 7, 2007.
U.S. Appl. No. 10/371,774, filed Feb. 21, 2003 Non-Final Office Action dated Jul. 17, 2006.
U.S. Appl. No. 15/442,608, filed Feb. 24, 2017 Non-Final Office Action dated May 9, 2019.
U.S. Appl. No. 15/442,608, filed Feb. 24, 2017 Notice of Allowance dated Aug. 27, 2019.
U.S. Appl. No. 16/163,372, filed Oct. 17, 2018 Non-Final Office Action dated May 14, 2020.
U.S. Appl. No. 14/991,858, filed Jan. 8, 2016 Non-Final Office Action dated May 17, 2018.
U.S. Appl. No. 14/991,858, filed Jan. 8, 2016 Notice of Allowance dated Nov. 26, 2018.
U.S. Appl. No. 15/429,049, filed Feb. 9, 2017 Non-Final Office Action dated Mar. 20, 2018.
U.S. Appl. No. 15/429,049, filed Feb. 9, 2017 Notice of Allowance dated May 31, 2018.
US Patent File History U.S. Pat. No. 5,403,291 (Abrahamson), issued Apr. 4, 1995.
US Patent File History U.S. Pat. No. 5,489,278 (Abrahamson), issued Feb. 6, 1996.
US Patent File History U.S. Pat. No. 5,685,867 (Twardowski et al.), issued Nov. 11, 1997.
Wechsler, et al., Thrombosis and Infection Caused by Thoracic Venous Catheters: Pathogenesis and Imagings Findings, AJR, 1993; 160:467-471.
Weitzel, et al., Successful Use of Indwelling Cuffed Femoral Vein Catheters in Ambulatory Hemodialysis Patients, American Journal of Kidney Diseases, 1993, vol. 22, No. 3, pp. 426-429.

\* cited by examiner

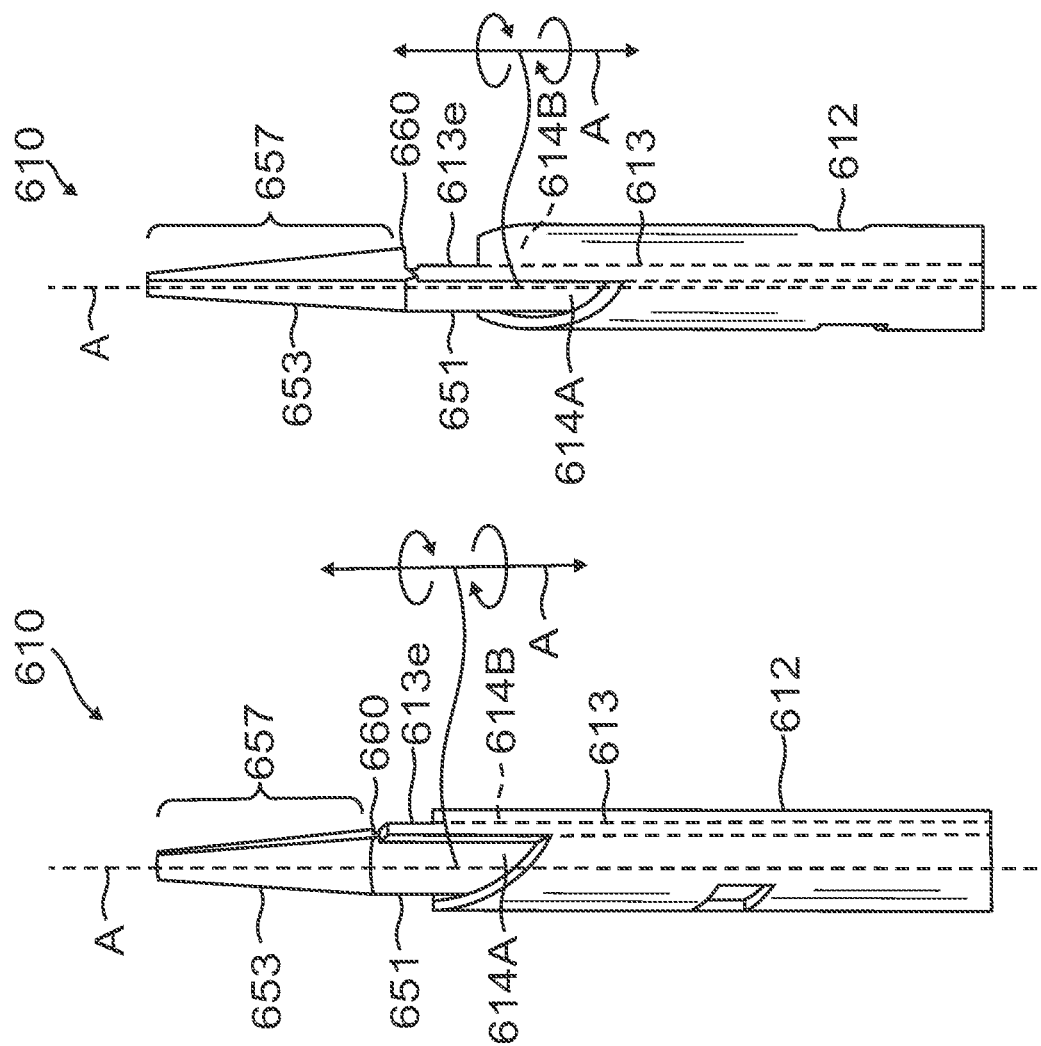

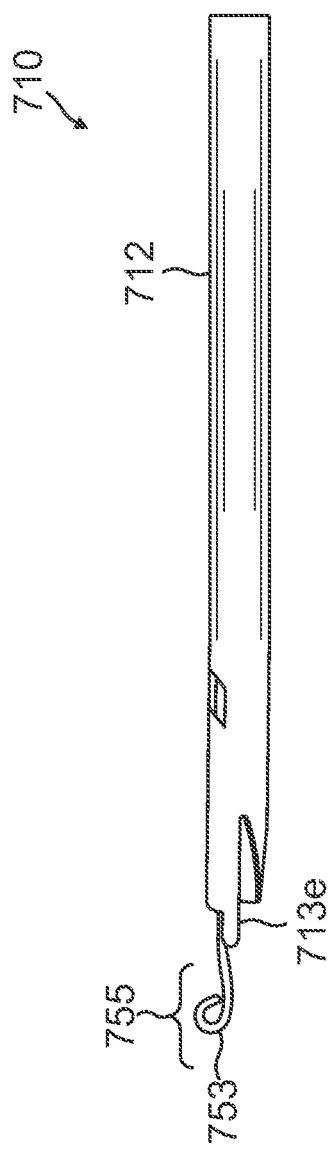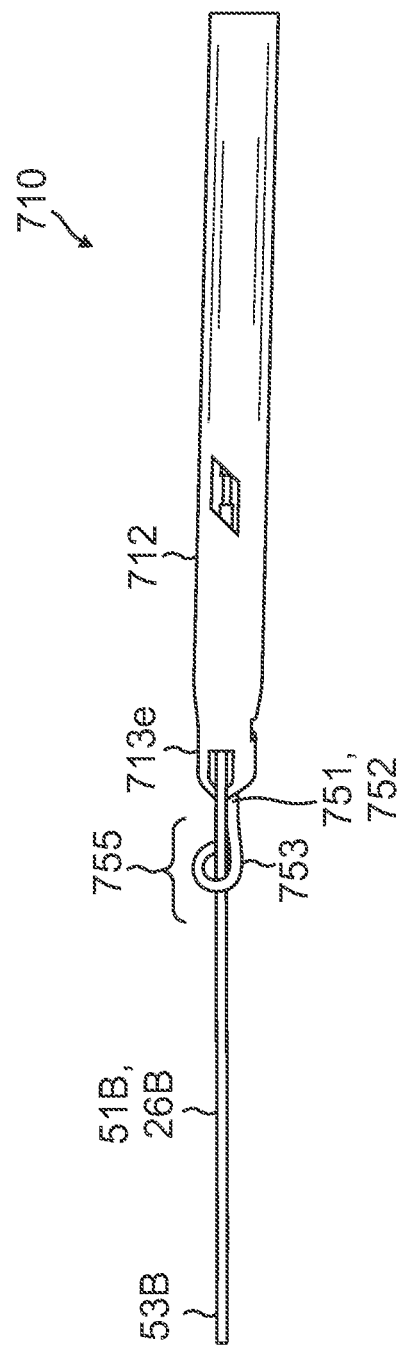

APPARATUSES, SYSTEMS, AND METHODS FOR INSERTING CATHETERS HAVING ENHANCED STIFFENING AND GUIDING FEATURES

PRIORITY

This application is a division of U.S. patent application Ser. No. 14/799,547, filed Jul. 14, 2015, now U.S. Pat. No. 10,258,768, which claims the benefit of priority to U.S. Provisional Application No. 62/024,323, filed Jul. 14, 2014, and to U.S. Provisional Application No. 62/024,423, filed Jul. 14, 2014, each of which is incorporated by reference in its entirety into this application.

BACKGROUND

Related art multi-lumen catheters are desirable for various treatment applications such as hemodialysis where fluid extraction and infusion occur simultaneously. These related art multi-lumen catheters provide a single catheter application having multiple lumen channels, each channel supporting independent flow, thus, precluding the need for inserting multiple catheters or multiple-catheter assemblies. Further, because a patient might require frequent dialysis, often only days apart, securing placement of the catheter for extended periods of time may be required. Extended placement, however, requires extreme catheter flexibility to avoid damage to the blood vessel and to permit the catheter to move in the blood flow in order to minimize the possibility of the catheter remaining in contact with the wall of the vessel for prolonged periods, otherwise causing undue pressure thereon. Related art stylets also have a tendency to snag interior surfaces of a blood vessel, thereby unduly damaging the blood vessel.

An example of a related art multi-lumen catheter includes an elongated tubular body extending to a distal end. The tubular body has a first and a second lumen with a septum disposed therebetween. The tubular body includes a first wall that defines the first lumen and a second wall that defines the second lumen. A portion of the septum extends distally beyond the first lumen and the second lumen. The first wall includes a first wall extension that extends distally beyond the first lumen and is spaced apart from the portion of the septum. The first wall extension defines a concave surface facing the portion of the septum. Alternatively, the catheter includes a tip with spiraled configuration. The catheter may also include a third lumen.

Another example of a related art multi-lumen catheter includes a tubular body having a proximal end and a distal end. The body includes a first lumen and a second lumen with a septum disposed therebetween. The proximal end includes a valve and a hub that are integral with the body. The hub includes a first conduit and a second conduit. The valve includes a first port and a second port that are rotatable, about a longitudinal axis of the body, to establish fluid communication between the lumens and the conduits. The distal end of the tubular body is configured for insertion. The conduits are connectable to a medical apparatus.

Yet another example of a related art multi-lumen catheter includes an elongated tubular body extending to a distal end. The tubular body has a first and a second lumen with a septum disposed therebetween and has a first wall that defines the first lumen and a second wall that defines the second lumen. A portion of the septum extends distally beyond the first lumen and the second lumen. The first wall includes a first wall extension that extends distally beyond the first lumen and is spaced apart from the portion of the septum. The first wall extension defines a concave surface facing the portion of the septum. Alternatively, the septum has a septum extension that extends distally beyond the first lumen and the second lumen; and the septum extension defines a first planar surface and an opposing second planar surface.

Unfortunately, these related art catheters introduce insertion difficulties, including a relative inflexibility thereof. For example, simply advancing the catheter over a guide-wire is very difficult in the related art, since the catheter has a tendency to buckle during disposition through the blood vessel wall as well as during further disposition into the blood vessel to the desired location. Flexible catheters present additional difficulties associated with subcutaneous tunneling and placement. Related art insertion methods and assemblies attempt to overcome, or at least mitigate, these insertion difficulties by temporarily stiffening the catheter during the insertion process.

For example, one related art method involves temporarily inserting a rigid tubular applicator into one of the lumens. This permits the stiffened catheter/applicator assembly to be passed over a guide-wire into a desired position, at which point the applicator can be removed. For example, U.S. Pat. No. 5,405,341 attempts to solve the problem with a single rigid applicator that is designed for insertion into one lumen but also passes through a portion of the second lumen (at the distal end of the instrument) to effectively stiffen the two lumens of the catheter together during insertion. This related art approach is cumbersome, at best, and presents additional difficulties in maneuvering the instrument. Further, this temporary rigid applicator approach is poorly suited for placement of a catheter having a split at its distal end into two or more separate lumens, e.g., to further isolate a fluid extraction lumen from a return infusion lumen, because only one tip can be secured. Hence, a need exists for better and more effective apparatuses, systems, and methods for inserting flexible catheters into blood vessels.

SUMMARY

The present disclosure addresses at least the foregoing needs and provides apparatuses, systems, such as kits, and methods for inserting flexible, multi-lumen catheters into blood vessels, and in particular, for inserting flexible, split-tip catheters into blood vessels. These objects can be accomplished, for example, by temporarily stiffening each catheter lumen and tip independently through use of intra-catheter stiffener elements disposed within the catheter lumens. The apparatuses, systems (such as kits), and methods described herein facilitate advancing the assembly of catheter and stiffeners through a subcutaneous tunnel, and over a plurality of guide-wires until a distal portion of the catheter is disposed at a desired position within the blood vessel.

The intra-catheter stiffener elements, such as the presently disclosed enhanced stylets, are sufficiently stiff to allow advancing the catheter over guide-wires, but also sufficiently flexible to allow bending and looping of the catheter for proper placement within the vessel. Further, the intra-catheter stiffener elements prevent catheter kinking during the insertion process. In one embodiment, the intra-catheter stiffener elements have tapered distal ends which can facilitate entry of the catheter/stiffeners assembly into a blood vessel and/or assist in dilating the blood vessel.

One aspect of the present disclosure provides apparatuses, systems, such as kits, and methods for inserting an antegrade tunneled, split-tip, hemodialysis catheter into a blood vessel.

A distal portion of each of a plurality of guide-wires is disposed in a blood vessel at a first location, generally in proximity to the vessel in which a portion of the catheter, e.g., a catheter body, is to be placed. A subcutaneous tunnel is formed between the first location and a second location where a proximal end of the catheter can extend from the patient. An intra-catheter stiffener element is inserted into the proximal end of each catheter lumen until the intra-catheter stiffener element extends beyond the distal end of that catheter lumen. The intra-catheter stiffener element can be releasably coupled, following insertion, to the proximal end of its respective catheter lumen via, for example, a mating luer assembly. Each guide-wire can be inserted into a distal end of a lumen in a respective intra-catheter stiffener element until that guide-wire extends from the proximal end of that intra-catheter stiffener element. The catheter can then be advanced over the guide-wires and into the blood vessel. Alternatively, the catheter can be advanced over the guide-wires until a distal end of the catheter is adjacent to the vessel, at which point the catheter and guide-wires can be advanced together into the vessel until the distal end of the catheter is at a desired location therein. Twisting the catheter while simultaneously advancing the catheter along the guide-wires can facilitate placement of the catheter into the vessel.

In another aspect, the apparatuses, systems, such as kits, and methods of the present disclosure provide for inserting a retrograde tunneled hemodialysis catheter into a blood vessel. A distal portion of each of a plurality of guide-wires is inserted into a blood vessel at a first location generally as described above. An intra-catheter stiffener element is placed in each catheter lumen until it extends from a distal end of the catheter, and can be releasably connected to the proximal end of its respective catheter lumen, as noted above. A proximal end of each guide-wire is threaded through the distal end of a lumen of each intra-catheter stiffener element until the guide-wire extends beyond the proximal end of that stiffener element. The catheter is advanced over the guide-wires, optionally using a twisting motion, until a distal portion of the catheter is disposed at a desired location within the vessel, or alternatively, the catheter can be advanced until its distal end is adjacent to the vessel, at which point the catheter and guide-wires can be advanced together until the distal end of the catheter is disposed at a desired location within the vessel. The guide-wires are removed from the catheter lumens. A subcutaneous tunnel is then formed between the first location and a second location, and the proximal end of the catheter is passed through the first location until it extends from the second location. (If the stiffener elements have not previously been removed, they can be removed from the catheter body following passage of the catheter through the tunnel.) An access port is connected to the proximal end of each of the catheter lumens allowing fluid connection with a treatment device, such as a hemodialysis infuser.

In a related aspect, the apparatuses, systems, such as kits, and methods of the present disclosure can provide for dilating the desired vessel subsequent to inserting the distal portion of a first guide-wire. For example, a size 6-French sheath/dilator can be threaded over the first guide-wire. Further guide-wires can then be inserted into the expanded vessel, or through a lumen in the sheath and into the vessel. After placement of the guide-wires into the vessel, the dilator or sheath can be removed.

In a further related aspect, the methods provide for tunneling between the first and second location by using a pointed stylet. A distal end of a pointed stylet can be inserted through the skin at the second location and pushed toward the first location until the distal end extends therefrom. The distal end of the catheter is removably attached to a proximal end of the stylet. The stylet is then pulled from the first location until the distal end of the catheter extends therefrom, to facilitate an antegrade tunneled catheter.

Alternatively, a pointed distal end of a stylet can be inserted through the skin at the first location and pushed until it extends from the second location. The proximal end of the catheter can be removably attached to the proximal end of the stylet. The stylet is then pulled back toward the second location until the proximal end of the catheter extends therefrom. The catheter is then released from the stylet, thus positioning a retrograde tunneled catheter. To facilitate movement of the catheter within the tunnel, the proximal end of the catheter having mating lures or other coupling features can be removed or severed prior to attachment to the stylet. After tunneling the catheter, fluid couplings or other attachments can be disposed to the proximal end of the lumens.

Preferably, the vessel is expanded to accommodate placement of the distal portion of the catheter in the vessel. Vessel dilators of increasing size can be sequentially inserted into the vessel for this purpose. For example, a size 12-French dilator followed by a size 14-French, which is then followed by a size 16-French dilator, can be inserted into the vessel before advancing the catheter along the guide-wires. In other embodiments, fewer (or more) dilators of different sizes can be used. Differing size and number of vessel dilators can be used corresponding to the catheter chosen for the desired application. Use of intra-catheter stiffener elements can preclude use of vessel dilators sized larger that the catheter since the stiffener elements and the catheter itself can provide vessel dilation.

Another aspect of the present disclosure provides for apparatus, in the form of a kit, to insert a multi-lumen catheter into a blood vessel. The kit includes guide-wires each adapted to have a distal portion inserted into a blood vessel. A plurality of intra-catheter stiffener elements preferably having tapered distal ends are also provided, each having a lumen extending along its length sized to accommodate a guide-wire, and each having an outside diameter sized to be slidably disposed within a lumen of the catheter. The intra-catheter stiffener elements can be provided in one or more predetermined lengths corresponding to a length of a catheter and its lumens selected for a particular use, or can be of the same length. Further, the intra-catheter stiffeners can be provided with mating devices, such as lures, disposed at a proximal end correspond with mating connectors disposed at a proximal end of the catheter lumens.

One or more vessel dilators can also be provided in the kit, each corresponding in size to a particular application. For example, a size 6-French sheath/dilator can be provided to dilate the vessel to accommodate a plurality of guide-wires. A size 12-French, 14-French, as well as a size 16-French, dilator can be provided to dilate the vessel to accommodate the distal tip of the catheter.

In addition, rather than two separate stylets, the apparatuses, systems, such as kits, and methods further encompass embodiments including: a plurality of stylets, such as two stylets, joined at a proximal end; a lumen disposed within each stylet of the plurality of stylets, wherein the lumen is sized and shaped to receive a flexible rod capable of expanding the stylet tip to a conical shape, and wherein the conical shape is removed contemporaneously with the flexible rod; and a plurality of stylets, each stylet of the plurality of stylets having a hemispherical tip rather than a taper.

Alternatively, a catheter apparatus includes: a catheter body comprising a first lumen capable of fluid communication via a first distal opening and a second lumen capable of fluid communication via a second distal opening; a first intra-catheter stiffener element configured for disposition through the first lumen such that a distal end thereof is distal in relation to the first distal opening, the first intra-catheter stiffener element comprising one of a guide-wire and a stylet; and a second intra-catheter stiffener element configured for disposition through the second lumen such that a distal end thereof is distal in relation to the second distal opening, the second intra-catheter stiffener element comprising a guide-wire, one of the first intra-catheter stiffener element distal end and the second intra-catheter stiffener element distal end capable of receiving and accommodating the other of the first intra-catheter stiffener element distal end and the second intra-catheter stiffener element distal end, in accordance with an embodiment of the present disclosure.

In one embodiment, a first intra-catheter stiffener element and a second intra-catheter stiffener element include at least one of an eye portion and a looped portion disposed at the distal end thereof capable of receiving and facilitating disposition therethrough of the distal end of the other of the first intra-catheter stiffener element and the second intra-catheter stiffener element. The catheter body in which the first and second intra-catheter stiffener elements are disposed includes a septum for separating the first lumen and the second lumen from one another, the septum having a distal end extending beyond at least one of the first distal opening and the second distal opening for at least minimizing backflow into at least one of the first lumen and the second lumen. One of the first intra-catheter stiffener element and the second intra-catheter stiffener element includes a cover portion at the distal end thereof, the cover portion capable of deployment and retraction in relation to one of the first lumen and the second lumen, and the cover portion cooperatively engageable with the septum distal end for at least minimizing backflow into the one of the first lumen and the second lumen. The cover portion is deployable and retractable via at least one technique of a rotation and a translation in relation to a longitudinal axis thereof. One or both of the first and second intra-catheter stiffener elements may have a monolithic configuration or a tapered configuration. The first intra-catheter stiffener element may have a first length, and the second intra-catheter stiffener element may have a second length different from the first length. The first intra-catheter stiffener element may include a first coupler at a proximal end thereof, and the second intra-catheter stiffener element may include a second coupler at a proximal end thereof. The distal end of the first intra-catheter stiffener element may be distal in relation to the distal end of the second intra-catheter stiffener element when the first coupler and second coupler are coupled to the catheter body. The first coupler of the first intra-catheter stiffener element may be configured to mate with a first mating coupler at a first proximal opening of the catheter body, and the second coupler of the second intra-catheter stiffener element may be configured to mate with a second mating coupler at a second proximal opening of the catheter body. The first intra-catheter stiffener element may include an exterior cross-sectional shape complementing an interior cross-sectional shape of the first lumen, and the second intra-catheter stiffener element may include an exterior cross-sectional shape complementing an interior cross-sectional shape of the second lumen. The exterior cross-sectional shape of the first intra-catheter stiffener element may include a round shape, an oval shape, an elliptical shape, or an ovoidal shape, and the exterior cross-sectional shape of the second intra-catheter stiffener element may include a round shape, an oval shape, an elliptical shape, or an ovoidal shape.

Further, a method of fabricating a catheter apparatus, includes providing/obtaining a catheter comprising a first lumen capable of fluid communication via a first distal opening and a second lumen capable of fluid communication via a second distal opening; providing/obtaining a first intra-catheter stiffener element configured for disposition through the first lumen such that a distal end thereof is distal in relation to the first distal opening, the first intra-catheter stiffener element comprising one of a guide-wire and a stylet; and providing/obtaining a second intra-catheter stiffener element configured for disposition through the second lumen such that a distal end thereof is distal in relation to the second distal opening, the second intra-catheter stiffener element comprising a guide-wire, providing/obtaining the first intra-catheter stiffener element and providing/obtaining a second intra-catheter stiffener element, together, comprising providing/obtaining one of the first intra-catheter stiffener element distal end and the second intra-catheter stiffener element distal end as capable of receiving and accommodating the other of the first intra-catheter stiffener element distal end and the second intra-catheter stiffener element distal end, in accordance with an embodiment of the present disclosure.

Further, a method of fabricating a catheter apparatus, includes providing/obtaining a catheter comprising a first lumen capable of fluid communication via a first distal opening and a second lumen capable of fluid communication via a second distal opening; providing/obtaining a first intra-catheter stiffener element configured for disposition through the first lumen such that a distal end thereof is distal in relation to the first distal opening, the first intra-catheter stiffener element comprising one of a guide-wire and a stylet; and providing/obtaining a second intra-catheter stiffener element configured for disposition through the second lumen such that a distal end thereof is distal in relation to the second distal opening, the second intra-catheter stiffener element comprising a guide-wire, wherein the first intra-catheter stiffener element and the second intra-catheter stiffener element include a first intra-catheter stiffener element distal end and a second intra-catheter stiffener element distal end, respectively. The first lumen capable of receiving and accommodating the first intra-catheter stiffener element, and the second lumen capable of receiving and accommodating the second intra-catheter stiffener element distal end. The method may include inserting the first intra-catheter stiffener element into the first lumen and/or inserting the second intra-catheter stiffener element into the second lumen. The method may include steps to form any of the features described above or elsewhere in this disclosure, e.g., forming a catheter, stiffener element, and/or guide-wire with any of the shapes and/or features described herein. This may include forming these by extrusion, mold, carving, etching, injection mold, 3D printing, etc.

Furthermore, a method of treatment, treating a patient, and/or inserting a catheter into a blood vessel by way of a catheter apparatus, includes providing/obtaining the catheter apparatus, the catheter apparatus comprising a catheter having a first lumen capable of fluid communication via a first distal opening and a second lumen capable of fluid communication via a second distal opening; providing/obtaining a first intra-catheter stiffener element configured for disposition through the first lumen such that a distal end thereof is distal in relation to the first distal opening, the first intra-catheter stiffener element providing comprising providing one of a guide-wire and a stylet; and providing/obtaining a second intra-catheter stiffener element configured for disposition through the second lumen such that a distal end thereof is distal in relation to the second distal opening, the second intra-catheter stiffener element providing/obtaining comprising providing/obtaining a guide-wire, providing/obtaining the first intra-catheter stiffener element and providing/obtaining a second intra-catheter stiffener element, together, comprising providing/obtaining one of the first intra-catheter stiffener element distal end and the second intra-catheter stiffener element distal end as capable of receiving and accommodating the other of the first intra-catheter stiffener element distal end and the second intra-catheter stiffener element distal end; creating a first entry; deforming the stylet tip by way of receiving and disposing the at least one elongated element in the at least one lumen; disposing a distal end of the catheter body through the first entry; creating a second entry; disposing the distal end of the catheter body through the second entry; and reforming the stylet tip by way of withdrawing the at least one elongated element from the at least one lumen, thereby minimizing trauma to the blood vessel, in accordance with an embodiment of the present disclosure.

Furthermore, a method of treatment, treating a patient, and/or inserting a catheter into a blood vessel by way of a catheter apparatus, includes providing/obtaining the catheter apparatus, the catheter apparatus comprising a catheter/catheter body having a first lumen capable of fluid communication via a first distal opening and a second lumen capable of fluid communication via a second distal opening; the catheter apparatus also comprising a first intra-catheter stiffener element configured for disposition through the first lumen such that a distal end thereof is distal in relation to the first distal opening, the first intra-catheter stiffener element comprising one of a guide-wire and a stylet; and the catheter apparatus comprising a second intra-catheter stiffener element configured for disposition through the second lumen such that a distal end thereof is distal in relation to the second distal opening, wherein the second intra-catheter stiffener element comprises a guide-wire and/or a stylet, wherein the first intra-catheter stiffener element and the second intra-catheter stiffener element include a first intra-catheter stiffener element distal end and the second intra-catheter stiffener element distal end, respectively. The first lumen is configured to receive and accommodate the first intra-catheter stiffener element and/or the first intra-catheter stiffener element distal end and the second lumen is configured to receive and accommodate the second intra-catheter stiffener element and/or the second intra-catheter stiffener element distal end. The method may include creating a first entry or incision into a patient, tissue, and/or blood vessel. The method may include inserting the catheter apparatus or any portion of the catheter apparatus (e.g., the catheter and/or stiffener element). The method may include deforming the stylet tip by way of receiving and disposing at least one elongated element (e.g., a guide-wire or stylet or other stiffener element) in at least one lumen the stiffener element. The method may include disposing a distal end of the catheter/catheter body through the first entry or incision. The method may include creating a second entry or incision into the patient, tissue, and/or blood vessel. The method may include disposing the distal end of the catheter/catheter body through the second entry. The method may include reforming the stylet tip by way of withdrawing the at least one elongated element from the at least one lumen, thereby minimizing trauma to the blood vessel, in accordance with an embodiment of the present disclosure.

Furthermore, a method of treatment, treating a patient, and/or a method of inserting a catheter into a blood vessel by way of a catheter apparatus, includes providing the catheter apparatus, including a catheter body and a plurality of stylets joined at a proximal end and disposable within the catheter body, the plurality of stylets each comprising a lumen and an expandable stylet tip, wherein each lumen of the plurality of stylets is capable of receiving at least one elongated element and facilitating fluid communication; creating a first incision into a patient; deforming the stylet tip by way of receiving and disposing the at least one elongated element in at least one lumen of the plurality of stylets; disposing a distal end of the catheter body through the first incision; creating a second incision in a patient, tissue, or blood vessel; disposing the distal end of the catheter body through the second incision; and reforming the stylet tip by way of withdrawing the at least one elongated element from the at least one lumen, thereby minimizing trauma to the blood vessel.

The embodiments described herein may be used, for example, in the field of hemodialysis, or other fields, for inserting a single-tip or a multi-tip catheter into a blood vessel. The apparatuses, systems, and methods are believed to facilitate insertion of a single-tip or a multi-tip catheter without using a tearable sheath by employing a variety of structures and techniques using enhanced stiffening and guiding features.

BRIEF DESCRIPTION OF THE DRAWING

The above, and other, aspects, features, and benefits of several embodiments of the present disclosure will be more apparent from the following Detailed Description as presented in conjunction with the following several figures of the Drawing. Corresponding reference characters or reference numerals may indicate corresponding components throughout the several figures of the Drawing. Elements in the several figures are illustrated for simplicity and clarity and have not necessarily been drawn to scale. For example, the dimensions of some elements in the figures may be emphasized relative to other elements for facilitating understanding of the various presently disclosed embodiments. Also, well-understood elements that are useful or necessary in commercially feasible embodiments are often not depicted in order to facilitate a less obstructed view of these various embodiments of the present disclosure.

FIG. 20A is a schematic diagram illustrating a cutaway top view of a catheter apparatus, e.g., of a catheter insertion system, comprising a catheter body having two lumens separated by a septum, a single stylet disposed through one lumen; and a single guide-wire (not shown) may also be disposed through the other lumen, a distal end of the guide-wire being disposable within at least one portion of the stylet, such as useable in a catheter system, in accordance with an embodiment of the present disclosure.

FIG. 20B is a schematic diagram illustrating a cutaway side view of a catheter apparatus, e.g., of a catheter insertion system, comprising a catheter body having two lumens separated by a septum, a single stylet disposed through one lumen; and a single guide-wire (not shown) may be disposed through the other lumen, a distal end of the guide-wire being disposable within at least one portion of the stylet, such as useable in a catheter system, in accordance with an embodiment of the present disclosure.

FIG. 21A is a schematic diagram illustrating a cutaway top view of a catheter apparatus, e.g., of a catheter insertion system, comprising a catheter body having two lumens separated by a septum, a guide-wire disposed through a first lumen, wherein the guide-wire distal end includes a looped portion, in accordance with an embodiment of the present disclosure.

FIG. 21B is a schematic diagram illustrating a cutaway side view of the catheter apparatus of FIG. 21A, comprising a catheter body having two lumens separated by a septum, a guide-wire disposed through each lumen; a distal end of one guide-wire being disposable through a lopped portion of the distal end of the other guide-wire, in accordance with an embodiment of the present disclosure.

DETAILED DESCRIPTION

Figure 1:
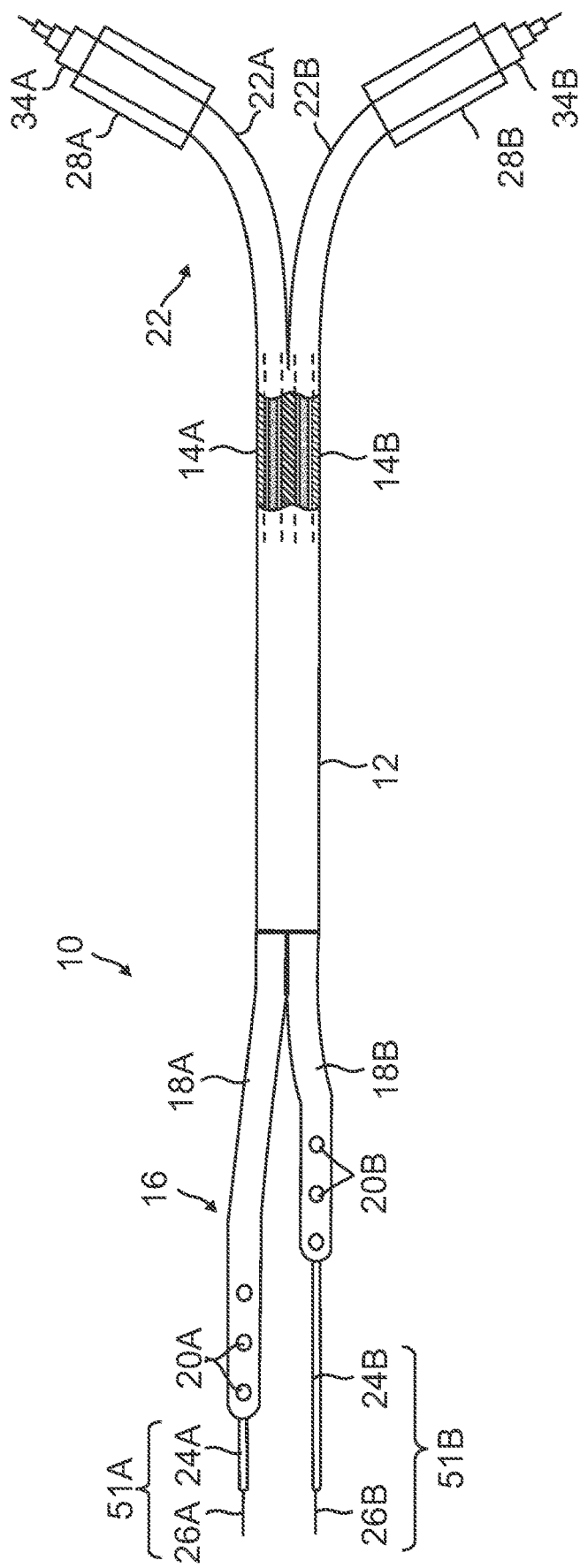
FIG. 1 is a schematic diagram illustrating a partially cutaway side view of a hemodialysis catheter apparatus of a catheter insertion system, in accordance with an embodiment of the present disclosure.

Referring to FIG. 1, this schematic diagram illustrates, in a partially cutaway side view, a catheter system 10, such as a hemodialysis catheter insertion system, in accordance with an embodiment of the present disclosure. The catheter system 10 includes a catheter body 12 with two internal lumens 14A and 14B. The catheter body 12 has a "split-tip" distal end 16 in which the body (and lumens) separate into two distal tip portions, 18A and 18B, which form a single-lumen distal blood return extension tube and a single-lumen distal blood removal extension tube, respectively. The split-tips can, but need not have, one or more side ports 20A and 20B, in fluid communication with one or the other of the lumens 14A and 14B to facilitate respective blood return and removal during hemodialysis.

Still referring to FIG. 1, alternatively, or in conjunction with side ports, the distal ends 16 can be open to provide fluid passageways for blood removal and return. The proximal end 22 of the catheter body 12 can also be split into separate segments 22A and 22B and terminate with two couplers 28A and 28B, which can include couplings 34A and 34B, such luer-locks or the like, to couple the catheter system 10 to a hemodialysis machine (not shown) in which blood is circulated and purified. Proximal segments 22A, 22B, thus, respectively provide a single-lumen proximal blood return extension tube and a single-lumen proximal blood removal extension tube. However, an additional lumen or lumens are also possible.

Still referring to FIG. 1, the overall system or kit of the present disclosure can also include two intra-catheter stiffener elements 51A and 51B each of which can include either one or more stylets 24A, 24B respectively, or one or more guide-wires 26A, 26B respectively, or both a stylet and a guide-wire whereby the guide wires 26A, 26B are disposed within stylets 24A, 24B respectively, and are shown within the respective lumens 14A and 14B. The catheter body 12 is typically a very flexible silicone, polyurethane, or other biocompatible composition, e.g., having a stiffness in the range of about 65 to about 85 durometers. Preferably, the stylets 24A, 24B comprise a stiffer form of polyethylene or other bio-compatible material. In addition to stiffening the assembly, the stylets 24A, 24B facilitate preventing kinking of the catheter body 12 during insertion.

Figure 2:
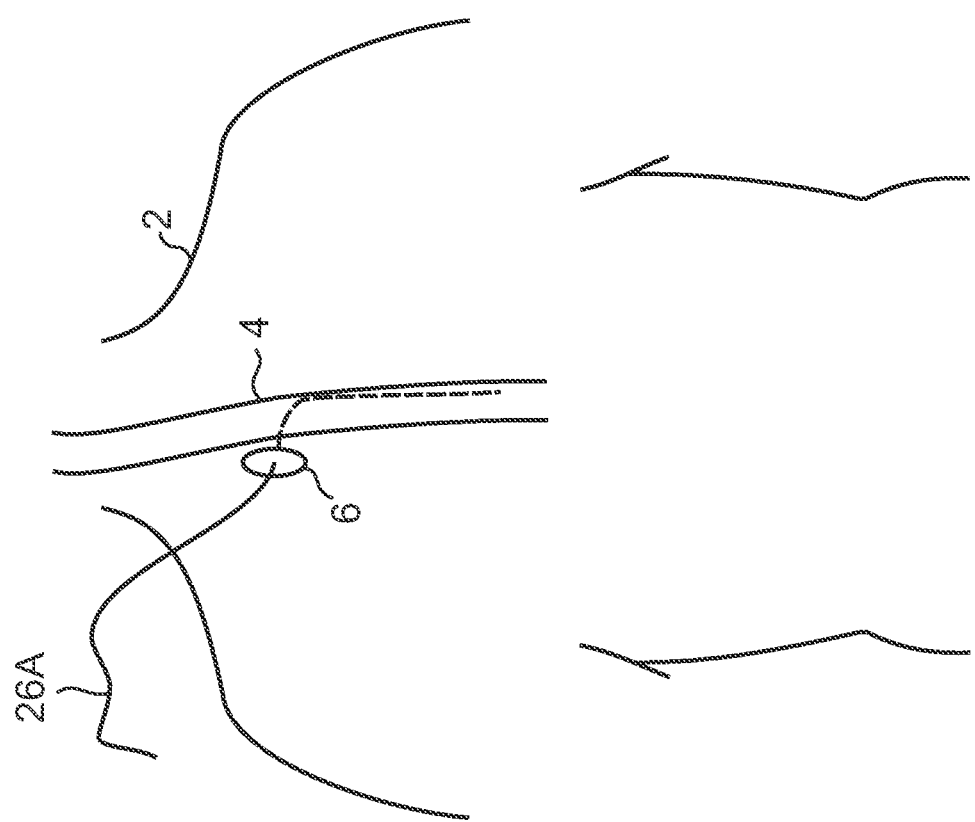
FIG. 2 is a schematic diagram illustrating performing a step of a method, e.g., by using a catheter apparatus of a catheter insertion system, wherein a distal portion of a first guide-wire is inserted into a vessel, in accordance with an embodiment of the present disclosure.

Still referring to FIG. 1, the catheter apparatus 10 of a catheter system facilitates insertion of the distal end of the multi-lumen, split-tip, flexible catheter body 12 into a blood vessel using the stylets 24A, 24B and guide-wires 26A, 26B, as will be explained below. Briefly, a distal portion of each guide-wire 26A, 26B is disposed at a desired position within the vessel. A stylet 24A, 24B having a tapered tip to facilitate insertion into the vessel and to provide catheter stiffening is slidably disposed along the length of each catheter lumen 14A, 14B until it extends beyond the distal tip of that catheter lumen 14A, 14B. A proximal end of each guide-wire 26A, 26B is threaded through a distal end of a lumen 14A, 14B extending along each of the stylets 24A, 24B. The catheter body 12 is then advanced over the guide-wires 26A, 26B and into a blood vessel 4 (FIG. 2). Optionally, the catheter body 12 can be advanced over the guide-wires 26A, 26B until the distal end is adjacent to the vessel, at which point the catheter body 12 and guide-wires 26A, 26B can be advanced together into the blood vessel. The guide-wires 26A, 26B and stylets 24A, 24B are then removed from the catheter body 12. The methods and application kit described can be used for any split-tip catheter, and are particularly useful for insertion of subcutaneously tunneled hemodialysis catheters, as contemplated by the present disclosure.

Referring to FIGS. 2-11, these schematic diagrams, together, illustrate various steps in one or more methods of inserting a catheter body 12 by way of a catheter apparatus 10 of a catheter system, such as a multi-lumen split-tip catheter having at least one enhanced stylet, into a blood vessel, in accordance with an embodiment of the present disclosure. The method involves, not only inserting the catheter tips into a blood vessel, but also forming a subcutaneous tunnel below a patient's skin to secure the catheter body 12 in place and is sometimes described as antegrade or forward insertion. The methods described herein can also be used for inserting catheter tips into a blood vessel where tunneling is not necessary or desired, as encompassed by the present disclosure.

Referring to FIG. 2, this schematic diagram illustrates performing a step, e.g., an initial step, of an inserting method, wherein a distal portion of a first guide-wire 26A is inserted into a vessel 4, such as a blood vessel, of a patient 2, in accordance with an embodiment of the present disclosure. The entry location 6 of the guide-wire 26A is referred herein as the "first location" or the "venotomy site." This first location is typically a surgical incision that provides access to the desired blood vessel which typically includes the internal or external jugular, femoral or subclavian vein, and the vena cava, for example. In a preferred embodiment, the blood vessel chosen for catheter placement can be the right side internal jugular vein.

Figure 3:
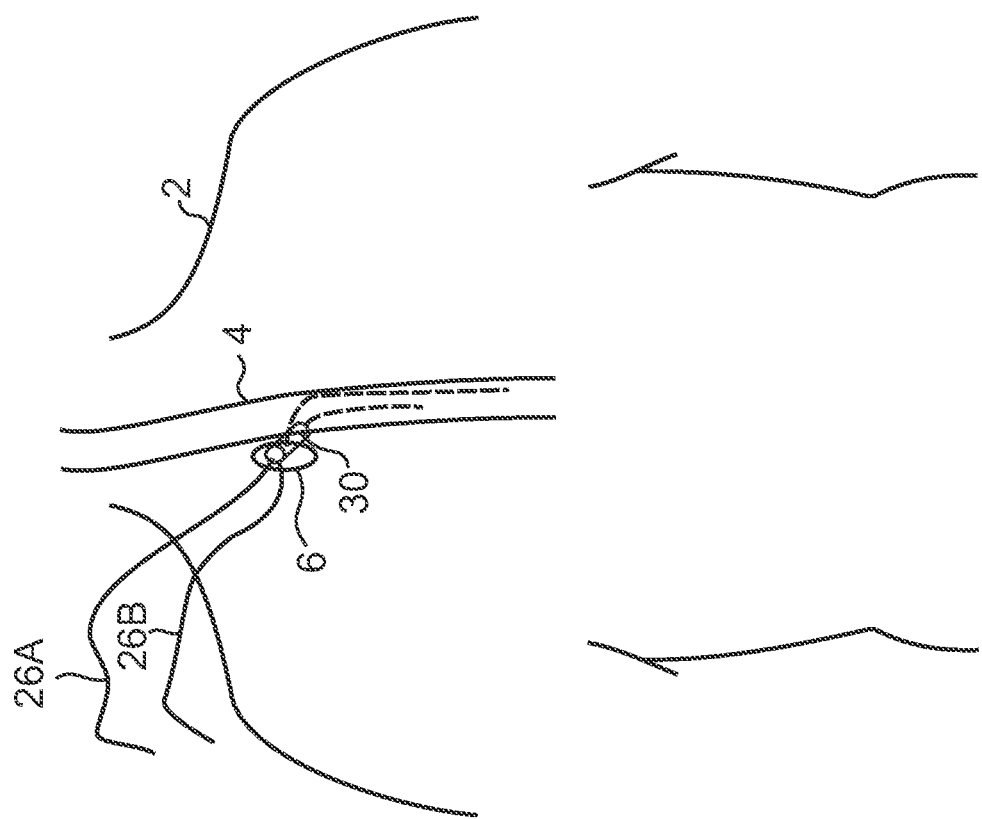
FIG. 3 is a schematic diagram illustrating performing a step of a method, e.g., by using a catheter apparatus of a catheter insertion system, wherein a blood vessel dilating sheath and a distal portion of a second guide-wire are inserted into a vessel, in accordance with an embodiment of the present disclosure.

Referring to FIG. 3, this schematic diagram illustrates performing a step of an inserting method, wherein a blood vessel dilating sheath 30 and a distal portion of a second guide-wire 26B are inserted into a vessel 4, such as a blood vessel, of a patient 2, in accordance with an embodiment of the present disclosure. The blood vessel sheath/dilator 30 is shown as inserted over the first guide-wire 26A to dilate the vessel 4.

Figure 4:
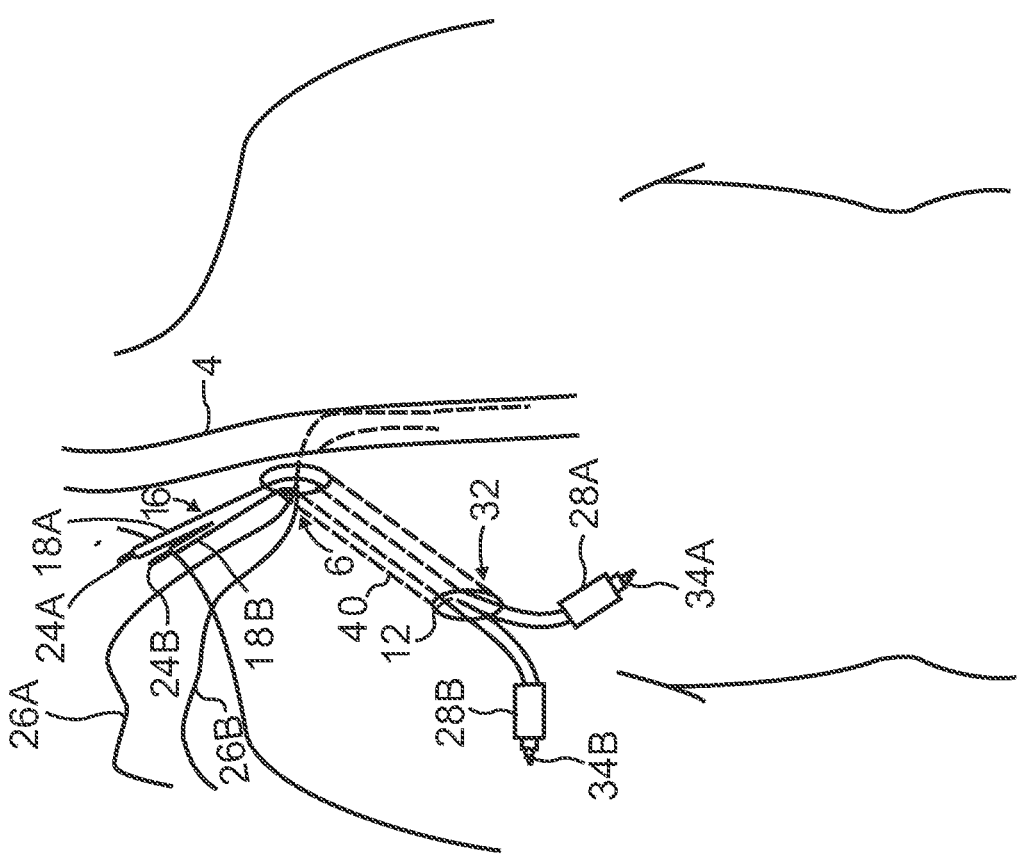
FIG. 4 is a schematic diagram illustrating performing a step of a method, e.g., by using a catheter apparatus of a catheter insertion system, wherein a catheter is disposed in a subcutaneous tunnel between a first location and a second location, in accordance with an embodiment of the present disclosure.

Referring to FIG. 4, this schematic diagram illustrates performing a step of an inserting method, wherein an antegrade catheter is disposed in a subcutaneous tunnel 40 between a first location 6 and a second location 32, in accordance with an embodiment of the present disclosure. The subcutaneous tunnel 40 is formed (before or after the insertion of guide-wires 26A and 26B) to anchor the catheter body 12 in place and to provide two couplers 28A, 28B for coupling the two lumens 14A, 14B of the catheter system 10 to a dialysis machine (not shown) using couplings 34A, 34B. The catheter body 12 of an antegrade catheter is disposed in a subcutaneous tunnel 40 between the first (venous access) location 6 and a second (exit) location 32, such that the distal end of the instrument 16 including the split tips 18A and 18B extend from the first location 6. Prior to insertion, each of the lumens 14A, 14B of catheter body 12 has been fitted with a hollow, tubular, intra-catheter stiffener element or liner, such as stylets 24A and 24B, respectively.

Figure 5:
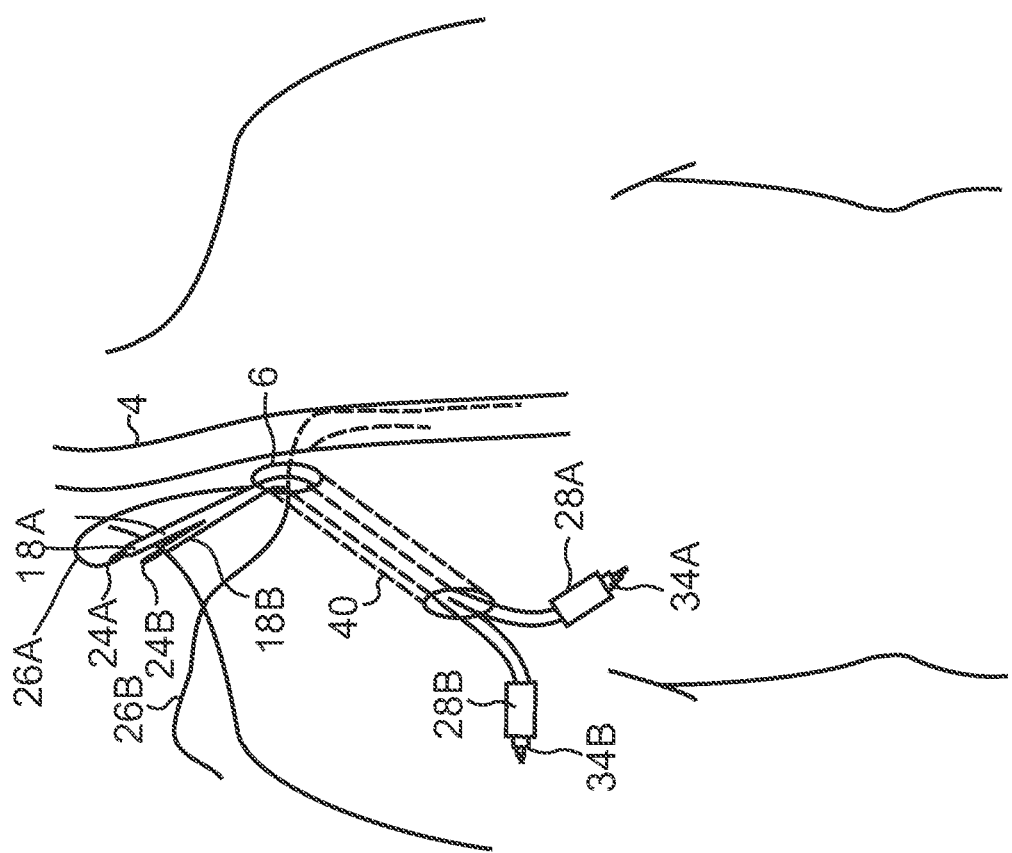
FIG. 5 is a schematic diagram illustrating performing a step of a method, e.g., by using a catheter apparatus of a catheter insertion system, wherein the first guide-wire is threaded through a first lumen of a catheter assembly, and wherein the catheter assembly has an intra-catheter stiffener element is disposed in each lumen of the catheter, in accordance with an embodiment of the present disclosure.

Referring to FIG. 5, this schematic diagram illustrates performing a step of an inserting method, wherein the first guide-wire 26A is threaded through a first lumen 14A of a catheter system 10, and wherein the catheter system 10 has stylets 24A and 24B disposed in each lumen 14A, 14B of the catheter body 12, in accordance with an embodiment of the present disclosure. The first guide-wire 26A is threaded through a first lumen 14A of a catheter system 10, e.g., through the lumen 14A associated with the stylet 24A, and wherein the catheter system 10 has a stylet 24A and a stylet 24B disposed in each lumen 14A, 14B of the catheter body 12.

Figure 6:
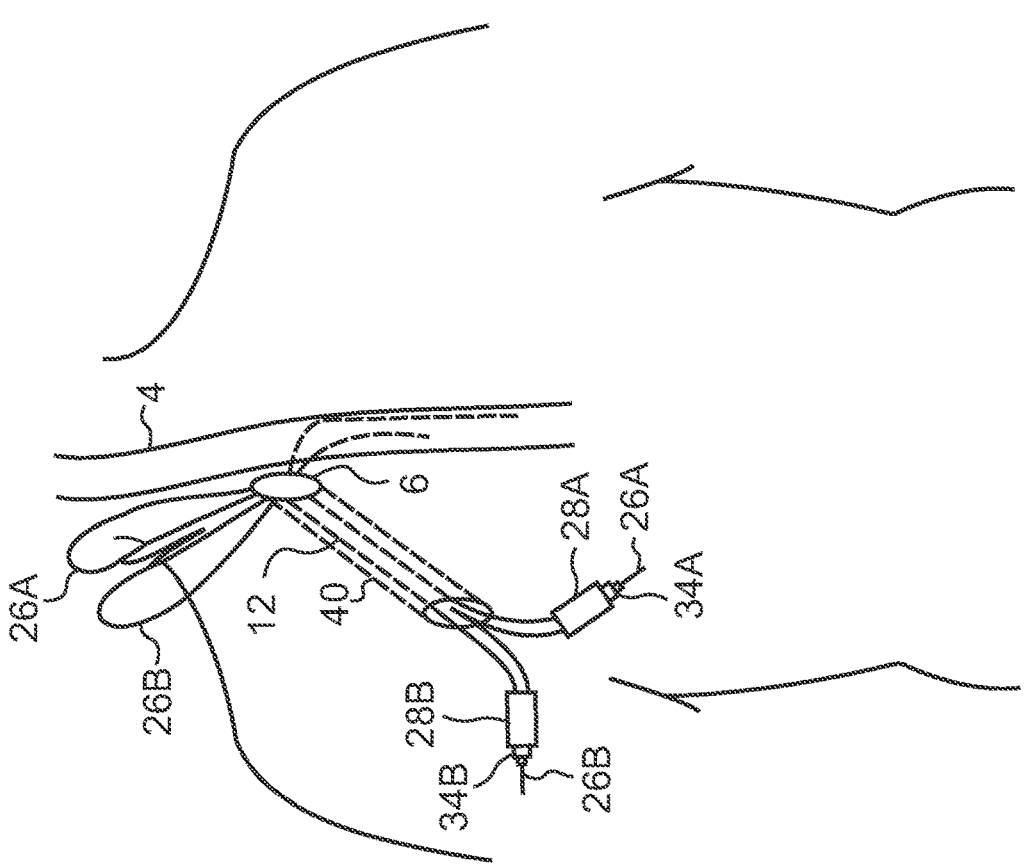
FIG. 6 is a schematic diagram illustrating performing a step of a method, e.g., by using a catheter apparatus of a catheter insertion system, wherein the second guide-wire is threaded through the second lumen of the catheter assembly to a point where two loops of guide-wire remain to facilitate placement of the distal end of the catheter in the vessel, in accordance with an embodiment of the present disclosure.

Referring to FIG. 6, this schematic diagram illustrates performing a step of an inserting method, wherein the second guide-wire 26B is threaded through the second lumen 14B of the catheter apparatus 10 to a point where two loops of guide-wire remain to facilitate placement of the distal end of the catheter body 12 in the vessel 4, in accordance with an embodiment of the present disclosure. The second guide-wire 26B is threaded through the second lumen 14B of the catheter system 10, e.g., through the lumen 14B associated with the stylet 24B. Each of the guide-wires 26A, 26B is advanced through the catheter body 12 to a point where two short loops of guide-wire 26A, 26B remain to facilitate placement of the distal end of the catheter body 16 in the vessel 4.

Figure 7:
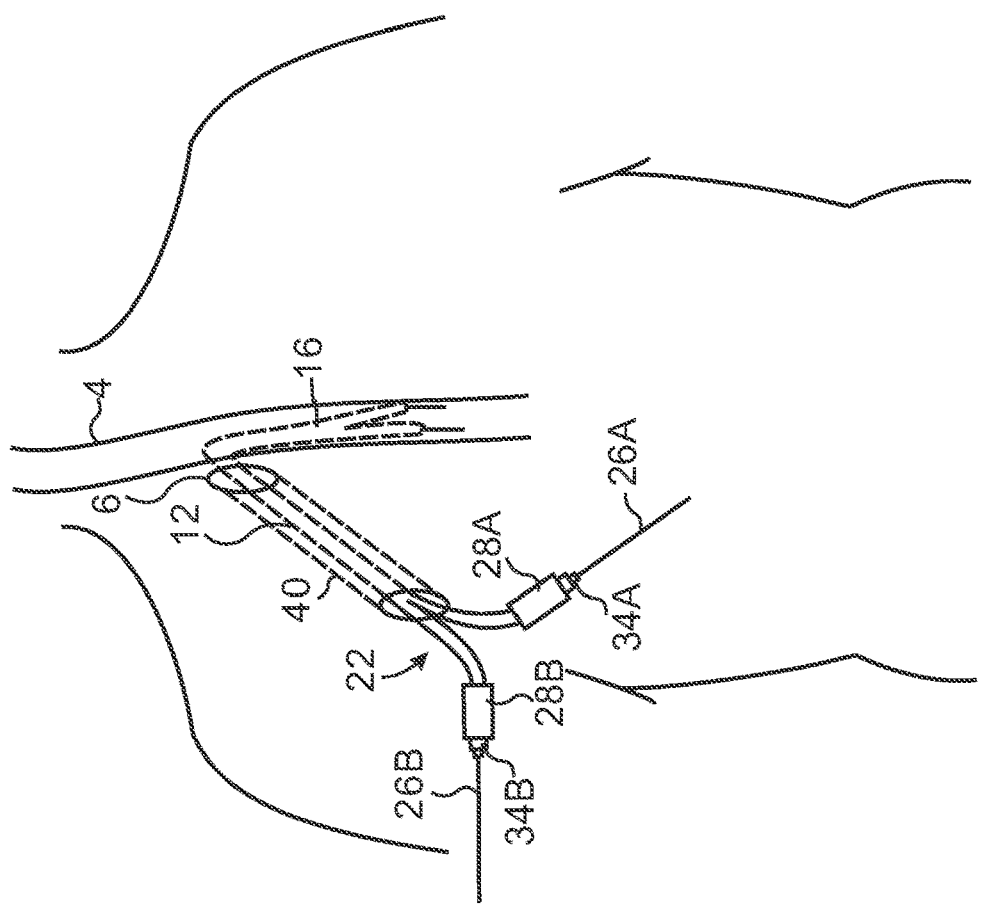
FIG. 7 is a schematic diagram illustrating performing a step of a method, e.g., by using a catheter apparatus of a catheter insertion system, wherein the catheter assembly has been advanced along the guide-wires until the distal portion of the catheter is positioned within the vessel at a desired location, in accordance with an embodiment of the present disclosure.

Referring to FIG. 7, this schematic diagram illustrates performing a step of an inserting method, wherein the catheter system 10 has been advanced along the guide-wires 26A, 26B until the distal portion of the catheter body 12 is positioned within the vessel 4 at a desired location, in accordance with an embodiment of the present disclosure. In a preferred embodiment, the catheter body 12 is advanced over the guide-wires 26A, 26B until the distal end is adjacent to the vessel 4, and then the catheter body 12 and the guide-wires 26A, 26B can be advanced together until the distal end of the catheter body 12 is positioned at a desired position within the vessel 4. The guide-wires 26A, 26B can then be removed by withdrawing them via the proximal end 22 of the catheter body 12. Likewise, the stylets 24A, 24B can be removed (either subsequent to or before the guide-wires 26A, 26B or at the same time). Advantageously, this method precludes using a vessel dilator larger than the catheter/stiffeners assembly for placement of the catheter body 12 within the vessel 4 since the stylets 24A, 24B and the catheter body 12 themselves provide vessel dilation.

Figure 8:
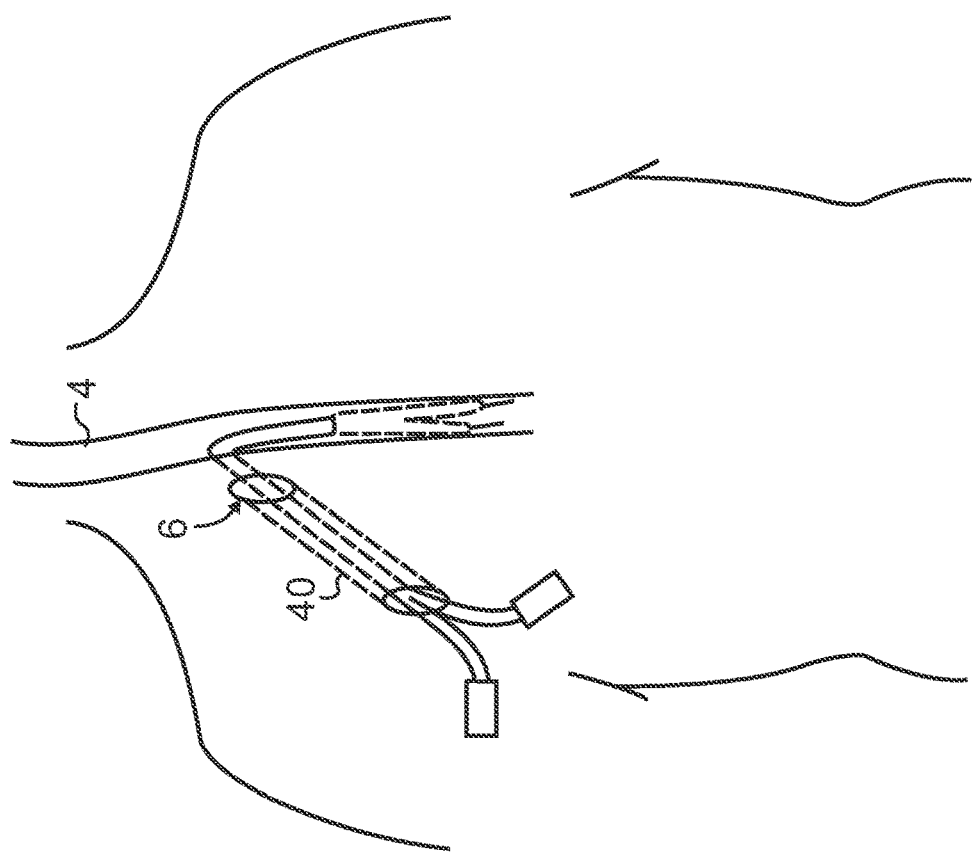
FIG. 8 is a schematic diagram illustrating performing a step of a method, e.g., by using a catheter apparatus of a catheter insertion system, as shown in FIG. 7, wherein the intra-catheter stiffener elements and guide-wires removed, in accordance with an embodiment of the present disclosure.

Referring to FIG. 8, this schematic diagram illustrates performing a step of an inserting method, as shown in FIG. 7, wherein the stylets 24A, 24B and guide-wires 26A, 26B are removed, in accordance with an embodiment of the present disclosure. The venous access incision or entry location 6 is then closed and the catheter body 12 is secured subcutaneously (e.g., via an implanted cuff and/or sutures).

Figure 9:
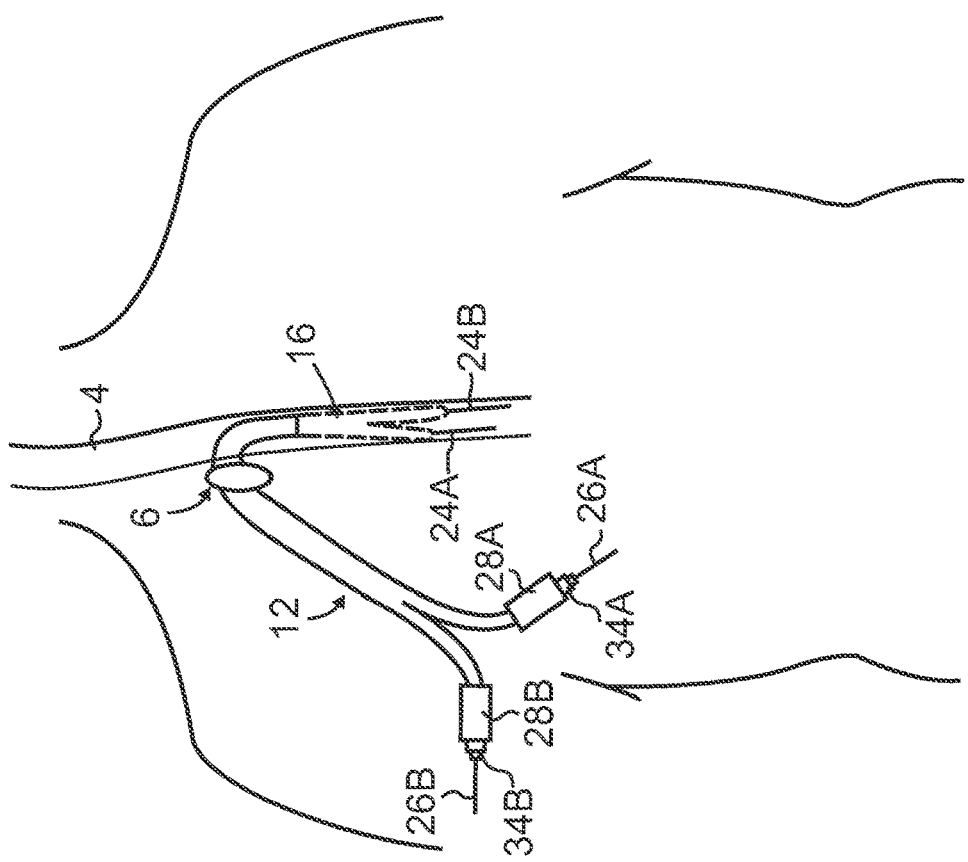
FIG. 9 is a schematic diagram illustrating performing a step of a method, e.g., by using a catheter apparatus of a catheter insertion system, wherein a retrograde catheter is shown having a distal end disposed in a vessel, in accordance with an embodiment of the present disclosure.
Figure 10:
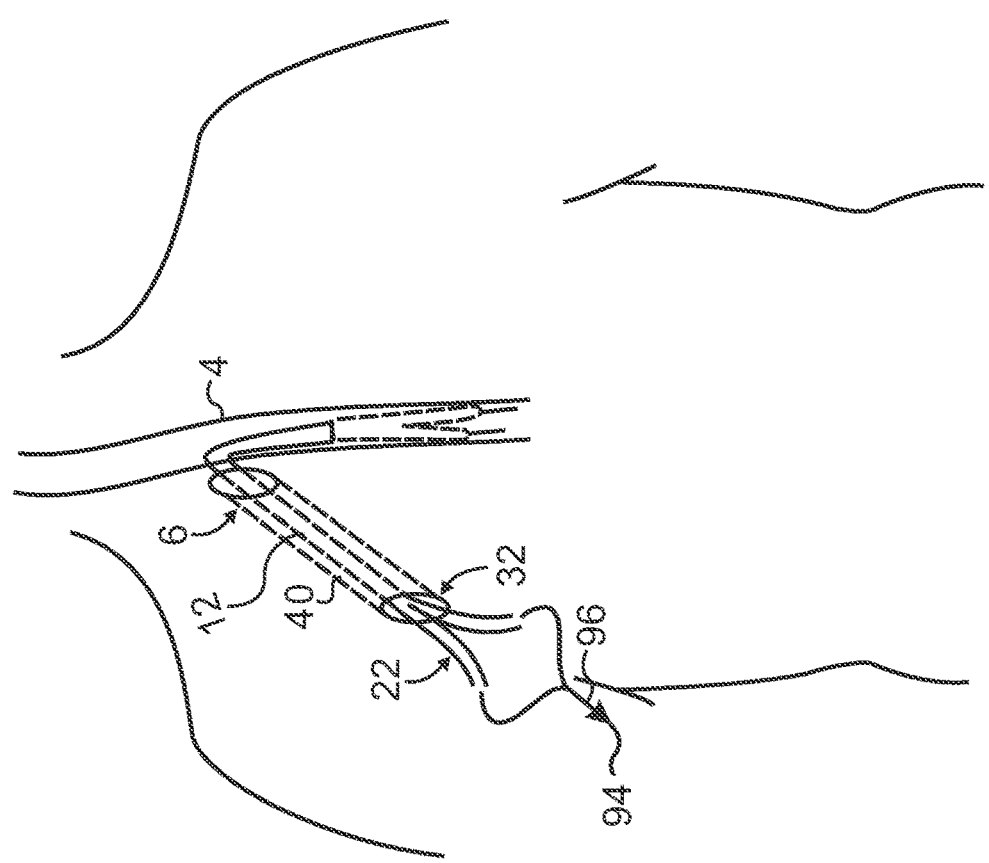
FIG. 10 is a schematic diagram illustrating performing a step of a method, e.g., by using a catheter apparatus of a catheter insertion system, wherein the catheter has been subcutaneously tunneled subsequent to placement of the distal end of the catheter in a vessel, in accordance with an embodiment of the present disclosure.

Referring back to FIGS. 2-8 and forward to FIGS. 9 and 10, although the above detailed description has been presented in connection with an antegrade insertion, the apparatuses, systems, and methods of the present disclosure are also useful in retrograde or reverse insertions, e.g., wherein the catheter body 12 is passed through the subcutaneous tunnel 40 from the venotomy site 6 to the remote exit location, such as a second (exit) location 32. Thus, the method, according to one embodiment of the present disclosure, for insertion of a retrograde catheter will next be described. For the method, an initial step of inserting a retrograde catheter begins with placement of guide-wires 26A, 26B within the vessel 4 as described above in connection with FIGS. 2 and 3.

Referring to FIG. 9, this schematic diagram illustrates performing a step of an inserting method, wherein a retrograde catheter is shown having a distal end disposed in a vessel 4, in accordance with an embodiment of the present disclosure. The catheter body 12 has each of the lumens 14A, 14B fitted with a hollow, tubular, intra-catheter stiffener element or liner, such as a stylet 24A and 24B, respectively. The stylets 24A, 24B can have a coupler, such as fluid-couplers 28A, 28B, disposed at a proximal end that releasably couple with a mating coupler at a proximal end of the respective catheter lumen 14A, 14B. The guide-wires 26A, 26B are threaded through the lumens 14A, 14B of the catheter system 10 as described above in relation to FIGS. 5 and 6. The catheter body 12 is advanced along the guide-wires 26A, 26B until the distal end of the catheter body 12 in a desired location within the vessel 4. Optionally, the catheter body 12 can be advanced along the guide-wires 26A, 26B until the distal end is adjacent to the vessel 4, and then the catheter body 12 and the guide-wires 26A, 26B can be advanced until the distal end is located at a desired position within the vessel 4. The guide-wires 26A, 26B and, optionally, the stylets 24A, 24B are then removed from the lumens 14A, 14B.

Referring to FIG. 10, this schematic diagram illustrates performing a step of an inserting method, wherein the catheter body 12 has been subcutaneously disposed in a subcutaneous tunnel subsequent to the distal end of the catheter body 12 being disposed in a vessel, in accordance with an embodiment of the present disclosure. A subcutaneous tunnel 40 is formed between a second location, e.g., the exit location 32, and the first location, e.g., the venotomy site 6. Couplers at the proximal end 22 of the catheter lumens 14A, 14B are removed 94, 96 or optionally, severed therefrom to allow the proximal end 22 of the catheter body 12 to be pulled through the tunnel 40. In an embodiment, the proximal end 22 of the catheter body 12 is pulled through the subcutaneous tunnel 40 from the first location, e.g., the venotomy site 6, until the catheter body 12 extends from the second location, e.g., the exit location 32. Fluid couplers (e.g., couplers 28A, 28B as shown in FIG. 11) may be installed/added to the catheter body 12, e.g., after placement in the subcutaneous tunnel, wherein the coupler installing/adding step may include disposing fluid-couplers 28A, 28B in relation to at least one proximal end 22 of the catheter body 12.

Figure 11:
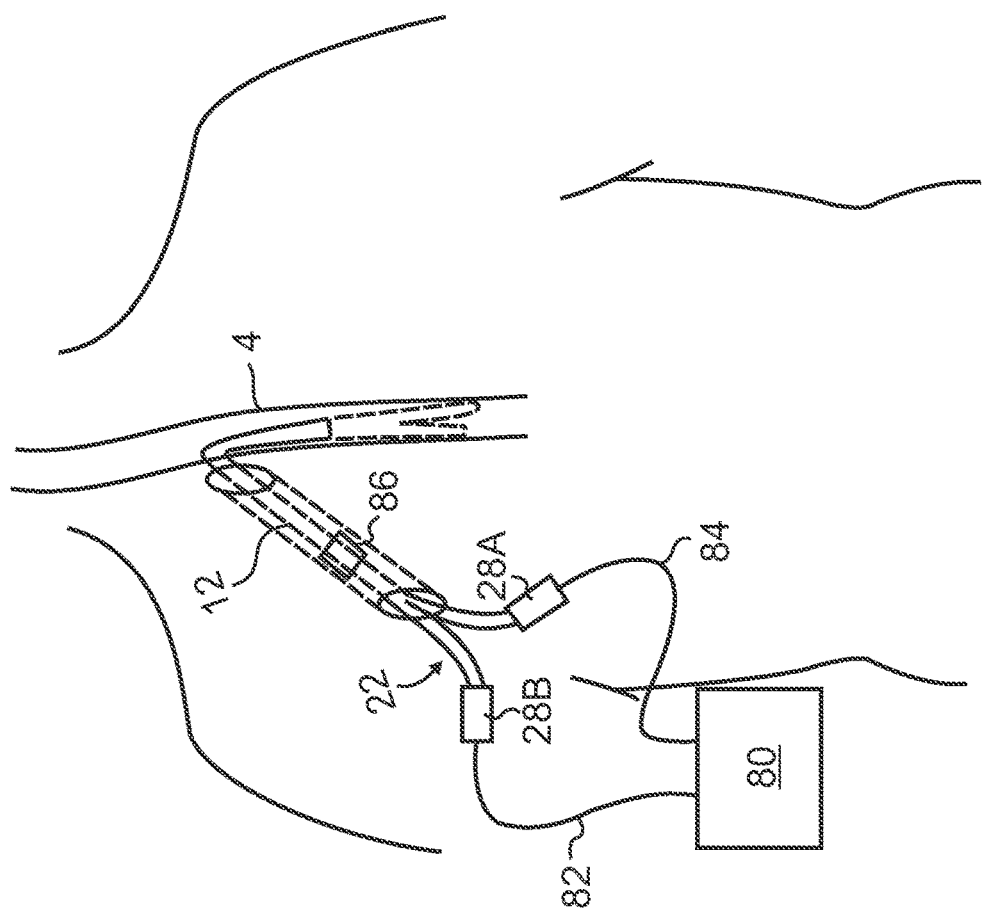
FIG. 11 is a schematic diagram illustrating performing a step of connecting fluid couplers to a hemodialysis machine, e.g., in a method of inserting/using a catheter body by way of a catheter system, in accordance with an embodiment of the present disclosure.

Referring to FIG. 11, this schematic diagram illustrates performing a step of connecting fluid couplers 28A, 28B to a hemodialysis machine 80, in a method of inserting a catheter body 12 by way of a catheter system 10. The catheter body 12, after disposing through the tunnel 40 with fluid-couplers 28A, 28B being installed, or optionally, replaced, is ready to be coupled to a hemodialysis machine 80 for blood purification, such as by way of fluid lines 82, 84. The stiffener elements, including stylets 24A, 24B and/or guide-wires 26A, 26B may be removed prior to coupling to the hemodialysis machine 80. An ingrowth cuff 86 facilitates tissue growth to secure catheter body 12 within the subcutaneous tunnel 40. As noted above, the use of the stylets 24A, 24B provides sufficient stiffness such that the flexible split-tips can be slid over the guide-wires 26A, 26B into the desired position with less effort and reduced likelihood of trauma to the patient. Catheter kinking is mitigated during the inserting method, thus reducing complexity of catheter insertion.

Figure 12:
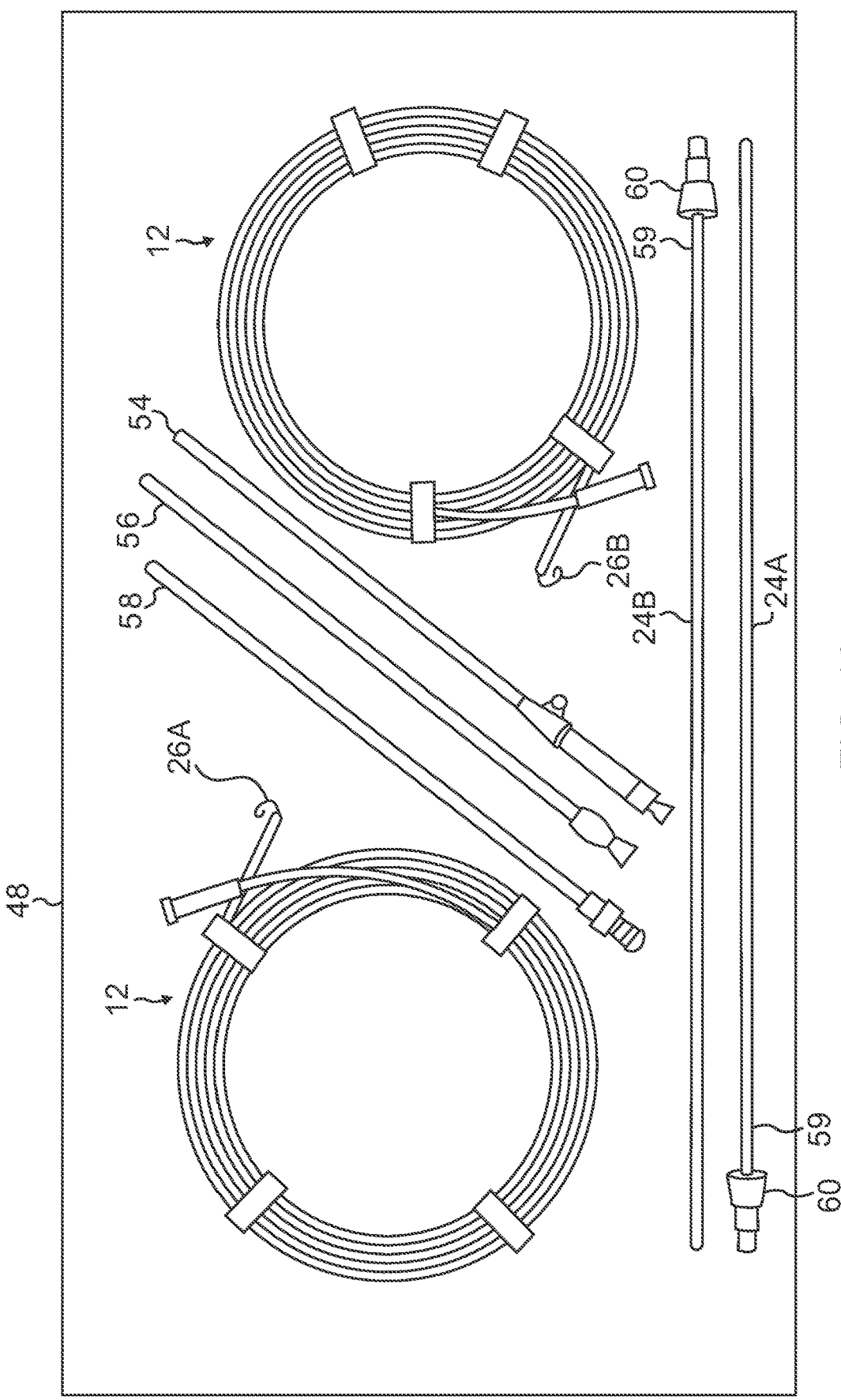
FIG. 12 is a schematic diagram illustrating an exemplary kit for installing a catheter or catheters by using a catheter apparatus, e.g., of a catheter insertion system, in accordance with an embodiment of the present disclosure.

Referring to FIG. 12, this schematic diagram illustrates a catheter kit 48 for installing catheters, such as catheter bodies 12 of catheter systems 10, in accordance with an embodiment of the present disclosure. In FIG. 12 catheter bodies 12 are generic representations that can correspond to a wide variety of catheter types and shapes, including any of the catheter types or shapes shown in other figures herein. The catheter kit 48 includes equipment for performing the steps of the method, as at least above described. By example only, the catheter kit 48 includes two stylets 24A, 24B, two guide-wires 26A, 26B, a "6-French" sheath/dilator 54, and two vessel dilators 56, 58, each of the vessel dilators having a distinct size from the other vessel dilator. Other arrangements are contemplated and are within the scope of the present disclosure, each having at least two stylets 24A, 24B. For example, in one embodiment, the catheter kit 48 includes a catheter body 12 having a split-tip catheter and two stylets 24A, 24B. The catheter kit 48 is suitable for inserting either antegrade or retrograde catheter configurations, in accordance with at least one embodiment of the present disclosure.

Still referring to FIG. 12, stylets 24A, 24B are illustrated as "5-French" in size and of the same length, by example only. However, stylets 24A, 24B need not be of the same size and length, but can be selected according to the size and length of the catheter to be inserted. Further, stylets 24A, 24B need not have a round exterior shape, but rather, can have an external shape according to the size and shape of an interior of a catheter lumen 14A, 14B, for example, oval shaped. In a preferred embodiment, each stylet 24A, 24B has a tapered configuration along a distal portion to aid in dilating the catheter lumen 14A, 14B, with a releasable coupler 60 at a proximal end 59, such as a luer-coupler. Each stylet 24A, 24B has a hollow bore for accommodating a lumen running along its length sized to slidably receive a guide-wire 26A, 26B as above described. Each stylet 24A, 24B preferably has a stiffness in a range that is sufficient to prevent the catheter body 12 from kinking or otherwise distorting during the insertion procedure. The stylets 24A, 24B can be components in the catheter kit 48, be separately provided, or be predisposed within the catheter lumens 14A, 14B.

Still referring to FIG. 12, the guide-wires 26A, 26B are illustrated as "J-straight" 0.038-inch guide-wires by example only; however, each guide-wire 26A, 26B can vary according to the application and catheter configuration. Each guide-wire 26A, 26B can have a removable sheath to accommodate handling and facilitate placement within a desired location such as a vein. The sheath/dilator 54 is illustrated as having size of "6-French;" however, other sizes may be used to puncture a wall of a vessel and accommodate one or more guide-wires 26A, 26B. The dilators 56, 58 are illustrated as having size of "14-French" and "16-French," respectively; and the dilators 56, 58 are suitable for many catheter insertion procedures. In a preferred embodiment, a size of "12-French" is provided in addition to, or instead of, one of the illustrated dilators 56, 58. The above apparatuses, systems, methods, and kits are useful for inserting hemodialysis catheters in a patient, and, in general, for multi-lumen split-tip catheters intended for other functions where body fluids are extracted and introduced. As such, the present disclosure is not limited to those embodiments described above, but rather, is limited by the claims that follow.

FIGS. 13-18 show distal ends of additional catheters for use with the intra-catheter stiffener elements, stylets, and guide-wires described herein in embodiments of a catheter insertion system. The catheter insertion systems can be included in catheter kits such as those described herein.

Figure 13:
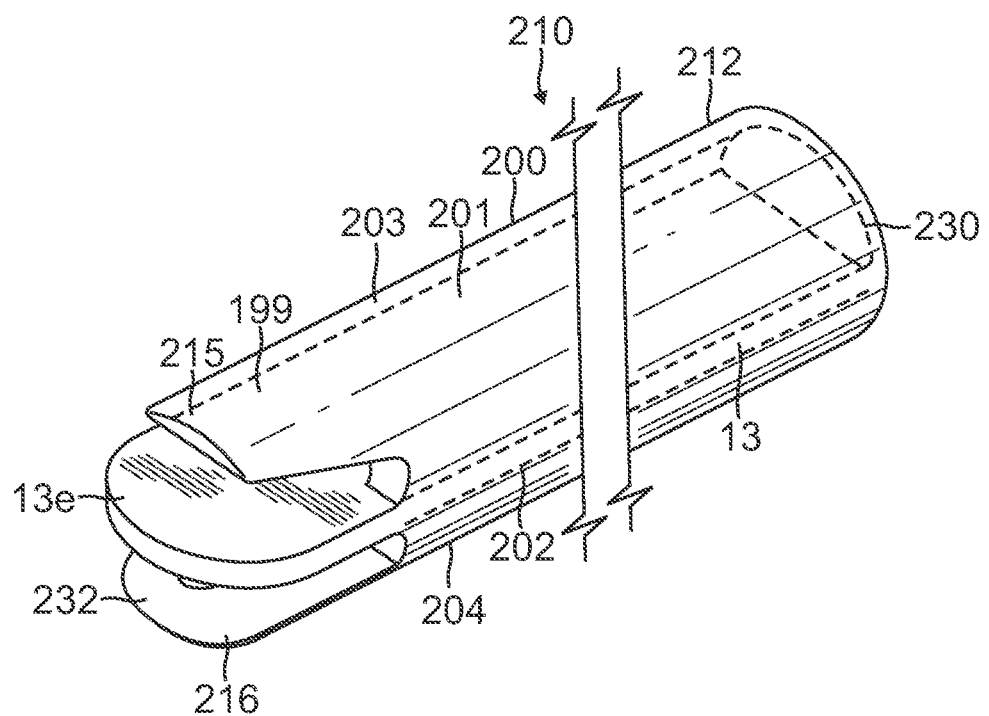
FIG. 13 is a schematic diagram illustrating a perspective view of a catheter apparatus, e.g., of a catheter insertion system, in accordance with an embodiment of the present disclosure.
Figure 14:
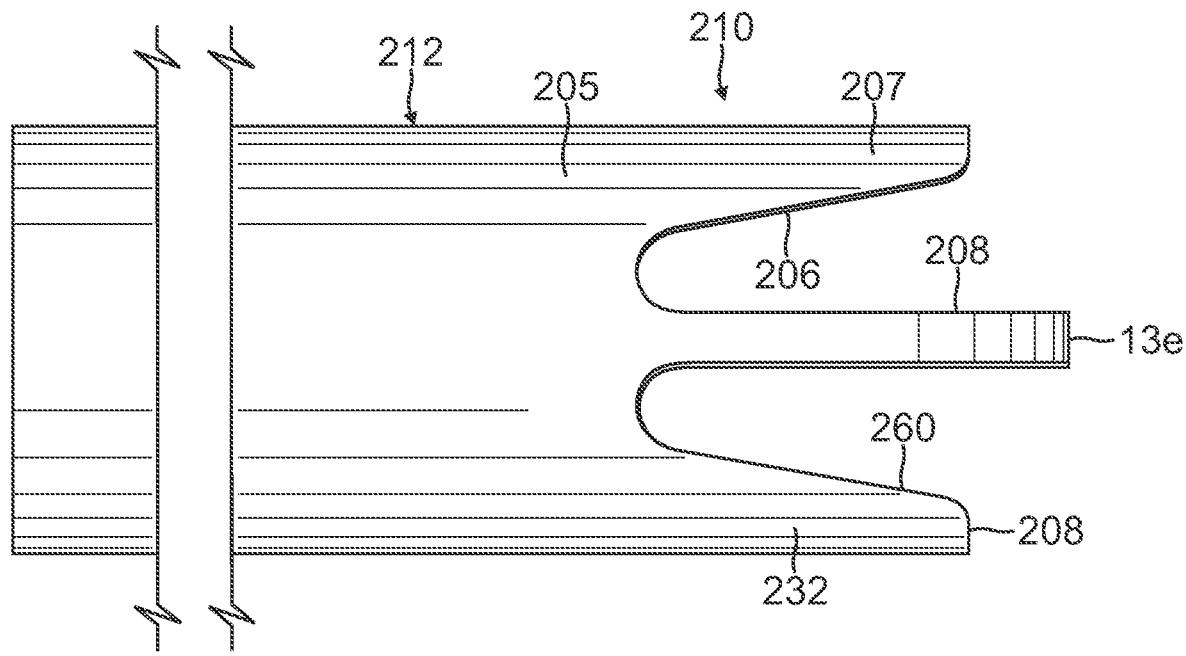
FIG. 14 is a schematic diagram illustrating a side view of a catheter apparatus, e.g., of a catheter insertion system, in accordance with an embodiment of the present disclosure.

Referring to FIGS. 13 and 14, these schematic diagrams respectively illustrate a perspective view and a side view of a catheter apparatus 210 of a catheter insertion system, in accordance with an embodiment of the present disclosure. The catheter apparatus 210 includes a catheter body 212 having an elongated tubular configuration that extends to a distal end 199. A catheter body 212 has a first lumen 201 and a second lumen 202, with a septum 13 disposed therebetween. The catheter body 212 includes a first wall 203 that defines first lumen 201 and a second wall 204 that defines the second lumen 202. A portion, such as a septum extension 13e of the septum 13 extends distally beyond the first lumen 201 and the second lumen 204. The septum 13 is medially disposed along a substantial portion of the longitudinal length of the catheter body 212, between the first lumen 201 and second lumen 202. The septum 13 is variously disposed in relation to the catheter body 212, such as by an angular offset relative to extended portions of the first and second walls 203, 204.

The first wall 203 includes a first wall extension 215 that extends distally beyond first lumen 201 and is spaced apart from septum extension 13e. The first wall extension 215 defines a concave surface 230 that faces septum extension 13e. The second wall 204 includes a second wall extension 232 that extends distally beyond second lumen 204 and is spaced apart from septum extension 13e. The second wall extension defines a concave surface 230 that faces septum extension 13e. The septum extension 13e extends beyond the first wall extension 215 and second wall extension 232. The septum extension 13e is medially disposed, as extending from the catheter body 212, between the first wall extension and the second wall extension. The septum extension 13e is variously disposed in relation to the catheter body 212. The catheter apparatus 210 advantageously prevents occlusion of the first lumen 201 and second lumen 202. One or a plurality of wall extensions may be employed with catheter insertion system, depending on a given catheter application.

The catheter body 212 includes a monocoque configuration, such as a cylindrical outer surface 205. The catheter body 212 is variously dimensioned and attachable to other medical devices. The outer surface 205 includes various cross-sectional configurations, such as an oval shape, a rectangular shape, an elliptical shape, a polygonal shape, etc. The catheter body 212 may also include lateral openings. The first wall 203 has a wall surface that defines the first lumen 201 in cooperation with a surface of the septum 13. The second wall 204 has a wall surface that defines the second lumen 202 in cooperation with a surface of the septum 13.

The concave surface 230 is bounded by a planar end surface 206 of first wall extension and spans a radial distance. The planar end surface 206 extends about the perimeter of the concave surface 230, such that first wall extension 215 has a scoop-shape configuration that facilitates fluid flow through the first lumen 201. The first wall extension 215 may form alternate configurations, such as a spherical shape, a rectangular shape, etc. The planar end surface 206 includes a radial portion adjacent a distal end of first wall extension 215. The radial portion extends to the longitudinally oriented outer surface 200 of the catheter body 212 in an arcuate configuration. This configuration advantageously prevents a blood vessel wall (not shown) from becoming disposed within the inlet of first lumen 201. A radial portion 207 extends to the longitudinally oriented outer surface 200 of the catheter body 212 in a perpendicular convergence. The planar end surface 206 is disposed at an angular orientation a relative to a first planar surface 208. The planar end surface 206 may be disposed at various angular orientations. A concave surface 230 is bounded by a planar end surface 260 of second wall extension 232 and spans a radial distance. End surface 260 extends about the perimeter of concave surface 230 such that the second wall extension 232 has a scoop-like configuration that facilitates fluid flow through second lumen 202.

The catheter apparatus 210 may be used in place of, in addition to, or in combination with the catheter apparatus 12 (of FIGS. 1-12) or other catheter apparatuses disclosed herein. Catheter systems, comprising a catheter apparatus 210, are combinable with the features described with respect to other catheter apparatuses herein, in accordance with described embodiments of catheter systems. For example, embodiments of the intra-catheter stiffener elements described herein may be configured/shaped in such a way for disposition through the lumens 201, 202. A first intra-catheter stiffener element 51A may be configured/shaped for disposition through the first lumen 201 such that a distal end thereof is distal in relation to the distal end 199. A second intra-catheter stiffener element 51B may be configured/shaped for disposition through the second lumen 202 such that a distal end thereof is also distal in relation to the distal end 199. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Figure 15:
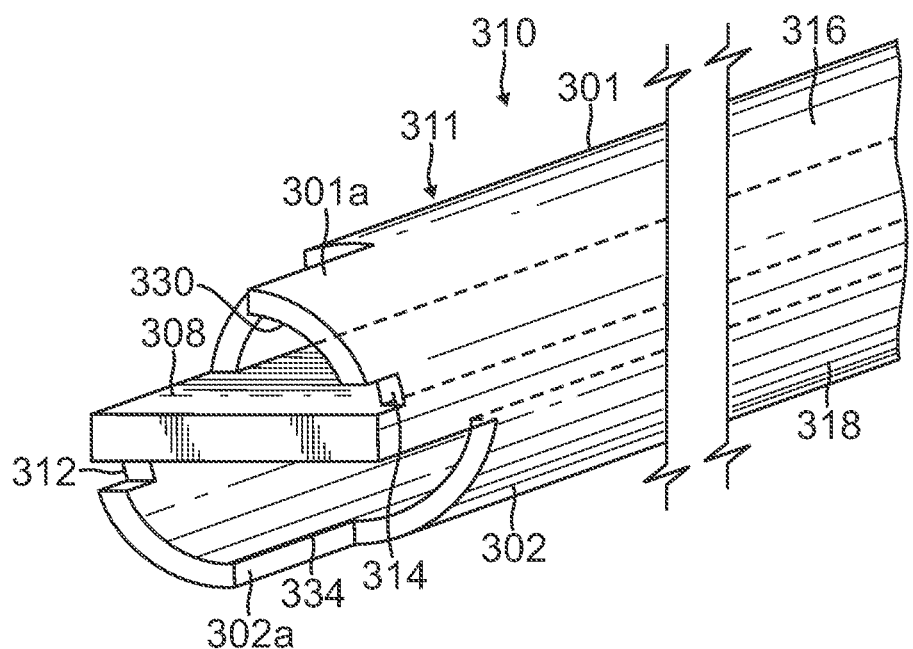
FIG. 15 is a schematic diagram illustrating a perspective view of a catheter apparatus, e.g., of a catheter insertion system, in accordance with an embodiment of the present disclosure.
Figure 16:
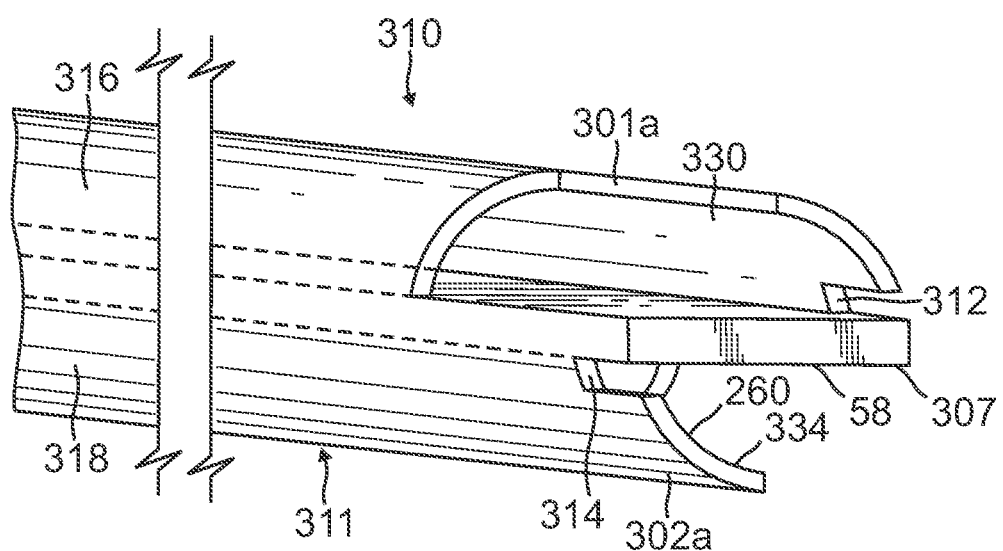
FIG. 16 is a schematic diagram illustrating a perspective view of a catheter apparatus, e.g., of a catheter insertion system, in accordance with an embodiment of the present disclosure.

Referring to FIGS. 15 and 16, these schematic diagrams illustrate, in various perspective views, catheter systems that are combinable with many of the above-described features. A catheter apparatus 310 includes a first wall 301 that includes a first wall extension 301a that extends distally beyond a first lumen 316 and is spaced apart from a septum extension 307. The first wall extension 301a defines a concave surface 330 that faces the septum extension 307. A second wall 302 includes a second wall extension 302a that extends distally beyond a second lumen 318 and is spaced apart from the septum extension 307. The second wall extension 302a defines a concave surface 334 that faces the septum extension 307.

The first wall extension 301a includes a first step or notch 312 and a second step or notch 314 formed therewith. The first step or notch 312 is formed with the septum extension 307. The first step or notch 312 and the second step or notch 314 are circumferentially disposed about the septum extension 307. The first step or notch 312 and/or the second step or notch 314 may have alternate configurations, such as a planar configuration, etc. The first step or notch 312 extends distally beyond an inlet opening of the first lumen 316 and an outlet opening of the second lumen 318. The second step or notch 314 extends distally beyond the inlet opening and the outlet opening. A concave surface 230 faces a first planar surface 308 of the septum extension 307 and is spaced apart therefrom. A concave surface 330 spans across approximately one-quarter of the circumference of the catheter body 311 or a substantially 90° arc as extended from the septum extension 307. The first step or notch 312 and/or the second step or notch 314, or other portions of the concave surface 330 may be variously disposed about the catheter body 311.

The catheter apparatus 310 may be used in place of, in addition to, or in combination with the catheter apparatus 12 (of FIGS. 1-12) or other catheter apparatuses disclosed herein. Catheter systems, comprising a catheter apparatus 310, are combinable with the features described with respect to other catheter apparatuses herein, in accordance with described embodiments of catheter systems. For example, embodiments of the intra-catheter stiffener elements described herein may be configured/shaped in such a way for disposition through the lumens 316, 318. A first intra-catheter stiffener element 51A may be configured/shaped for disposition through the first lumen 316 such that a distal end thereof is distal in relation to the septum extension 307. A second intra-catheter stiffener element 51B may be configured/shaped for disposition through the second lumen 202 such that a distal end thereof is also distal in relation to the septum extension 307. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Figure 17:
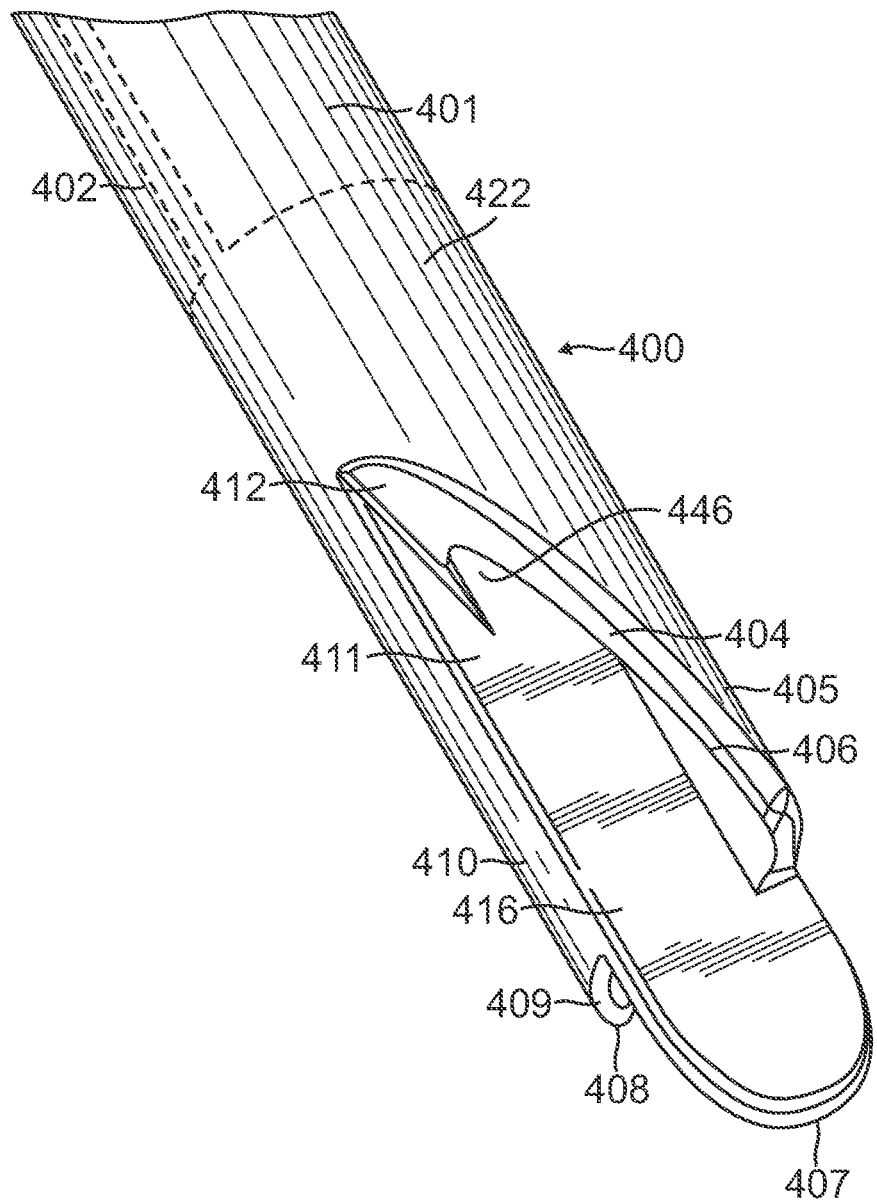
FIG. 17 is a schematic diagram illustrating a perspective view of a catheter apparatus, e.g., of a catheter insertion system, in accordance with an embodiment of the present disclosure.
Figure 18:
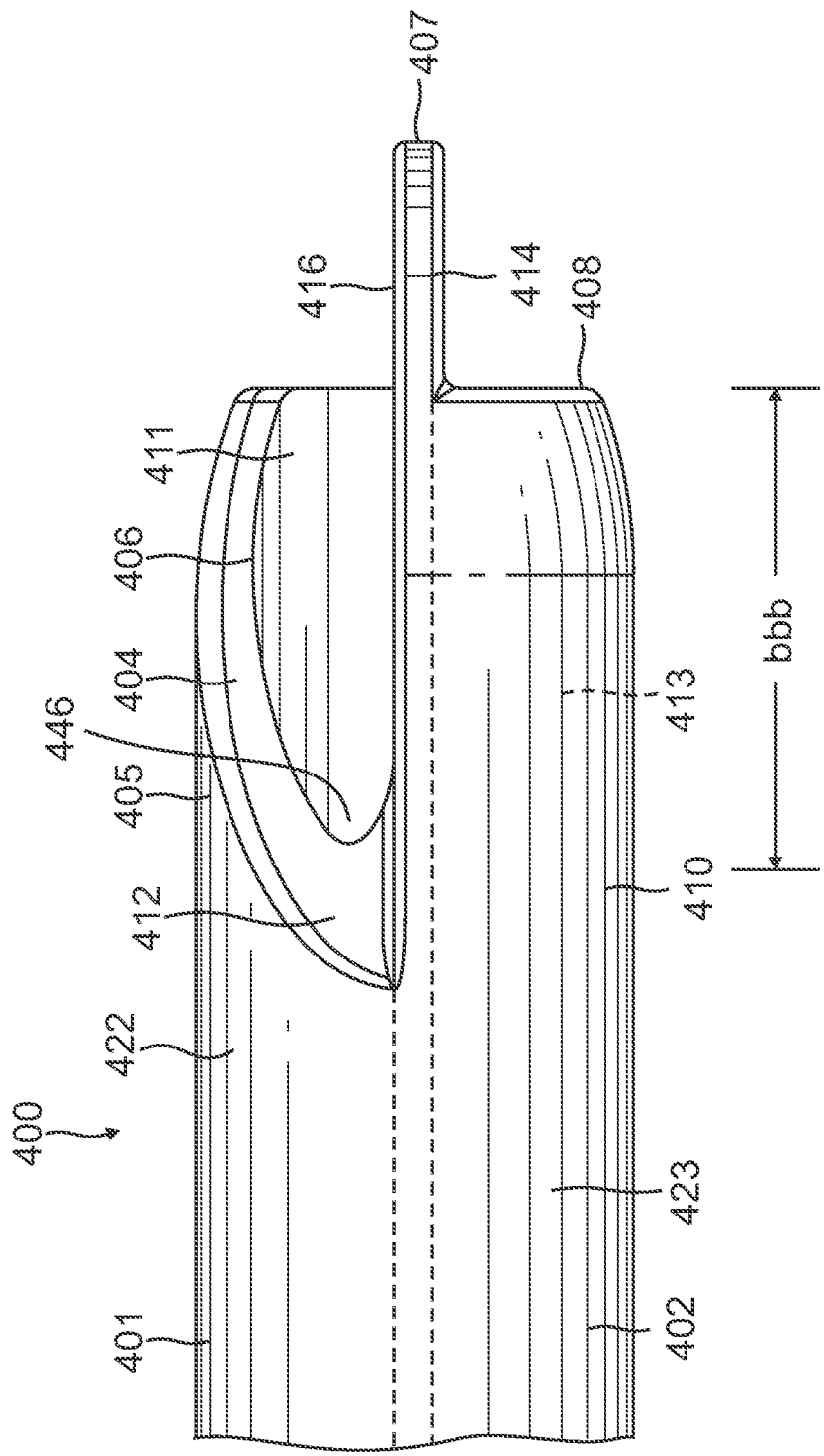
FIG. 18 is a schematic diagram illustrating a perspective view of a catheter apparatus, e.g., of a catheter insertion system, in accordance with an embodiment of the present disclosure.

Referring to FIGS. 17 and 18, these schematic diagrams illustrate, in various perspective views, catheter systems comprising a catheter apparatus 400 that are combinable with features described in various embodiments of the present disclosure. The distal end of the catheter apparatus 400 includes a first wall 422 having a first wall extension 405 that extends distally beyond venous lumen 401 and is spaced apart from a septum extension 407. First wall extension 405 defines a concave surface 406 that faces septum extension 407. A second wall 423 includes a second wall extension 410 that extends distally beyond arterial lumen 402 and is spaced apart from septum extension 407. Second wall extension 410 defines a concave surface 409 that faces septum extension 407.

The first wall extension 405 is circumferentially disposed about septum extension 407 in a spiral configuration to facilitate fluid flow and prevent recirculation between lumens 401, 402. The first wall extension 405 may include various spiral configurations, such as, for example, a more elongated spiral, a spiral having a more acute winding type design, helical, etc. First wall extension 405 extends distally beyond opening 446 of the first lumen 401 and opening 450 (not shown) of second lumen 402. A concave surface 406 faces first planar surface 416 of septum extension 407 and is spaced apart therefrom. A concave surface 406 is bounded by a planar end surface 404 of first wall extension 405. End surface 404 extends about the perimeter of concave surface 406 in a spiral configuration, as described above, to facilitate fluid flow through venous lumen 401. Concave surface 406 and first planar surface 416 cooperate to define first cavity 411. First cavity 411 is further bounded by a proximal base 412 of end surface 404. Proximal base 412 is formed with septum extension 407 in an arcuate transition. Proximal base 412 has an arcuate configuration and defines a proximal inlet/outlet portion for venous lumen 401. During removal of fluids, venous lumen 401 has a greater fluid flow rate adjacent proximal base 412.

A second wall extension 410 is circumferentially disposed about septum extension 407 in a spiral configuration to facilitate fluid flow and prevent recirculation between lumens 401, 402. The first wall extension 405 may include various spiral configurations, such as, for example, a more elongated spiral, a spiral having a more acute winding type design, helical, etc. Second wall extension 410 extends distally, a distance bbb, beyond opening 450 (not shown but similarly configured to opening 446) and opening 446. The distance bbb includes various lengths. Concave surface 409 faces second planar surface 414, opposing first planar surface 416, of septum extension 407 and is spaced apart therefrom. Concave surface 409 is bounded by a planar end surface 408 of second wall extension 410. End surface 408 (similarly configured to end surface 404, although end surfaces 404, 408 may include alternative or distinct structure) extends about the perimeter of concave surface 409 in a spiral configuration, as described above, to facilitate fluid flow through arterial lumen 402. Concave surface 409 and second planar surface 414 cooperate to define second cavity 413 (shown in phantom), similar to that described above. Second cavity 413 is further bounded by a proximal base of end surface 408, which can be similarly configured to base 412, although the bases 412 may include alternative or distinct structure. Proximal base has an arcuate configuration and defines a proximal inlet/outlet portion for arterial lumen 402 during removal of fluids. It is contemplated that that during removal of fluids, arterial lumen 402 has a greater fluid flow rate adjacent proximal base.

A first wall extension 405 and second wall extension 410 are symmetrically disposed about septum extension 407 such that first cavity 411 and second cavity 413 are symmetrical. First cavity 411 and second cavity 413 bound an equivalent space to facilitate inflow and outflow capability for each lumen. The configuration of the catheter apparatus 400 advantageously facilitates reversible flow between venous lumen 401 and arterial lumen 402 by alternating blood flow directions. As venous lumen 401 returns blood flow to the body vessel, blood flow is removed through arterial lumen 402. The blood flow is axially directed out of cavity 411 past first wall extension 406. Such axially directed blood flow washes away any blood clots disposed adjacent cavity 411. Arterial lumen 402 is provided with suction to remove fluids from the body vessel. The suction draws blood flow from various directions and orientations into opening 450. Suction is greater adjacent proximal base due to its closer proximity to a suction source (not shown). Fluid flow is greater adjacent to proximal base and therefore, advantageously disposed proximal to the blood flow being expelled from cavity 411 of venous lumen 401. This configuration minimizes recirculation between lumens 401, 402. It is contemplated that blood clots, or other undesired particles, disposed adjacent cavity 413 of arterial lumen 402 may be washed away by reversing blood flow direction of lumens 401, 402. Upon reversal of blood flow direction, blood flow is expelled from cavity 413 and the axially directed blood flow washes away blood clots, similar to that described above. Venous lumen 401 removes fluids from the body vessel and into opening 411. Second wall extension 410 is symmetrical with first wall extension 405, and therefore, similar to proximal base, suction is greater adjacent proximal base 412. Fluid flow is greater adjacent to proximal base 412 and therefore, advantageously disposed proximal to the blood flow being expelled from cavity 413. This configuration minimizes recirculation between lumens 401, 402.

The catheter apparatus 400 may be used in place of, in addition to, or in combination with the catheter apparatus 12 (of FIGS. 1-12) or other catheter apparatuses disclosed herein. Catheter systems, comprising a catheter apparatus 400, are combinable with the features described with respect to other catheter apparatuses herein, in accordance with described embodiments of catheter systems. For example, embodiments of the intra-catheter stiffener elements described herein may be configured/shaped in such a way for disposition through the lumens 401, 402. A first intra-catheter stiffener element 51A may be configured/shaped for disposition through the first lumen 401 such that a distal end thereof is distal in relation to the distal end of septum 407. A second intra-catheter stiffener element 51B may be configured/shaped for disposition through the second lumen 202 such that a distal end thereof is also distal in relation to the distal end of septum 407. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Figure 19:
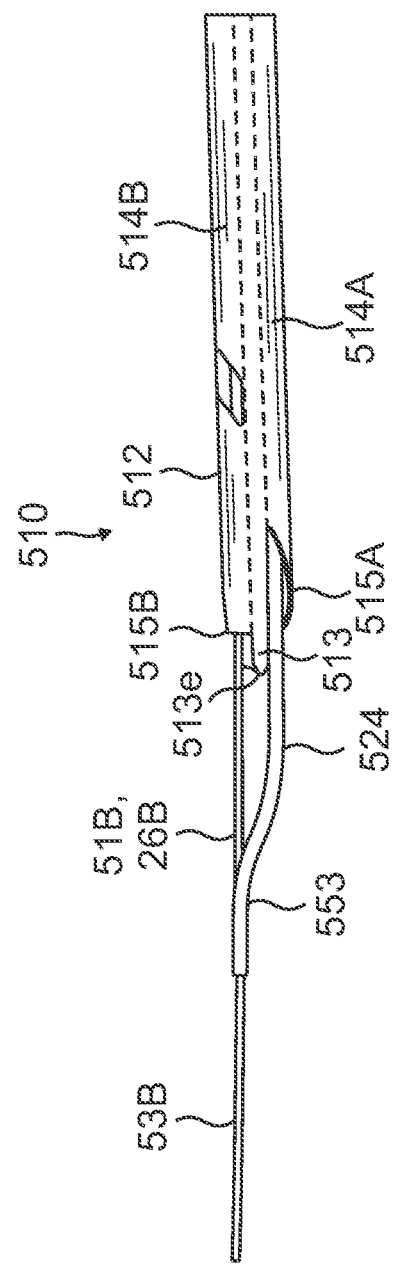
FIG. 19 is a schematic diagram illustrating a cutaway side view of a catheter apparatus, e.g., of a catheter insertion system, comprising a catheter body having two lumens, a single stylet disposed through one lumen; and a single guide-wire disposed through the other lumen, a distal end of the guide-wire being disposed through a distal end of the stylet, such as useable in a catheter system, in accordance with an embodiment of the present disclosure.

Referring to FIG. 19, this schematic diagram illustrates, in a cutaway side view, first and second intra-catheter stiffener elements in a catheter similar to the catheters of FIGS. 13-18, which include a septum extension. A catheter apparatus 510 includes septum extension 513e, a catheter body 512 having two lumens 514A, 514B, a single stylet 524 disposed through one lumen 514A and a single guide-wire 26B disposed through the other lumen 514B. A distal end 53B of the guide-wire 26B is disposed through a distal end 553 of the stylet 524, by example only, in accordance with an embodiment of the present disclosure. The catheter apparatus 510 includes: a catheter body 512 comprising a first lumen 514A capable of fluid communication via a first distal opening 515A and a second lumen 514B capable of fluid communication via a second distal opening 515B; a first intra-catheter stiffener element, such as stylet 524, configured for disposition through the first lumen 514A such that a distal end 553 thereof is distal in relation to the first distal opening 515A, the first intra-catheter stiffener element 51A comprising one of a guide-wire 26A and a stylet 24A (FIGS. 1-12); and a second intra-catheter stiffener element 51B configured for disposition through the second lumen 514B such that a distal end 53B thereof is distal in relation to the second distal opening 515B, the second intra-catheter stiffener element 51B comprising a guide-wire 26B, one of the first intra-catheter stiffener element distal end 553 and the second intra-catheter stiffener element distal end 53B capable of receiving and accommodating the other of the first intra-catheter stiffener element distal end 553 and the second intra-catheter stiffener element distal end 53B, in accordance with an embodiment of the present disclosure.

Referring to, the first and second intra-catheter stiffener elements herein, the second intra-catheter stiffener element includes at least one of an eye portion (not shown) and a looped portion, such as looped portion 755 (FIGS. 21A and 21B), disposed at the distal end 53A thereof capable of receiving and facilitating disposition therethrough of the distal end 53B of the other of the first intra-catheter stiffener element and the second intra-catheter stiffener element. The catheter body includes a septum for separating the first lumen and the second lumen from one another, the septum having a distal end extending beyond at least one of the first distal opening and the second distal opening for at least minimizing backflow into at least one of the first lumen and the second lumen.

The intra-catheter stiffener elements described herein may be configured in such a way for disposition within the lumens of any of the catheter systems described within the present disclosure. The distal end of the first intra-catheter stiffener element 53B may be configured such that it is distal in relation to the septum extension 113e and a distal end of the second intra-catheter stiffener element 553 may be configured such that it is also distal in relation to the distal end of septum extension 113e. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Referring to FIG. 20A, this schematic diagram illustrates, in a cutaway top view, a catheter apparatus 610, comprising a catheter body 612 having two lumens 614A, 614B separated by a septum 613, a first intra-catheter stiffener element, such as a single stylet 651, disposed through one lumen 614A; and second intra-catheter stiffener element 51B, such as a single guide-wire 26B (not shown), disposed through the other lumen 614B, a distal end 53B of the guide-wire 26B (not shown) being disposable within at least one portion of the stylet 651, such as useable in a catheter system, in accordance with an embodiment of the present disclosure. The stylet 651 is configured for inserting and translating through a lumen, such as a first lumen 614A, for rotation, such as after insertion and translation, wherein a notched portion 660 of the stylet distal portion, e.g., a cover portion 657, is rotatable for receiving the septum 613, whereby further structural support is provided for enhancing stiffening and guiding of the catheter body 612, and for receiving a guide-wire, such as by way of a distal end 53B of the guide-wire 26B (not shown).

Referring to FIG. 20B, this schematic diagram illustrates, in a cutaway side view, a catheter apparatus 610, comprising a catheter body 612 having two lumens 614A, 614B separated by a septum 613, a first intra-catheter stiffener element, such as a single stylet 651, disposed through one lumen 614A; and second intra-catheter stiffener element 51B, such as a single guide-wire 26B, disposed through the other lumen 614B, a distal end 53B of the guide-wire 26B being disposable within at least one portion of the stylet 651, such as useable in a catheter system, in accordance with an embodiment of the present disclosure. Optionally, the guide-wire 26B may be woven into the stylet 651 along at least a portion of the stylet 651, whereby a smooth transition is provided for enhancing stiffening and guiding of the catheter body 612.

Still referring to FIGS. 20A and 20B, the first intra-catheter stiffener element 651 includes a cover portion 657 at the distal end 653 thereof, the cover portion 657 capable of deployment and retraction in relation to one of the first lumen 614A and the second lumen 614B, and the cover portion 657 cooperatively engageable with the septum distal end 613e for at least minimizing backflow into the one of the first lumen 614A and the second lumen 614B, in accordance with an embodiment of the present disclosure. The cover portion 657 is deployable and retractable via at least one technique of a rotation and a translation in relation to a longitudinal axis A thereof. The first intra-catheter stiffener element 51A, such as a stylet, includes at least one of a monolithic configuration and a tapered configuration, wherein the first intra-catheter stiffener element 51A includes a first length, wherein the second intra-catheter stiffener element 51B includes a second length, the second length less than the first length. The cover portion 657 optionally includes at least one of a conical configuration and an oval cross-section. The stylet, such as the stylet 24A, includes an outer dimensions or sizes that conforms with a lumen's inner dimensions or sizes.

The intra-catheter stiffener elements described herein may be configured in such a way for disposition within the lumens of any of the catheter systems described within the present disclosure. The distal end of the first intra-catheter stiffener element 653 may be configured such that it is distal in relation to the septum extension 613e and a distal end of the second intra-catheter stiffener element (not shown) may be configured such that it is also distal in relation to the distal end of septum extension 613e. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Referring to FIG. 21A, this schematic diagram illustrates, in a cutaway top view, a catheter apparatus 710, comprising a catheter body 712 having two lumens (not shown) separated by a septum (not shown) with a distal end of septum 713e, a first intra-catheter stiffener element 751, such as a guide-wire 752, disposed through a first lumen (not shown); a second intra-catheter stiffener element 51B, such as a guide-wire 26B, disposed through a second lumen (not shown); a distal end 53B of one guide-wire 26B being disposable through a distal end 753 of the other guide-wire 752, wherein the other guide-wire distal end includes a looped portion 755, such as useable in a catheter system, in accordance with an embodiment of the present disclosure. Optionally, at least one of the guide-wires 752, 26B includes a coating, the coating comprising at least one material having a low friction coefficient, such as a fluorinated polymer, e.g., polyvinylfluoride (PVF), polyvinylidene fluoride (PVDF), tetrafluoroethylene (TFE), polytetrafluoroethylene (PTFE), polychlorotrifluoroethylene (PCTFE), perfluoroalkoxy polymer (PFA, MFA), fluorinated ethylenepropylene (FEP), polyethylenetetrafluoroethylene (ETFE), polyethylenechlorotrifluoroethylene (ECTFE), perfluorinated plastomer [perfluoroelastomer] (FFPM/FFKM), fluorocarbon [chlorotrifluoroethylenevinylidene fluoride] (FPM/FKM), perfluoropolyether (PFPE), perfluorosulfonic acid (PFSA), perfluoropolyoxetane, a fluorinated hyper-branched polymer, and/or a smooth silicone material, and the like.

Referring to FIG. 21B, this schematic diagram illustrates, in a cutaway side view, a catheter apparatus 710, comprising a catheter body 712 having two lumens (not shown) separated by a septum (not shown) with a distal end of septum 713e, a first intra-catheter stiffener element 751, such as a guide-wire 752, disposed through a first lumen 14A; a second intra-catheter stiffener element 51B, such as a guide-wire 26B, disposed through a second lumen 14B; a distal end 53B of one guide-wire 26B being disposable through a distal end 753 of the other guide-wire 752, wherein the other guide-wire distal end includes a looped portion 755, such as useable in a catheter system, in accordance with an embodiment of the present disclosure.

The intra-catheter stiffener elements described herein may be configured in such a way for disposition within the lumens of any of the catheter systems described within the present disclosure. The distal end of the first intra-catheter stiffener element 53B may be configured such that it is distal in relation to the septum extension 713e and a distal end of the second intra-catheter stiffener element 751 may be configured such that it is also distal in relation to the distal end of septum extension 713e. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Referring back to FIGS. 19 through 21B, the first intra-catheter stiffener element includes a first coupler, such as a fluid-coupler, at a proximal end thereof; and the second intra-catheter stiffener element includes a second coupler, such as a fluid-coupler, at a proximal end thereof, wherein the distal end of the first intra-catheter stiffener element is distal in relation to the distal end of the second intra-catheter stiffener element when the first coupler and second coupler are coupled to the catheter body, wherein the first coupler of the first intra-catheter stiffener element mates with a first mating coupler (not shown) at a first proximal opening of the catheter body, and wherein the second coupler of the second intra-catheter stiffener element mates with a second mating coupler (not shown) at a second proximal opening of the catheter body.

The first intra-catheter stiffener elements herein may include an exterior cross-sectional shape complementing an interior cross-sectional shape of the first lumen; and the second intra-catheter stiffener element may include an exterior cross-sectional shape complementing an interior cross-sectional shape of the second lumen, wherein the exterior cross-sectional shape of the first intra-catheter stiffener element includes one of a round shape, an oval shape, an elliptical shape, and an ogivoidal shape, and wherein the exterior cross-sectional shape of the second intra-catheter stiffener element includes one of a round shape, an oval shape, an elliptical shape, and an ogivoidal shape. Other cross-sectional shapes are contemplated and are within the scope of the present disclosure.

Figure 22:
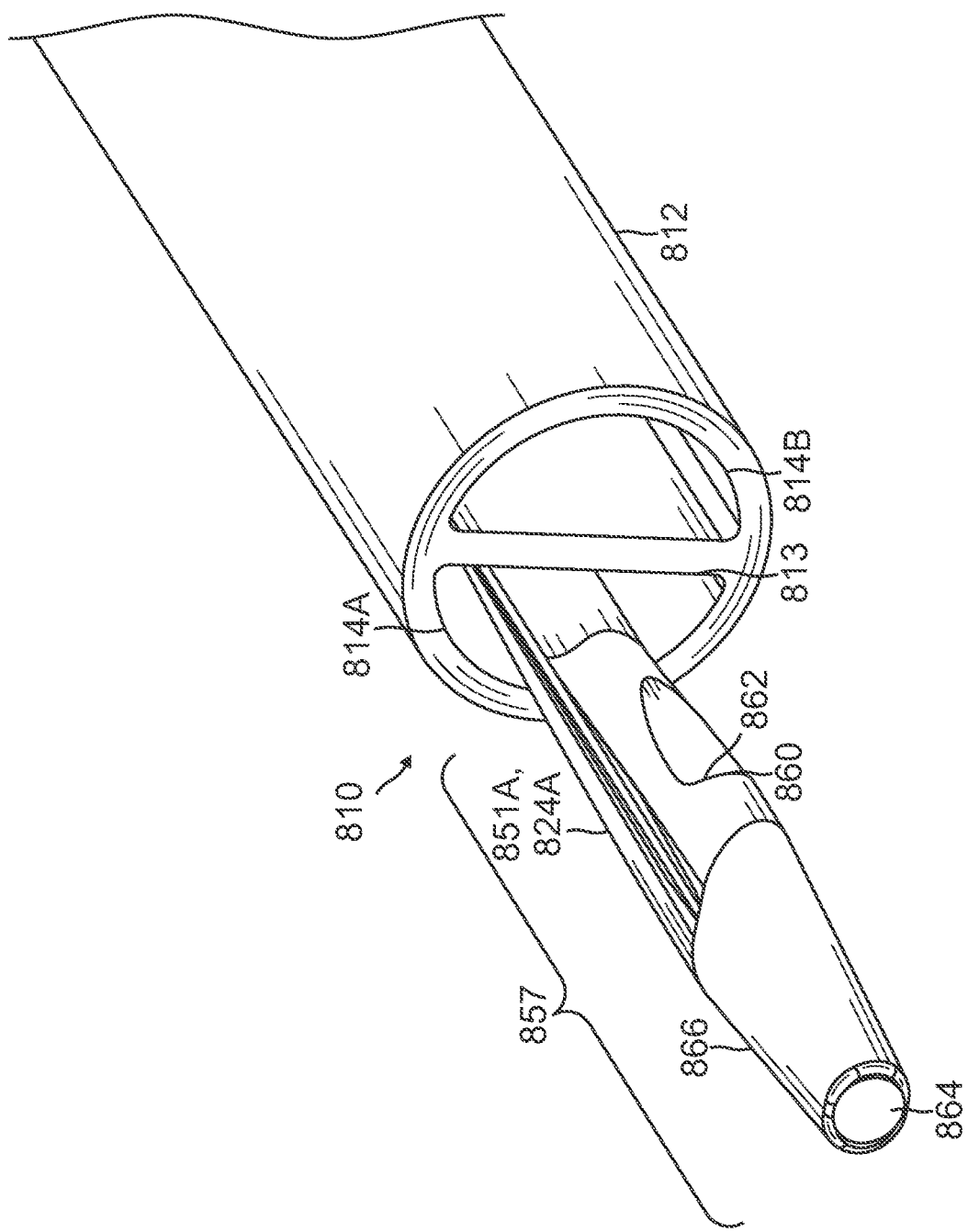
FIG. 22 is schematic diagram illustrating a cutaway perspective view of a catheter apparatus, e.g., of a catheter insertion system, wherein a stylet is adapted to accommodate a guide-wire, such as by weaving through a portion thereof, in accordance with an embodiment of the present disclosure.

Referring to FIG. 22, this schematic diagram illustrates, in a cutaway perspective view, a catheter apparatus 810 of a catheter insertion system, comprising a catheter body 812 having two lumens 814A, 814B separated by a septum 813, a first intra-catheter stiffener element 851A, such as a single stylet 824A, disposed through one lumen 814A; and second intra-catheter stiffener element 51B, such as a single guide-wire 26B (FIGS. 24 and 25), disposable through the other lumen 814B, a distal end 53B of the guide-wire 26B (FIGS. 24 and 25) being disposable within at least one portion of the stylet 824A, such as useable in a catheter system, in accordance with an embodiment of the present disclosure.

The guide-wire 26B is insertable, e.g., "weavable" or "threadable," into the stylet 824A along at least a portion thereof, whereby a smooth transition is provided for enhancing stiffening and guiding of the catheter body 812. The stylet 824A is configured for inserting and translating through a lumen, such as the lumen 814A or the lumen 814B, for rotation, such as after insertion and translation, wherein a notched portion 860 of the stylet distal portion, e.g., a cover or overhang portion 857, is rotatable for optionally receiving the septum 813, e.g., if the septum 813 includes a septum distal end 13e extending from the septum 813 (FIGS. 13-15B), whereby further structural support is provided for enhancing stiffening and guiding of the catheter body 812, and for receiving a guide-wire (FIGS. 24 and 25), such as by way of a distal end 53B of the guide-wire 26B through a first orifice 862 and a second orifice 864 of the first intra-catheter stiffener element 851A, such as a single stylet 824A.

Figure 23:
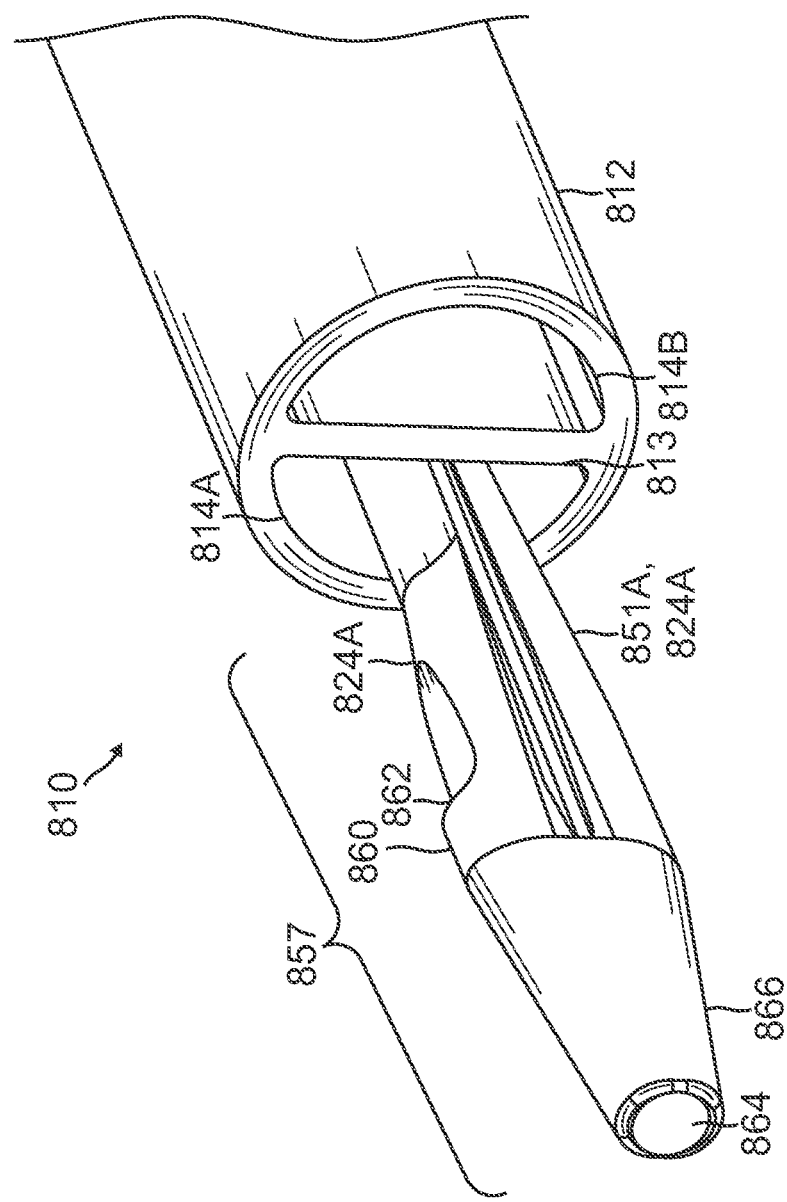
FIG. 23 is schematic diagram illustrating another cutaway perspective view of the catheter apparatus, e.g., of a catheter insertion system, as shown in FIG. 22, wherein a stylet is adapted to accommodate a guide-wire, such as by weaving through a portion thereof, in accordance with an embodiment of the present disclosure.
Figure 24:
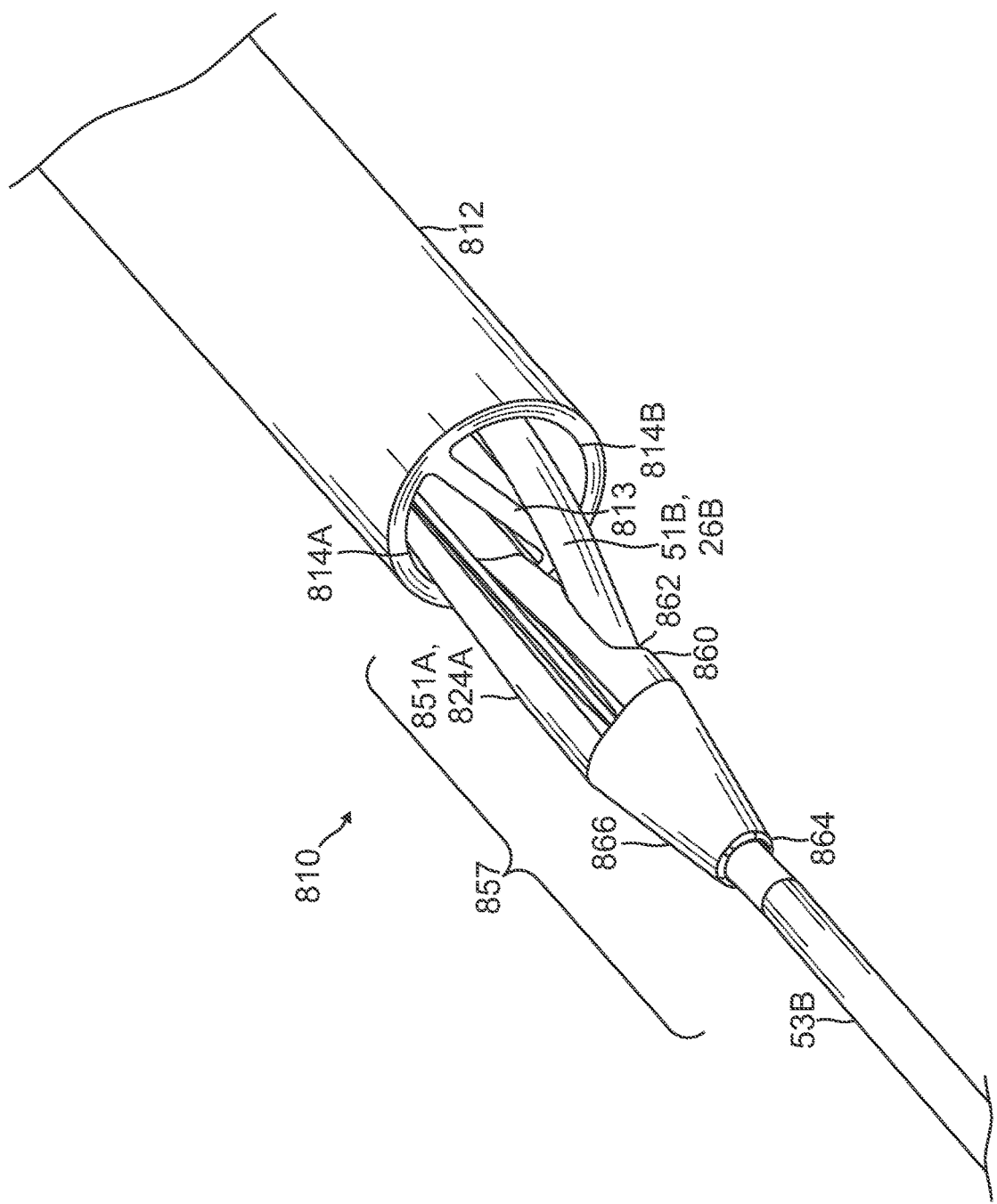
FIG. 24 is schematic diagram illustrating a cutaway perspective view of a catheter apparatus, e.g., of a catheter insertion system, wherein a guide-wire is woven through a portion of a stylet, in accordance with an embodiment of the present disclosure.

Referring to FIG. 23, this schematic diagram illustrates, in another cutaway perspective view, the catheter apparatus 810 of a catheter insertion system, as shown in FIG. 24, comprising a catheter body 812 having two lumens 814A, 814B separated by a septum 813, a first intra-catheter stiffener element 851A, such as a single stylet 824A, disposed through one lumen 814A; and second intra-catheter stiffener element 51B, such as a single guide-wire 26B (FIGS. 24 and 25), disposable through the other lumen 814B, a distal end 53B of the guide-wire 26B (FIGS. 24 and 25) being disposable within at least one portion of the stylet 824A, such as useable in a catheter system, in accordance with an embodiment of the present disclosure. The stylet 824A is inserted through one of the catheter lumens 814A, 814B parallel to the septum wall, then rotated prior to guide-wire passage through the distal tip of the stylet 824A.

The guide-wire 26B is insertable, e.g., "weavable" or "threadable," into the stylet 824A along at least a portion thereof, whereby a smooth transition is provided for enhancing stiffening and guiding of the catheter body 812. The stylet 824A is configured for inserting and translating through a lumen, such as the lumen 814A or the lumen 814B, for rotation, such as after insertion and translation, wherein a notched portion 860 of the stylet distal portion, e.g., a cover or overhang portion 857, is rotatable for optionally receiving the septum 813, e.g., if the septum 813 includes a septum distal end 13e extending from the septum 813 (FIGS. 13-15B), whereby further structural support is provided for enhancing stiffening and guiding of the catheter body 812, and for receiving a guide-wire (FIGS. 24 and 25), such as by way of a distal end 53B of the guide-wire 26B through a first orifice 862 and a second orifice 864 of the first intra-catheter stiffener element 851A, such as a single stylet 824A.

One of the first intra-catheter stiffener element 851A and the second intra-catheter stiffener element 51B includes a cover or overhang portion 857 at the distal end 866 thereof, the cover portion 857 capable of deployment and retraction in relation to one of the first lumen 814A and the second lumen 814B, and the cover portion 857 cooperatively engageable with the septum distal end 13e, if any, for at least minimizing backflow into the one of the first lumen 814A and the second lumen 814B, in accordance with an embodiment of the present disclosure. The cover portion 857 is deployable and retractable via at least one technique of a rotation and a translation in relation to a longitudinal axis A thereof (FIGS. 14a and 14B). The first intra-catheter stiffener element 851A, such as a stylet, includes at least one of a monolithic configuration and a tapered configuration, wherein the first intra-catheter stiffener element 851A includes a first length, wherein the second intra-catheter stiffener element 51B includes a second length, the second length less than the first length. The cover portion 857 includes a first orifice 862 and a second orifice 864 for accommodating the guide-wire 26B (FIGS. 24 and 25) and optionally includes at least one of a conical or frusto-conical configuration and an oval cross-section. The stylet, such as the stylet 824A, includes an outer dimensions or sizes that conforms with a lumen's inner dimensions or sizes.

Referring to FIG. 24, this schematic diagram illustrates, in a cutaway perspective view, a catheter apparatus 810 of a catheter insertion system, comprising a catheter body 812 having two lumens 814A, 814B separated by a septum 813, a first intra-catheter stiffener element 851A, such as a single stylet 824A, disposed through one lumen 814A; and second intra-catheter stiffener element 51B, such as a single guide-wire 26B, disposed through the other lumen 814B, a distal end 53B of the guide-wire 26B being disposable within at least one portion of the stylet 824A, such as useable in a catheter system, in accordance with an embodiment of the present disclosure.

The guide-wire 26B is "woven" into the stylet 824A along at least a portion thereof, whereby a smooth transition is provided for enhancing stiffening and guiding of the catheter body 812. The stylet 824A is configured for inserting and translating through a lumen, such as the lumen 814A or the lumen 814B, for rotation, such as after insertion and translation, wherein a notched portion 860 of the stylet distal portion, e.g., a cover or overhang portion 857, is rotatable for optionally receiving the septum 813, e.g., if the septum 813 includes a septum distal end 13e extending from the septum 813 (FIGS. 13-14), whereby further structural support is provided for enhancing stiffening and guiding of the catheter body 812, and for receiving a guide-wire, such as by way of a distal end 53B of the guide-wire 26B through a first orifice 862 and a second orifice 864 of the first intra-catheter stiffener element 851A, such as a single stylet 824A.

Figure 25:
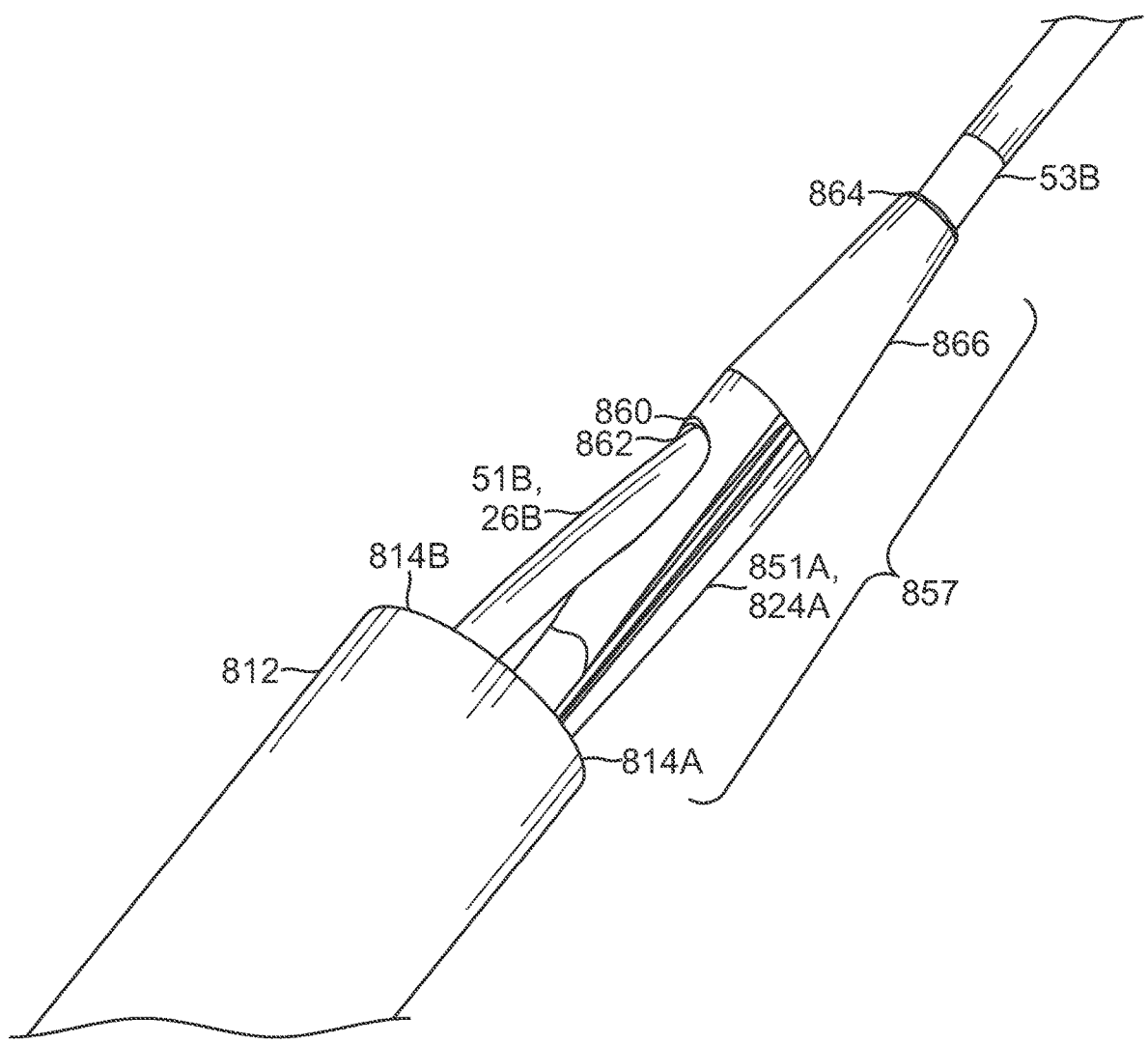
FIG. 25 is schematic diagram illustrating another cutaway perspective view of the catheter apparatus, e.g., of a catheter insertion system, as shown in FIG. 24, wherein a guide-wire is woven through a portion of a stylet, in accordance with an embodiment of the present disclosure.

Referring to FIG. 25, this schematic diagram illustrates, in another cutaway perspective view, the catheter apparatus 810 of a catheter insertion system, as shown in FIG. 24, comprising a catheter body 812 having two lumens 814A, 814B separated by a septum 813, a first intra-catheter stiffener element 851A, such as a single stylet 824A, disposed through one lumen 814A; and second intra-catheter stiffener element 51B, such as a single guide-wire 26B, disposed through the other lumen 814B, a distal end 53B of the guide-wire 26B being disposable within at least one portion of the stylet 824A, such as useable in a catheter system, in accordance with an embodiment of the present disclosure.

The guide-wire 26B is "woven" into the stylet 824A along at least a portion thereof, whereby a smooth transition is provided for enhancing stiffening and guiding of the catheter body 812. The stylet 824A is configured for inserting and translating through a lumen, such as the lumen 814A or the lumen 814B, for rotation, such as after insertion and translation, wherein a notched portion 860 of the stylet distal portion, e.g., a cover or overhang portion 857, is rotatable for optionally receiving the septum 813, e.g., if the septum 813 includes a septum distal end 13e extending from the septum 813 (FIGS. 13-15B), whereby further structural support is provided for enhancing stiffening and guiding of the catheter body 812, and for receiving a guide-wire, such as by way of a distal end 53B of the guide-wire 26B through a first orifice 862 and a second orifice 864 of the first intra-catheter stiffener element 851A, such as a single stylet 824A.

One of the first intra-catheter stiffener element 851A and the second intra-catheter stiffener element 51B includes a cover or overhang portion 857 at the distal end 866 thereof, the cover portion 857 capable of deployment and retraction in relation to one of the first lumen 814A and the second lumen 814B, and the cover portion 857 cooperatively engageable with the septum distal end 13e, if any, for at least minimizing backflow into the one of the first lumen 814A and the second lumen 814B, in accordance with an embodiment of the present disclosure. The cover portion 857 is deployable and retractable via at least one technique of a rotation and a translation in relation to a longitudinal axis A thereof (FIGS. 14a and 14B). The first intra-catheter stiffener element 851A, such as a stylet, includes at least one of a monolithic configuration and a tapered configuration, wherein the first intra-catheter stiffener element 851A includes a first length, wherein the second intra-catheter stiffener element 51B includes a second length, the second length less than the first length. The cover portion 857 includes a first orifice 862 and a second orifice 864 for accommodating the guide-wire 26B and optionally includes at least one of a conical or frusto-conical configuration and an oval cross-section. The stylet, such as the stylet 824A, includes an outer dimensions or sizes that conforms with a lumen's inner dimensions or sizes.

Figure 26:
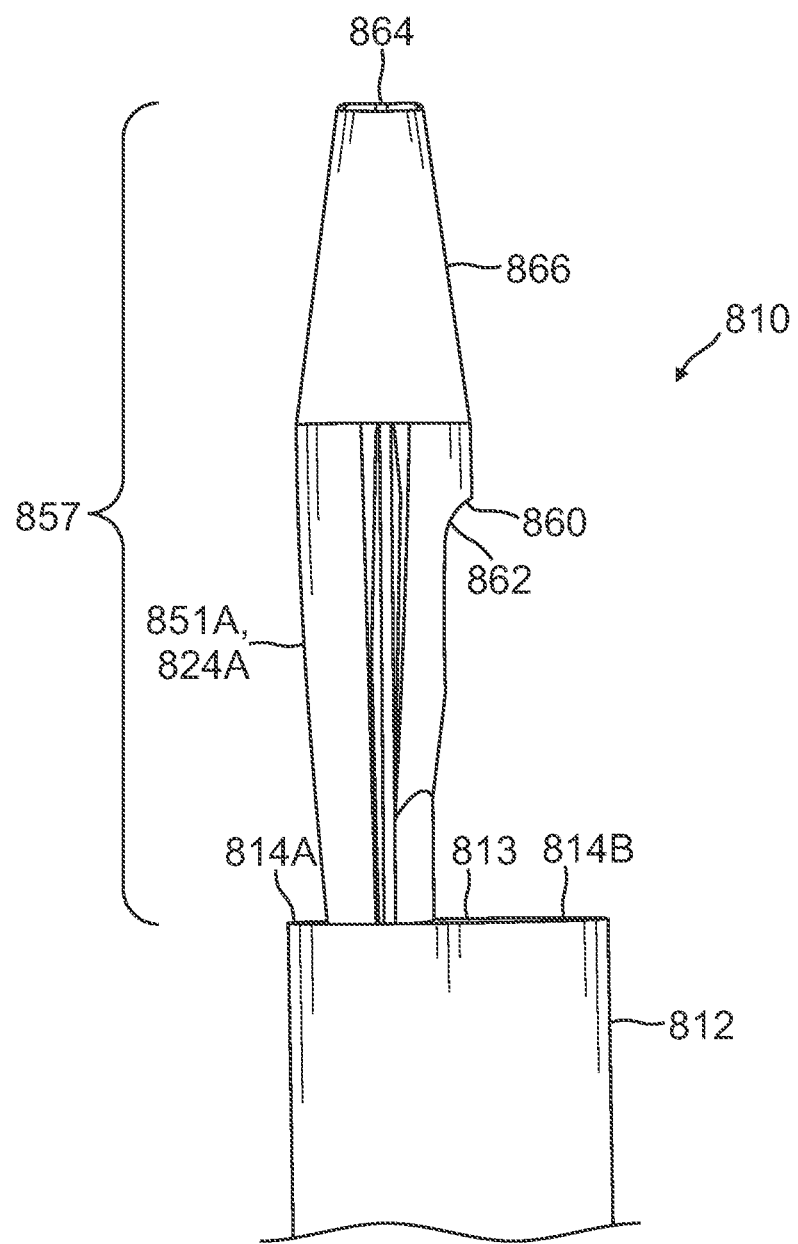
FIG. 26 is schematic diagram illustrating a cutaway side view of a catheter apparatus, e.g., of a catheter insertion system, in accordance with an embodiment of the present disclosure.

Referring to FIG. 26, this schematic diagram illustrates, in a cutaway side view, a catheter apparatus 810 of a catheter insertion system, comprising a catheter body 812 having two lumens 814A, 814B separated by a septum 813, a first intra-catheter stiffener element 851A, such as a single stylet 824A, disposed through one lumen 814A; and second intra-catheter stiffener element 51B, such as a single guide-wire 26B (FIGS. 24 and 25), disposable through the other lumen 814B, a distal end 53B of the guide-wire 26B (FIGS. 24 and 25) being disposable within at least one portion of the stylet 824A, such as useable in a catheter system, in accordance with an embodiment of the present disclosure.

The guide-wire 26B is insertable, e.g., "weavable" or "threadable," into the stylet 824A along at least a portion thereof, whereby a smooth transition is provided for enhancing stiffening and guiding of the catheter body 812. The stylet 824A is configured for inserting and translating through a lumen, such as the lumen 814A or the lumen 814B, for rotation, such as after insertion and translation, wherein a notched portion 860 of the stylet distal portion, e.g., a cover or overhang portion 857, is rotatable for optionally receiving the septum 813, e.g., if the septum 813 includes a septum distal end 13e extending from the septum 813 (FIGS. 13-15B), whereby further structural support is provided for enhancing stiffening and guiding of the catheter body 812, and for receiving a guide-wire (FIGS. 24 and 25), such as by way of a distal end 53B of the guide-wire 26B through a first orifice 862 and a second orifice 864 of the first intra-catheter stiffener element 851A, such as a single stylet 824A.

Figure 27:
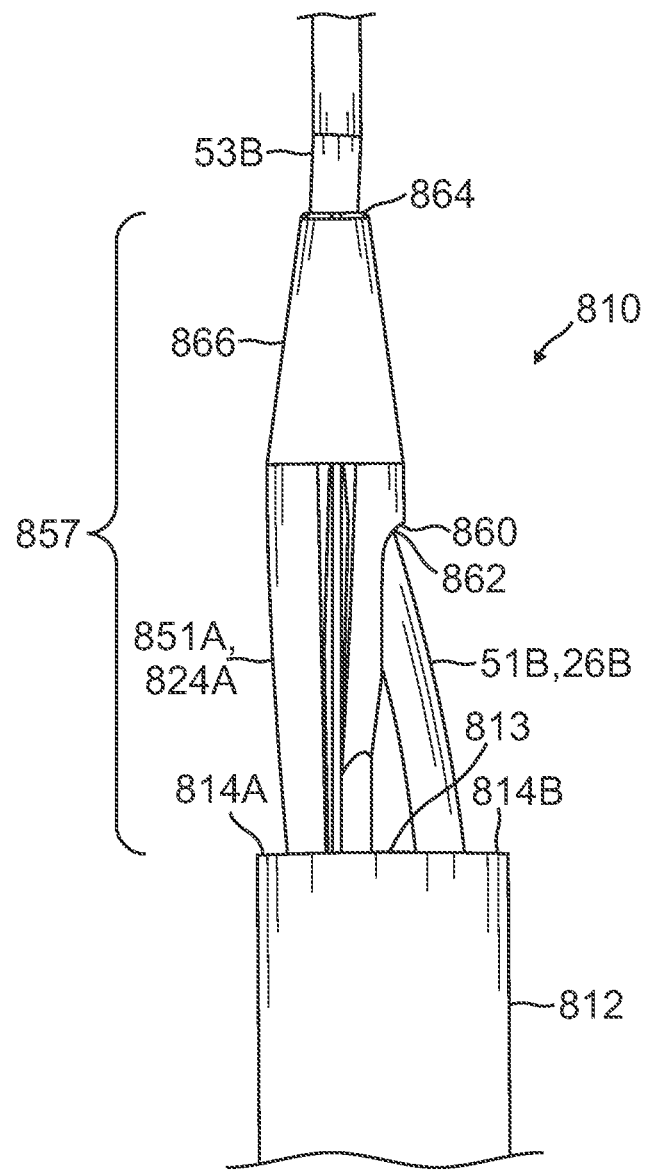
FIG. 27 is schematic diagram illustrating a cutaway side view of a catheter apparatus, e.g., of a catheter insertion system, as shown in FIG. 26, wherein a guide-wire is woven through a portion of a stylet, in accordance with an embodiment of the present disclosure.

Referring to FIG. 27, this schematic diagram illustrates, in a cutaway side view, a catheter apparatus 810 of a catheter insertion system, as shown in FIG. 26, comprising a catheter body 812 having two lumens 814A, 814B separated by a septum 813, a first intra-catheter stiffener element 851A, such as a single stylet 824A, disposed through one lumen 814A; and second intra-catheter stiffener element 51B, such as a single guide-wire 26B, disposed through the other lumen 814B, a distal end 53B of the guide-wire 26B disposed within at least one portion of the stylet 824A, such as useable in a catheter system, in accordance with an embodiment of the present disclosure.

The guide-wire 26B is insertable, e.g., "weavable" or "threadable," into the stylet 824A along at least a portion thereof, whereby a smooth transition is provided for enhancing stiffening and guiding of the catheter body 812. The stylet 824A is configured for inserting and translating through a lumen, such as the lumen 814A or the lumen 814B, for rotation, such as after insertion and translation, wherein a notched portion 860 of the stylet distal portion, e.g., a cover or overhang portion 857, is rotatable for optionally receiving the septum 813, e.g., if the septum 813 includes a septum distal end 13e extending from the septum 813 (FIGS. 13-15B), whereby further structural support is provided for enhancing stiffening and guiding of the catheter body 812, and for receiving a guide-wire, such as by way of a distal end 53B of the guide-wire 26B through a first orifice 862 and a second orifice 864 of the first intra-catheter stiffener element 851A, such as a single stylet 824A.

The intra-catheter stiffener elements described herein may be configured in such a way for disposition within the lumens of any of the catheter systems described within the present disclosure. The distal end of the first intra-catheter stiffener element 851A may be configured such that it is distal in relation to the distal end of septum 813 and a distal end of the second intra-catheter stiffener element 51B may be configured such that it is also distal in relation to the distal end of septum 813. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Figure 28:
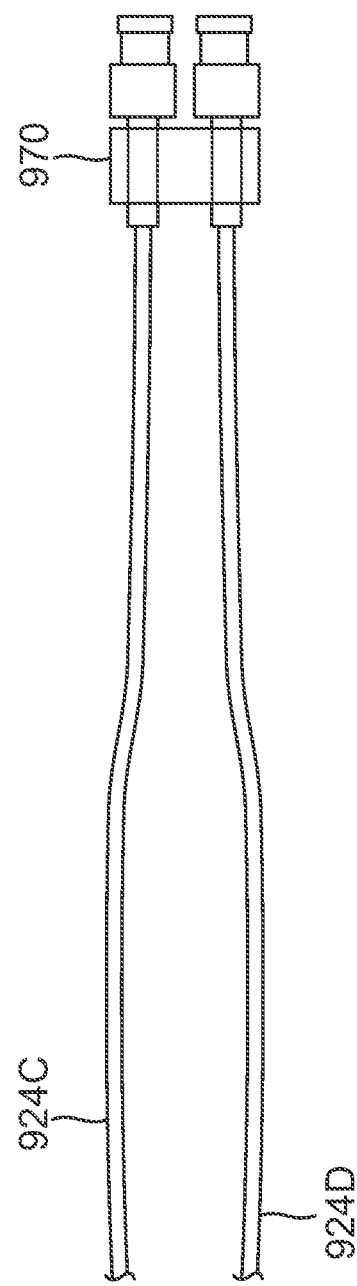
FIG. 28 is a schematic diagram illustrating a partially cutaway side view of a plurality of stylets, such as two stylets, joined at a proximal end, e.g., for use in a catheter system, in accordance with an embodiment of the present disclosure.

Referring to FIG. 28, this is a schematic diagram that illustrates a side view of a plurality of stylets 924C, 924D, such as two stylets, joined at a proximal end, such as by a joining member 970, for use in a catheter system (not shown), in accordance with an embodiment of the present disclosure. Optionally, the stylet tip is adapted to accept a guide-wire tip therein for enhancing stiffening. The stylets may be joined together in releasable fashion such that they can be introduced together as joined, separated after introduction through the catheter, or separated first, then introduced. The joining member 970 therefore can be permanently joined, for example, via adhesive or welding, or may be removable, such as a tape member or elastic member. The joining member 970 in one embodiment may be a removable joining member that snaps onto the proximal ends of the stylets, such as a form fitting plastic member.

Figure 29:
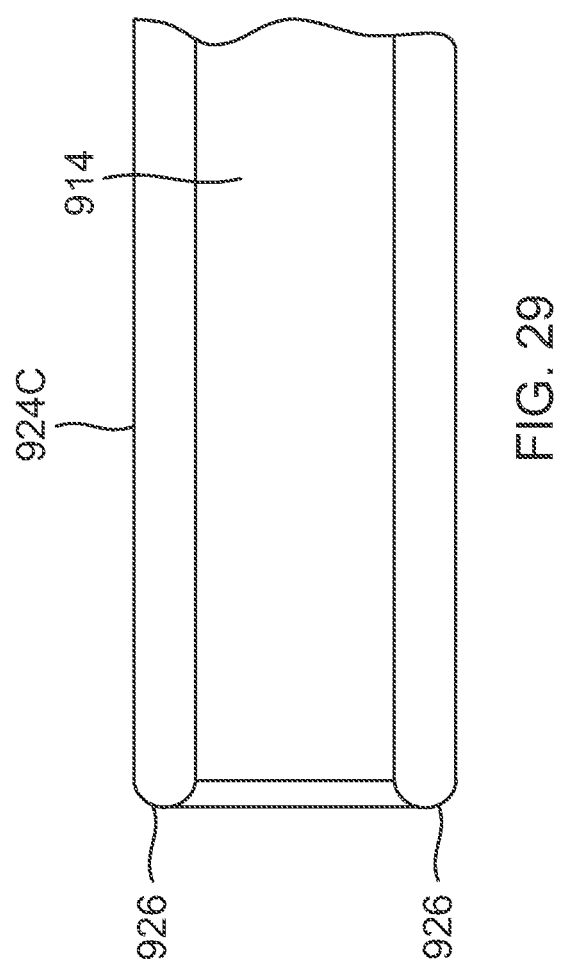
FIG. 29 is a schematic diagram illustrating a partially cutaway side view of a stylet of a plurality of stylets, e.g., for a hemodialysis catheter insertion system, each stylet of the plurality of stylets comprising tip having a hemi-toroidal configuration, rather than a tapered tip, in accordance with an embodiment of the present disclosure.

FIG. 29 is a schematic diagram illustrating a partially cutaway side view of a stylet 924C of a plurality of stylets 924C, 924D for a hemodialysis catheter insertion system (not shown), each stylet 924C of a plurality of stylets 924C, 924D having a lumen 914 extending along its length sized to accommodate a guide-wire (not shown) and a hemi-toroidal tip 926, rather than a tapered tip, whereby trauma to the blood vessel is minimized, in accordance with an embodiment of the present disclosure. In another embodiment only one of the plurality of stylets has a hemi-toroidal tip, and one or more of the other stylets has a tapered tip.

The intra-catheter stiffener elements described herein may be configured in such a way for disposition within the lumens of any of the catheter systems described within the present disclosure. The distal end of the first stylet 924C may be configured such that it is distal in relation to the distal end of the catheter apparatus (not shown) and a distal end of the second stylet 924D may be configured such that it is also distal in relation to the distal end of the catheter apparatus (not shown). The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Figure 30:
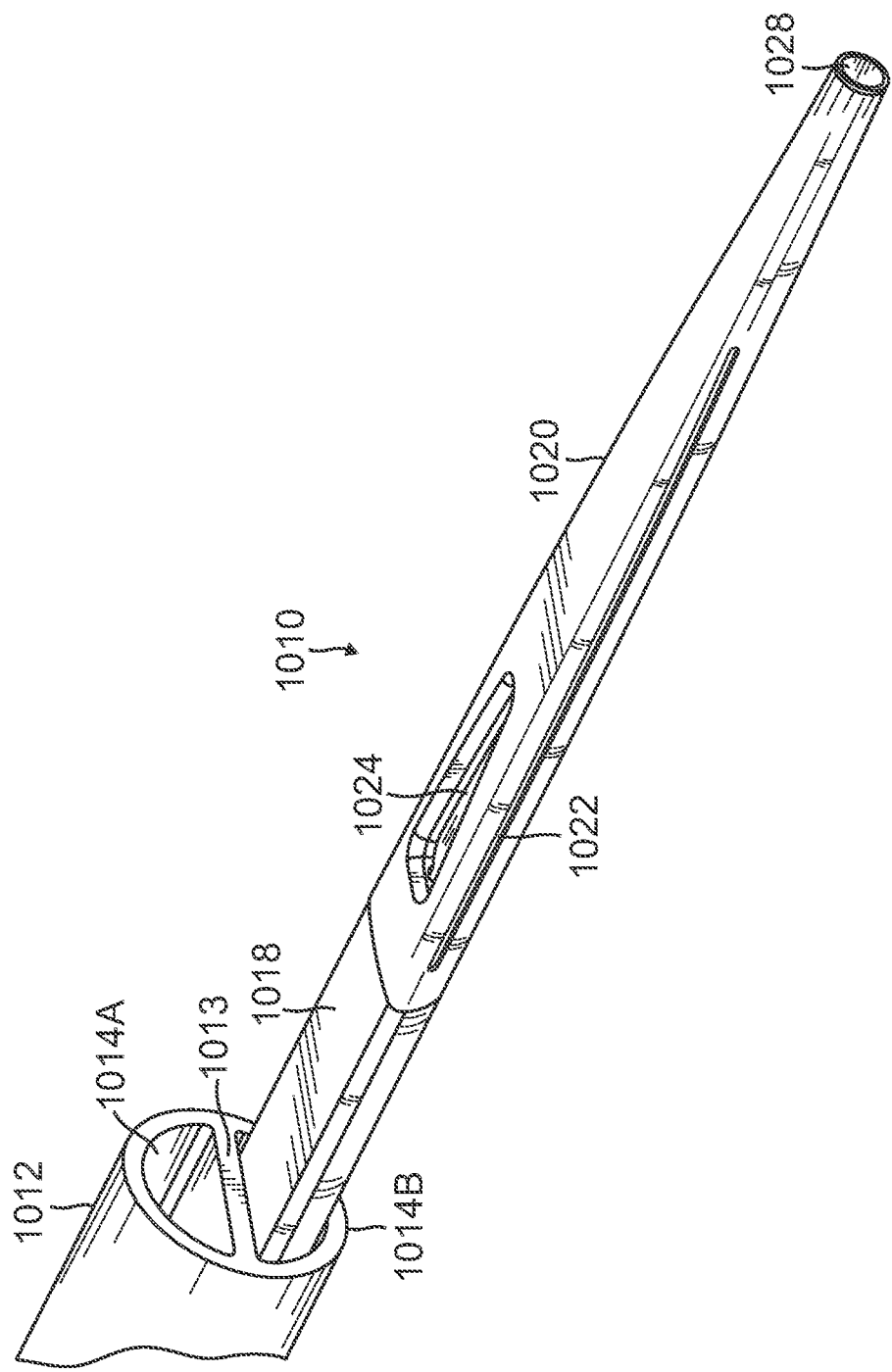
FIG. 30 is a schematic diagram illustrating a cut-away perspective view of an expandable catheter insertion system, having a stylet in an unexpanded condition, in accordance with an embodiment of the present disclosure.

Referring to FIG. 30, this schematic diagram illustrates, in a cut-away perspective view, an expandable catheter insertion system 1010, having a stylet in an unexpanded condition, in accordance with an embodiment of the present disclosure. The catheter system 1010 includes: a catheter body 1012 including: two internal lumens 1014A and 1014B; a septum 1013, the septum 1013 separating the lumens 1014A, 1014B; a stylet 1018 having a stylet tip 1020; and a guide-wire 26B (not shown) having a guide-wire tip 1026 (not shown). The stylet tip 1020 includes at least one expansion feature 1022, such as an expansion slit, and at least one opening for accommodating a guide-wire 26 (not shown), such as an entry opening 1024 and an exit opening 1028, e.g., by "threading" or "weaving" the guide-wire tip 1026 (not shown) through the lumen 1014A, along the stylet 1018, through the entry opening 1024 and through the exit opening 1028. The guide-wire 26 (not shown) facilitates further stiffening and guiding of the catheter body 1012 through a blood vessel. By example only, the stylet tip 1020 includes at least one configuration of a tapered configuration and elliptical cross-section and a frusto-conical configuration.

Figure 31:
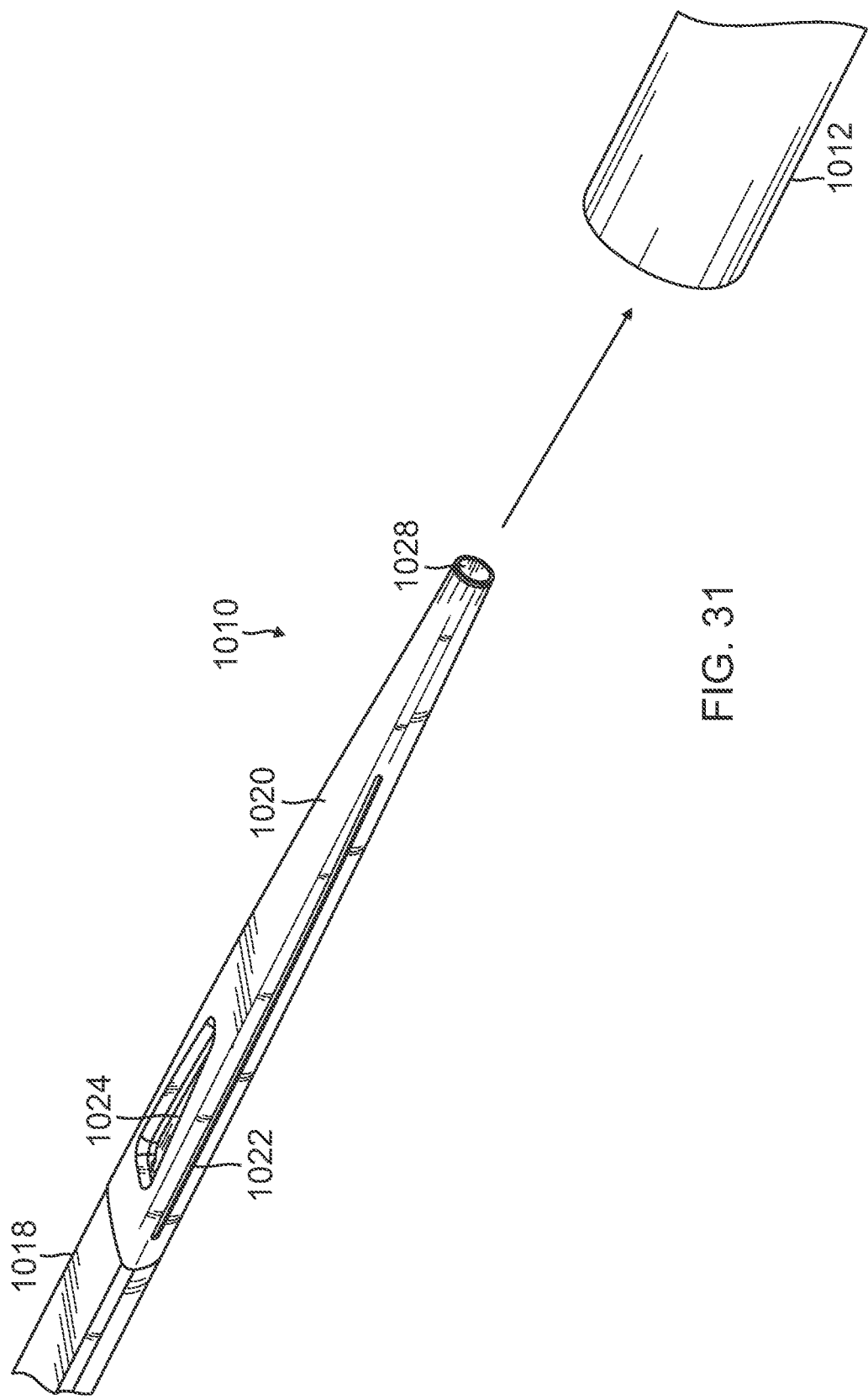
FIG. 31 is a schematic diagram illustrating an exploded cut-away perspective view of an expandable catheter insertion system, having a stylet in an unexpanded condition, in accordance with an embodiment of the present disclosure.

Referring to FIG. 31, this schematic diagram illustrates, in an exploded cut-away perspective view, an expandable (e.g., deformable and reformable) catheter insertion system 1010, having a stylet in an unexpanded condition, in accordance with an embodiment of the present disclosure. The catheter system 1010 includes: a catheter body 1012 comprising: two internal lumens 1014A and 1014B; a septum 1013, the septum 1013 separating the lumens 1014A, 1014B; a stylet 1018 having a stylet tip 1020; and a guide-wire 26 (not shown) having a guide-wire tip 1026 (not shown). The stylet tip 1020 includes least one expansion feature 1022, such as an expansion slit, and at least one opening for accommodating a guide-wire 26 (not shown), such as an entry opening 1024 and an exit opening 1028, e.g., by "weaving" or "threading" the guide-wire tip 1026 (not shown) through the lumen 1014A, along the stylet 1018, through the entry opening 1024 and through the exit opening 1028. The guide-wire 26 (not shown) facilitates further stiffening and guiding of the catheter body 1012 through a blood vessel. By example only, the stylet tip 1020 includes at least one configuration of a tapered configuration and elliptical cross-section and a frusto-conical configuration.

Figure 32:
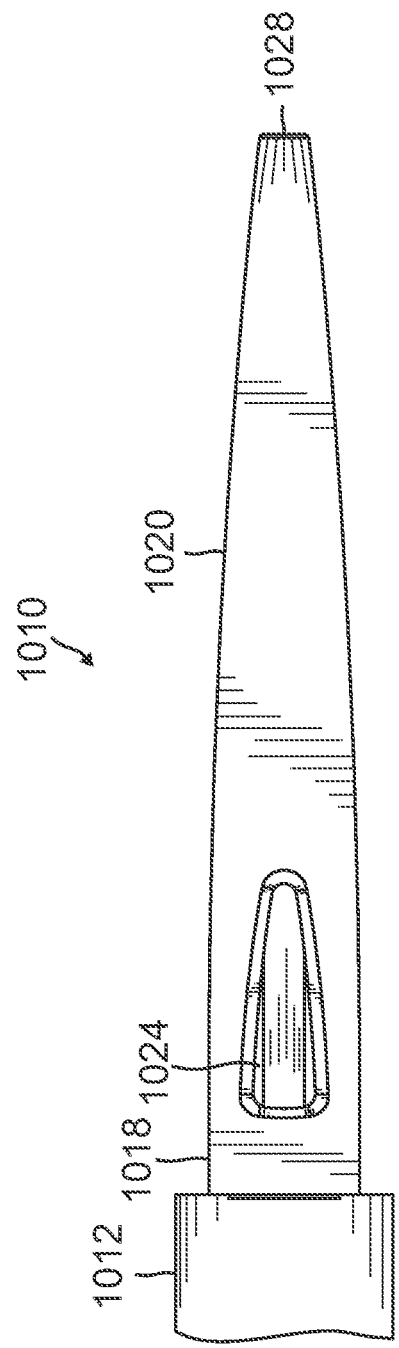
FIG. 32 is a schematic diagram illustrating a cut-away top view of an expandable catheter insertion system, having a stylet in an unexpanded condition, in accordance with an embodiment of the present disclosure.

Referring to FIG. 32, this schematic diagram illustrates, in a cut-away top view, an expandable catheter insertion system 1010, having a stylet in an unexpanded condition, in accordance with an embodiment of the present disclosure. The catheter system 1010 includes: a catheter body 1012 including: two internal lumens 1014A and 1014B; a septum 1013, the septum 1013 separating the lumens 1014A, 1014B; a stylet 1018 having a stylet tip 1020; and a guide-wire 26 (not shown) having a guide-wire tip 1026 (not shown). The stylet tip 1020 includes at least one expansion feature 1022, such as an expansion slit, and at least one opening for accommodating a guide-wire 26 (not shown), such as an entry opening 1024 and an exit opening 1028, e.g., by "weaving" or "threading" the guide-wire tip 1026 (not shown) through the lumen 1014A, along the stylet 1018, through the entry opening 1024 and through the exit opening 1028. The guide-wire 26 (not shown) facilitates further stiffening and guiding of the catheter body 1012 through a blood vessel. By example only, the stylet tip 1020 includes at least one configuration of a tapered configuration and elliptical cross-section and a frusto-conical configuration.

Figure 33:
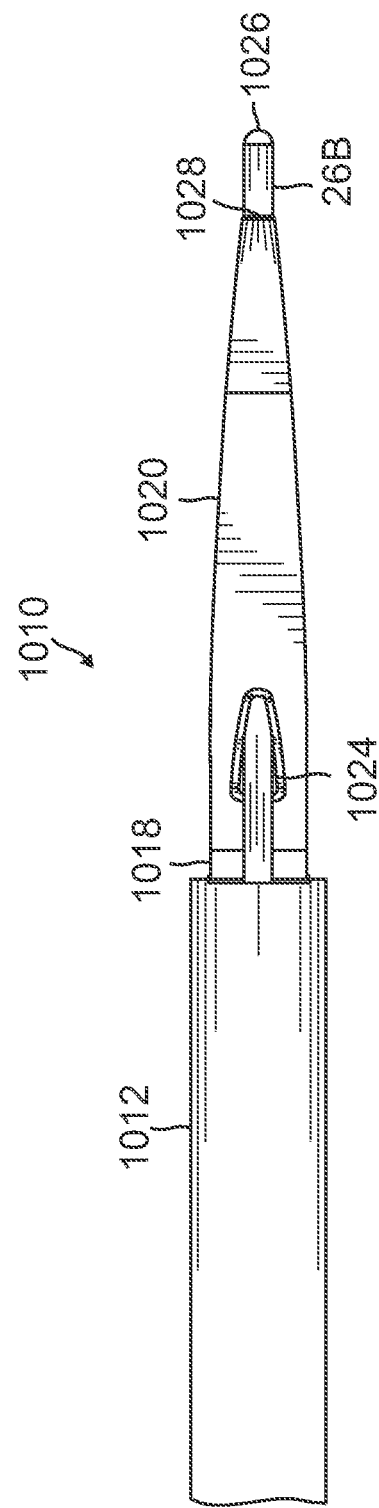
FIG. 33 is a schematic diagram illustrating a cut-away top view of an expandable catheter insertion system, having a stylet in an expanded condition and a guide-wire disposed therethrough, the guide-wire facilitating expansion of the stylet, in accordance with an embodiment of the present disclosure.

Referring to FIG. 33, this schematic diagram illustrates, in a cut-away top view, an expandable catheter insertion system 1010, having a stylet in an expanded condition and a guide-wire disposed therethrough, the guide-wire facilitating expansion of the stylet, in accordance with an embodiment of the present disclosure. The catheter system 1010 includes: a catheter body 1012 including: two internal lumens 1014A and 1014B; a septum 1013, the septum 1013 separating the lumens 1014A, 1014B; a stylet 1018 having a stylet tip 1020; and a guide-wire 26 having a guide-wire tip 1026. The stylet tip 1020 includes least one expansion feature 1022, such as an expansion slit, and at least one opening for accommodating a guide-wire 26, such as an entry opening 1024 and an exit opening 1028, e.g., by "weaving" or "threading" the guide-wire tip 1026 through the lumen 1014A, along the stylet 1018, through the entry opening 1024 and through the exit opening 1028. The guide-wire 26 facilitates further stiffening and guiding of the catheter body 1012 through a blood vessel. By example only, the stylet tip 1020 includes at least one configuration of a tapered configuration and elliptical cross-section and a frusto-conical configuration.

Figure 34:
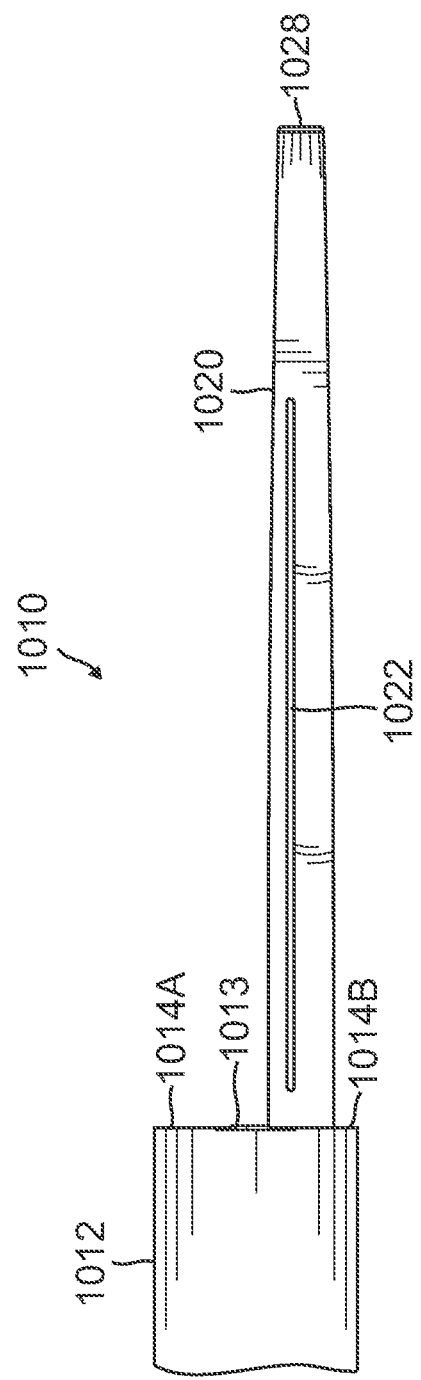
FIG. 34 is a schematic diagram illustrating a cut-away side view of an expandable catheter insertion system, having a stylet in an unexpanded condition, wherein the stylet includes at least one slit for facilitating expansion, in accordance with an embodiment of the present disclosure.

Referring to FIG. 34, this schematic diagram illustrates, in a cut-away side view, an expandable catheter insertion system 1010, having a stylet in an unexpanded condition, wherein the stylet includes at least one slit for facilitating expansion, in accordance with an embodiment of the present disclosure. The catheter system 1010 includes: a catheter body 1012 including: two internal lumens 1014A and 1014B; a septum 1013, the septum 1013 separating the lumens 1014A, 1014B; a stylet 1018 having a stylet tip 1020; and a guide-wire 26 (not shown) having a guide-wire tip 1026 (not shown). The stylet tip 1020 includes least one expansion feature 1022, such as an expansion slit, and at least one opening for accommodating a guide-wire 26 (not shown), such as an entry opening 1024 and an exit opening 1028, e.g., by "weaving" or "threading" the guide-wire tip 1026 (not shown) through the lumen 1014A, along the stylet 1018, through the entry opening 1024 and through the exit opening 1028. The guide-wire 26 (not shown) facilitates further stiffening and guiding of the catheter body 1012 through a blood vessel. By example only, the stylet tip 1020 includes at least one configuration of a tapered configuration and elliptical cross-section and a frusto-conical configuration.

Figure 35:
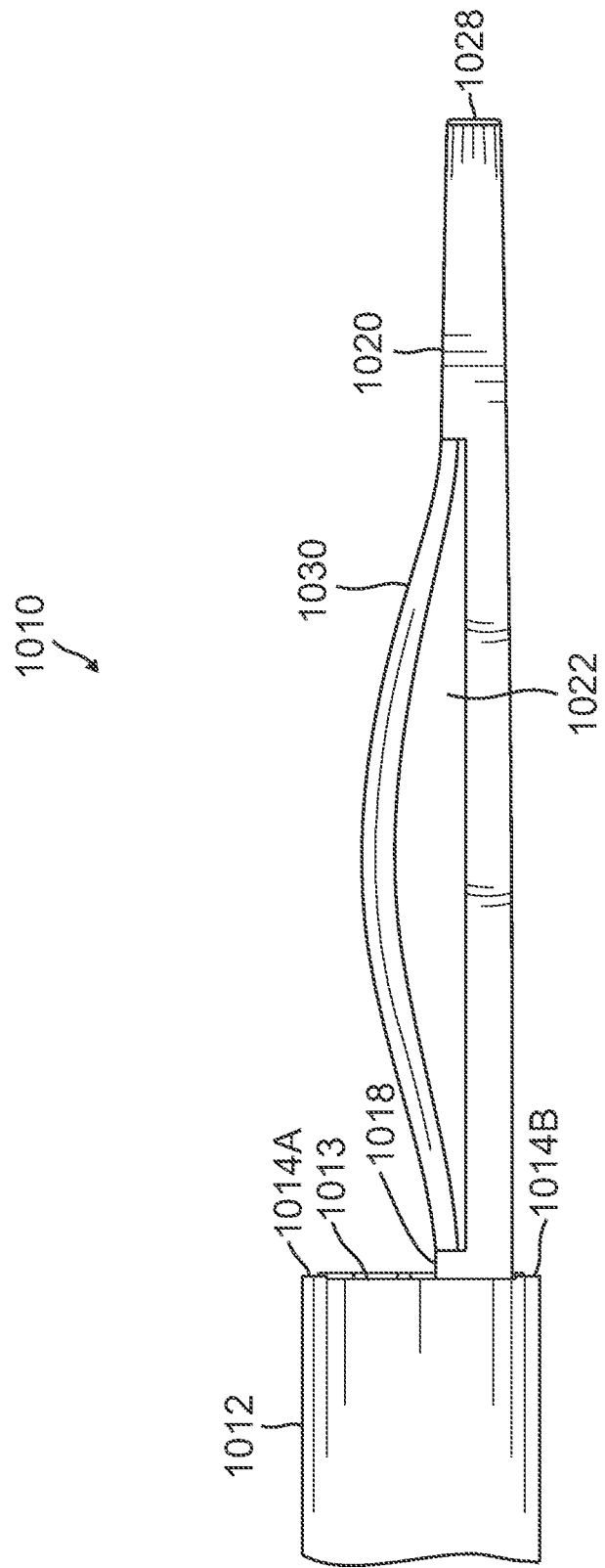
FIG. 35 is a schematic diagram illustrating a cut-away side view of an expandable catheter insertion system, having a stylet in an expanded condition, in accordance with an embodiment of the present disclosure.

Referring to FIG. 35, this schematic diagram illustrates, in a cut-away side view, an expandable catheter insertion system 1010, having a stylet 1018 in an expanded condition, in accordance with an embodiment of the present disclosure. The catheter system 1010 includes: a catheter body 1012 including: two internal lumens 1014A and 1014B; a septum 1013, the septum 1013 separating the lumens 1014A, 1014B; a stylet 1018 having a stylet tip 1020; and a guide-wire 26 (not shown) having a guide-wire tip 1026 (not shown). The stylet tip 1020 includes least one expansion feature 1022, such as an expansion slit, and at least one opening for accommodating a guide-wire 26 (not shown), such as an entry opening 1024 and an exit opening 1028, e.g., by "weaving" or "threading" the guide-wire tip 1026 (not shown) through the lumen 1014A, along the stylet 1018, through the entry opening 1024 and through the exit opening 1028. The guide-wire 26 (not shown) facilitates further stiffening and guiding of the catheter body 1012 through a blood vessel. By example only, the stylet tip 1020 includes at least one configuration of a tapered configuration and elliptical cross-section and a frusto-conical configuration. The stylet tip 1020 includes of a portion 1030 that is deflectable for accommodating the guide-wire 26 (not shown).

Figure 36:
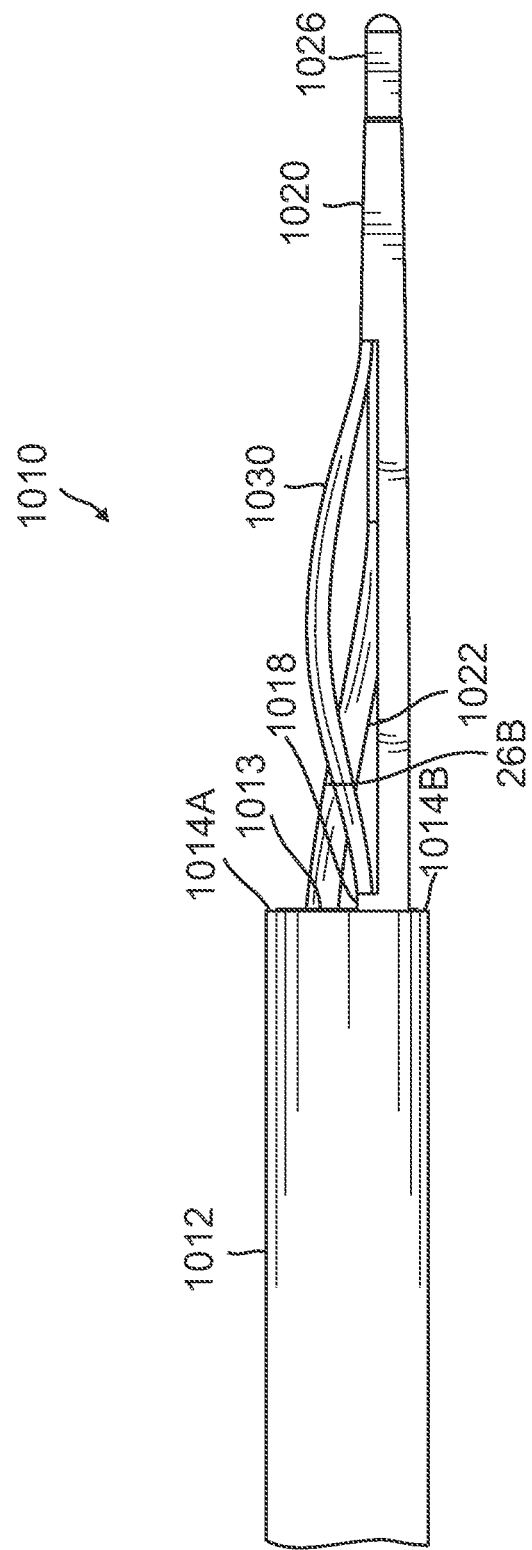
FIG. 36 is a schematic diagram illustrating a cut-away side view of a catheter insertion system, having a stylet in an expanded condition and a guide-wire disposed therethrough, the guide-wire facilitating expansion of the stylet, in accordance with an embodiment of the present disclosure.

Referring to FIG. 36, this schematic diagram illustrates, in a cut-away side view, a catheter insertion system 1010, having a stylet 1018 in an expanded condition and a guide-wire 26 disposed therethrough, the guide-wire 26 facilitating expansion of the stylet 1018, in accordance with an embodiment of the present disclosure. The catheter system 1010 includes: a catheter body 1012 including: two internal lumens 1014A and 1014B; a septum 1013, the septum 1013 separating the lumens 1014A, 1014B; a stylet 1018 having a stylet tip 1020; and a guide-wire 26 having a guide-wire tip 1026. The stylet tip 1020 includes least one expansion feature 1022, such as an expansion slit, and at least one opening for accommodating a guide-wire 26, such as an entry opening 1024 and an exit opening 1028, e.g., by "weaving" or "threading" the guide-wire tip 1026 through the lumen 1014A, along the stylet 1018, through the entry opening 1024 and through the exit opening 1028. The guide-wire 26 facilitates further stiffening and guiding of the catheter body 1012 through a blood vessel. By example only, the stylet tip 1020 includes at least one configuration of a tapered configuration and elliptical cross-section and a frusto-conical configuration. The stylet tip 1020 includes a portion 1030 of is deflectable for accommodating the guide-wire 26.

Figure 37:
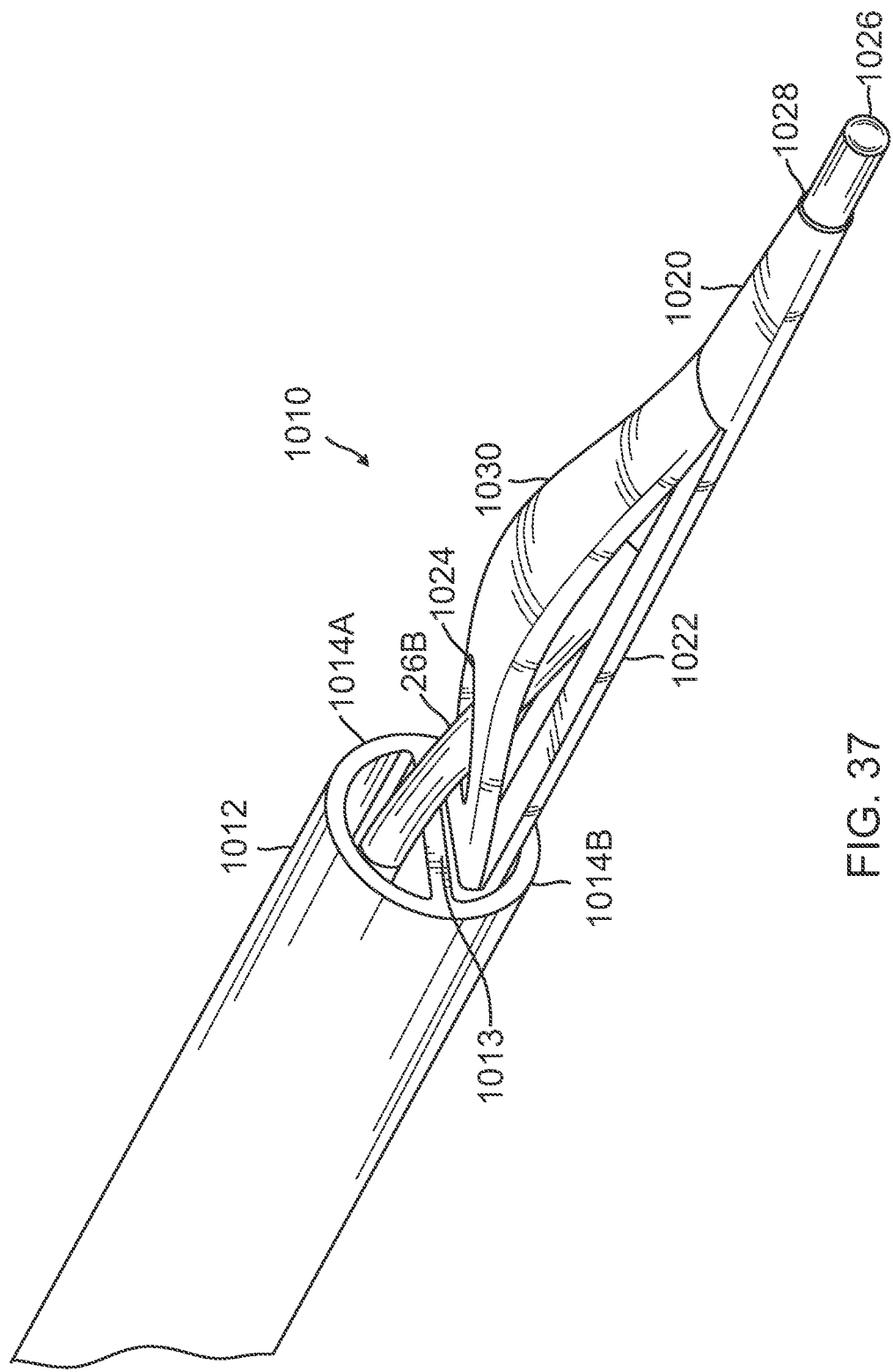
FIG. 37 is a schematic diagram illustrating a cut-away perspective view of a catheter insertion system, having a stylet in an expanded condition and a guide-wire disposed therethrough, the guide-wire facilitating expansion of the stylet, in accordance with an embodiment of the present disclosure.

Referring to FIG. 37, this a schematic diagram illustrates, in a cut-away perspective view, a catheter insertion system 1010, having a stylet 1018 in an expanded condition and a guide-wire 26B disposed therethrough, the guide-wire 26B facilitating expansion of the stylet 1018, in accordance with an embodiment of the present disclosure. The catheter system 1010 includes: a catheter body 1012 comprising: two internal lumens 1014A and 1014B; a septum 1013, the septum 1013 separating the lumens 1014A, 1014B; a stylet 1018 having a stylet tip 1020; and a guide-wire 26B having a guide-wire tip 1026. The stylet tip 1020 includes least one expansion feature 1022, such as an expansion slit, and at least one opening for accommodating a guide-wire 26, such as an entry opening 1024 and an exit opening 1028, e.g., by "weaving" or "threading" the guide-wire tip 1026 through the lumen 1014A, along the stylet 1018, through the entry opening 1024 and through the exit opening 1028. The guide-wire 26 facilitates further stiffening and guiding of the catheter body 1012 through a blood vessel. By example only, the stylet tip 1020 includes at least one configuration of a tapered configuration and elliptical cross-section and a frusto-conical configuration. The stylet tip 1020 includes a portion 1030 of is deflectable for accommodating the guide-wire 26.

The intra-catheter stiffener elements described herein may be configured in such a way for disposition within the lumens of any of the catheter systems described within the present disclosure. The distal end of the first intra-catheter stiffener element 1018 may be configured such that it is distal in relation to the distal end of septum 1013 and a distal end of the second intra-catheter stiffener element 26B may be configured such that it is also distal in relation to the distal end of the distal end of septum 1013. The distal end of the first intra-catheter stiffener element and the distal end of the second intra-catheter stiffener element may be capable of receiving and accommodating the other of the first intra-catheter stiffener element distal end and the second intra-catheter stiffener element distal end as described in various embodiments herein.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Features and/or steps described with respect to one embodiment may be incorporated into other embodiments.

Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the present disclosure.

What is claimed:

1. A catheter assembly, comprising:
   a multi-lumen catheter, comprising:
      a first lumen in fluid communication with a first distal opening; and
      a second lumen in fluid communication with a second distal opening;
   a stylet designed for insertion through the first lumen, the stylet having a length greater than a length of the first lumen such that a distal portion of the stylet can extend distal of the first distal opening, the distal portion of the stylet comprising:
      a stylet distal opening;
      a stylet proximal opening in communication with the stylet distal opening; and
      an expandable portion comprising a first expansion side and a second expansion side at least partially separable from the first expansion side, the stylet proximal opening formed through the first expansion side; and
   a guide-wire designed for insertion through the second lumen, the stylet proximal opening, and the stylet distal opening.

2. The catheter assembly according to claim 1, wherein the expandable portion includes an expansion slit, the first expansion side and the second expansion side separable along the expansion slit.

3. The catheter assembly according to claim 2, wherein the expansion slit travels through an entire width of the distal portion of the stylet.

4. The catheter assembly according to claim 1, wherein the distal portion of the stylet is tapered from a first width at a proximal end of the distal portion to a second width less than the first width at a distal end of the distal portion.

5. The catheter assembly according to claim 1, wherein the first expansion side has a flat surface and the second expansion side has a curved surface.

6. The catheter assembly according to claim 5, wherein the stylet proximal opening tapers from a first width at a proximal end to a second width less than the first width at a distal end.

7. A method of using the catheter assembly according to claim 1, comprising:
   positioning the guide-wire in a blood vessel with a distal end of the guide-wire at a desired location;
   inserting the stylet through the first lumen of the multi-lumen catheter such that the distal portion of the stylet extends distal of the first distal opening of the multi-lumen catheter;
   feeding a proximal end of the guide-wire through the stylet distal opening, the stylet proximal opening, and the second lumen of the multi-lumen catheter; and
   guiding the multi-lumen catheter and the stylet together over the guide-wire to the desired location.

* * * * *